US009925258B2

(12) United States Patent
Parks et al.

(10) Patent No.: US 9,925,258 B2
(45) Date of Patent: Mar. 27, 2018

(54) REPLICATION-COMPETENT VSV-HIV ENV VACCINES

(71) Applicant: International AIDS Vaccine Initiative, New York, NY (US)

(72) Inventors: Christopher L. Parks, New York, NY (US); Wayne C. Koff, New York, NY (US)

(73) Assignee: INTERNATIONAL AIDS VACCINE INITIATIVE, New York, NY (US)

( * ) Notice: Subject to any disclaimer, the term of this patent is extended or adjusted under 35 U.S.C. 154(b) by 0 days.

(21) Appl. No.: 15/280,710

(22) Filed: Sep. 29, 2016

(65) Prior Publication Data
US 2017/0095551 A1    Apr. 6, 2017

Related U.S. Application Data

(60) Provisional application No. 62/236,448, filed on Oct. 2, 2015.

(51) Int. Cl.
*A61K 39/12* (2006.01)
*A61K 39/21* (2006.01)
*A61K 39/108* (2006.01)
*C12N 15/68* (2006.01)
*C12N 15/70* (2006.01)
*C12N 7/00* (2006.01)
*C07K 14/005* (2006.01)
*A61K 39/00* (2006.01)

(52) U.S. Cl.
CPC ............ *A61K 39/21* (2013.01); *C07K 14/005* (2013.01); *C12N 7/00* (2013.01); *A61K 2039/5254* (2013.01); *A61K 2039/5256* (2013.01); *A61K 2039/542* (2013.01); *A61K 2039/543* (2013.01); *A61K 2039/575* (2013.01); *C07K 2319/03* (2013.01); *C12N 2740/15022* (2013.01); *C12N 2740/15034* (2013.01); *C12N 2740/15071* (2013.01); *C12N 2740/16111* (2013.01); *C12N 2740/16122* (2013.01); *C12N 2740/16134* (2013.01); *C12N 2740/16171* (2013.01); *C12N 2760/20222* (2013.01); *C12N 2760/20243* (2013.01); *C12N 2760/20244* (2013.01); *C12N 2810/6054* (2013.01); *C12N 2810/6081* (2013.01)

(58) Field of Classification Search
CPC ............ A61K 2039/5256; A61K 38/00; A61K 48/00; C07K 14/005; C07K 14/47
See application file for complete search history.

(56) References Cited

U.S. PATENT DOCUMENTS

2013/0095556 A1    4/2013  Parks et al.
2013/0266611 A1*  10/2013  Rabinovich ............ A61K 39/21
                                                                424/208.1

FOREIGN PATENT DOCUMENTS

| EP | 2 586 461 | 5/2013 |
| EP | 2 644 701 | 10/2013 |
| EP | 2 676 676 | 12/2013 |
| WO | 2005/098009 | 10/2005 |
| WO | 2010/096678 | 8/2010 |

OTHER PUBLICATIONS

European Search Report dated Feb. 28, 2017, which issued during prosecution of European Application No. 16002117.6.
Clarke, et al. "Neurovirulence and Immunogenicity of Attenuated Recombinant Vesicular Stomatitis Viruses in Nonhuman Primates" Journal of Virology, Jun. 2014, 88(12):6690-6701.
Lorenz, et al. "The Stem of Vesicular Stomatitis Virus G Can Be Replaced With the HIV-1 Env Membrane-Proxima External Region Without Loss of G Function or Membrane-Proximal External Region Antigenic Properties" AIDS Research and Human Retroviruses, Nov. 2014, 30(11):1130-1144.
Parks. "Development of Live VSV Vectors for Delivery of AIDS Vaccines" Conference Abstracts, 14th International NegativeStrand Virus Meeting, Jan. 2010, Bruges, Belgium.
Parks, et al. "Development of replication-competent viral vectors for HIV vaccine delivery" Current Opinion in HIV and AIDS, Sep. 2013, 8(5):402-411.
Parks, et al. "Development of VSV Vectors for Delivery of ENV Immunogens" Conference Abstracts, AIDS Vaccine, Oct. 2010, Atlanta, Georgia.
Parks, et al. "Viral vector delivery of Env trimer immunogens" Retrovirology, Sep. 2012, 9(Suppl 2):341.
Wright, et al. "Optimizing expression of functional HIV envelopes in rVSV-ΔG vaccine vectors", Retrovirology, Sep. 2012, 9(Suppl 2):342.

* cited by examiner

*Primary Examiner* — Barry A Chestnut
(74) *Attorney, Agent, or Firm* — Vedder Price P.C.; Thomas J. Kowalski; Deborah L. Lu

(57) ABSTRACT

The present relation relates to recombinant vesicular stomatitis virus for use as prophylactic and therapeutic vaccines for infectious diseases of AIDS. The present invention encompasses the preparation and purification of immunogenic compositions which are formulated into the vaccines of the present invention.

10 Claims, 43 Drawing Sheets

Recombinant VSVΔG-Env.BG505 pre-Master Virus Seed (preMVS)

```
┌─────────────────────────────────────────────────────────────────┐
│  Plasmids required for recombinant VSVΔG-Env.BG505 rescue       │
│  prepared using animal-product free conditions                   │
└─────────────────────────────────────────────────────────────────┘
                               ↓
┌─────────────────────────────────────────────────────────────────┐
│  Recombinant VSVΔG-Env.BG505 rescue by electroporation of       │
│  VeroCD4/CCR5 cells                                              │
└─────────────────────────────────────────────────────────────────┘
                               ↓
┌─────────────────────────────────────────────────────────────────┐
│  Expansion of rescued virus in VeroCD4/CCR5 cell monolayers     │
└─────────────────────────────────────────────────────────────────┘
                               ↓
┌─────────────────────────────────────────────────────────────────┐
│  Verify Env expression and Env gene sequence                     │
└─────────────────────────────────────────────────────────────────┘
                               ↓
┌─────────────────────────────────────────────────────────────────┐
│  Three rounds of clonal isolation by limiting dilution or        │
│  plaque isolation                                                │
└─────────────────────────────────────────────────────────────────┘
                               ↓
┌─────────────────────────────────────────────────────────────────┐
│  Expand clonal isolates and verify Env expression, Env insert    │
│  integrity, and genomic sequence                                 │
└─────────────────────────────────────────────────────────────────┘
                               ↓
┌─────────────────────────────────────────────────────────────────┐
│  Select clonal isolate and amplify preMVS                        │
└─────────────────────────────────────────────────────────────────┘
                               ↓
┌─────────────────────────────────────────────────────────────────┐
│  Confirm Env expression, Env insert integrity, and genomic       │
│  sequence of preMVS                                              │
└─────────────────────────────────────────────────────────────────┘
                               ↓
┌─────────────────────────────────────────────────────────────────┐
│  Mock manufacturing amplification of preMVS and confirm Env      │
│  expression, gene insert integrity, gene insert sequence         │
└─────────────────────────────────────────────────────────────────┘
                               ↓
┌─────────────────────────────────────────────────────────────────┐
│  Confirm preMVS sterility and lack of mycoplasma contamination   │
└─────────────────────────────────────────────────────────────────┘
```

VeroCD4/CCR5 cells

FIG. 12

Preparation of VSVΔG-Env.BG505 with G pseudotype

Electroporate VeroCD4/CCR5 cells with solution containing pDNA-G and VSVΔG-Env.BG505 particles → Culture 48-72 hours (Vero CD4-CCR5, G supplied in trans) → Harvest medium supernatant (VSVΔG-Env.BG505 with G pseudotype, Env + G)

1. VERT3 P1
2. VERT3 P2
3. VERT3 P3
4. VERT3 P10 (+) control
5. Vero cells (-)

| Sample | Copies | | Number of |
| --- | --- | --- | --- |
| | CD4 | B-Glue | CD4 copies per cell |
| VERT3 P1 | 1.71E+04 | 1.65E+04 | 2.08 |
| VERT3 P2 | 1.78E+04 | 1.70E+04 | 2.10 |
| VERT3 P3 | 2.22E+04 | 2.34E+04 | 1.90 |

Sera wk 48
VSVΔGps-Env.BG505

Clade A
BG505

Clade B
SF162p3

Clade C
CH505.w100

FIG. 38

SEQUENCE LISTING

```
<160> NUMBER OF SEQ ID NOS: 7

<210> SEQ ID NO 1
<211> LENGTH: 14258
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3198)..(5354)

<400> SEQUENCE: 1
aaattaatac gactcactat agggagacca caacggtttc cctctagcgt tgtcttcgtc      60
tgatgagtcc gtgaggacga aactatagga aaggaattcc tatagtcacg aagacaaaca     120
aaccattatt atcattaaaa ggctcaggag aaactttaac agtaatcaaa atgtctgtta     180
cagtcaagag aatcattgac aacacagtca tagttccaaa acttcctgca aatgaggatc     240
cagtggaata cccggcagat tacttcagaa aatcaaagga gattcctctt tacatcaata     300
ctacaaaaag tttgtcagat ctaagaggat atgtctacca aggcctcaaa tccggaaatg     360
tatcaatcat acatgtcaac agctacttgt atggagcatt gaaggacatc cggggtaagt     420
tggataaaga ttggtcaagt tcggaataac acatcggaa ggcaggggat acaatcggaa     480
tatttgacct tgtatccttg aaagccctgg acggtgtact tccagatgga gtatcggatg     540
cttccagaac cagcgcagat gacaaatggt tgcctttgta tctacttggc ttatacagag     600
tgggcagaac acaaatgcct gaatacagaa aaaggctcat ggatgggctg acaaatcaat     660
gcaaaatgat caatgaacag tttgaacctc ttgtgccaga aggtcgtgac atttttgatg     720 tgtgggaaa tgacagtaat tacacaaaaa ttgtcgctgc agtggacatg ttcttccaca     780
tgttcaaaaa acatgaatgt gcctcgttca gatacgaac tattgtttcc agattcaaag     840
attgtgctgc attggcaaca tttggacacc tctgcaaaat aaccggaatg tctacagaag     900
```

```
atgtgacgac ctggatcttg aaccgagaag ttgcagatga gatggtccaa atgatgcttc    960
caggccaaga aattgacaag gctgattcat acatgcctta tttgatcgac tttggattgt   1020
cttctaagtc tccatattct tccgtcaaaa accctgcctt ccacttctgg gggcaattga   1080
cagctcttct gctcagatcc accagagcaa ggaatgcccg acagcctgat gacattgagt   1140
atacatctct tactacagca ggtttgttgt acgcttatgc agtaggatcc tctgctgact   1200
tggcacaaca gttttgtgtt ggagatagca aatacactcc agatgatagt accgaggat    1260
tgacgactaa tgcaccgcca caaggcagag atgtggtcga atggctcgga tggtttgaag   1320
atcaaaacag aaaaccgact cctgatatga tgcagtatgc gaaacgagca gtcatgtcac   1380
tgcaaggcct aagagagaag acaattggca agtatgctaa gtcagagttt gacaaatgac   1440
cctataattc tcagatcacc tattatatat tatgctagct atgaaaaaaa ctaacagata   1500
tcatggataa tctcacaaaa gttcgtgagt atctcaagtc ctattctcgt ctagatcagg   1560
cggtaggaga gatagatgag atcgaagcac aacgagctga aaagtccaat tatgagttgt   1620
tccaagagga cggagtggaa gagcatacta ggccctctta ttttcaggca gcagatgatt   1680
ctgacacaga atctgaacca gaaattgaag acaatcaagg cttgtatgta ccagatccgg   1740
aagctgagca agttgaaggc tttatacagg ggcctttaga tgactatgca gatgaggacg   1800
tggatgttgt attcacttcg gactggaaac agcctgagct tgaatccgac gagcatggaa   1860
agaccttacg gttgacattg ccagaggggtt taagtggaga gcagaaatcc cagtggcttt   1920
tgacgattaa agcagtcgtt caaagtgcca acactggaa tctggcagag tgcacatttg   1980
aagcatcggg agaaggggtc atcataaaaa agcgccagat aactccggat gtatataagg   2040
tcactccagt gatgaacaca catccgtccc aatcagaagc cgtatcagat gtttggtctc   2100
tctcaaagac atccatgact ttccaaccca agaaagcaag tcttcagcct ctcaccatat   2160
ccttggatga attgttctca tctagaggag aattcatctc tgtcggaggt aacggacgaa   2220
tgtctcataa agaggccatc ctgctcggtc tgaggtacaa aaagttgtac aatcaggcga   2280
gagtcaaata ttctctgtag actagtatga aaaaagtaa cagatatcac aatctaagtg   2340
ttatcccaat ccattcatca tgagttcctt aaagaagatt ctcggtctga aggggaaagg   2400
taagaaatct aagaaattag ggatcgcacc accccttat gaagaggaca ctaacatgga   2460
gtatgctccg agcgctccaa ttgacaaatc ctatttggga gttgacgaga tggacactca   2520
tgatccgaat caattaagat atgagaaatt cttctttaca gtgaaaatga cggttagatc   2580
taatcgtccg ttcagaacat actcagatgt ggcagccgct gtatcccatt gggatcacat   2640
gtacatcgga atggcaggga aacgtccctt ctacaagatc ttggctttt tgggttcttc   2700
taatctaaag gccactccag cggtattggc agatcaaggt caaccagagt atcatgctca   2760
ctgtgaaggc agggcttatt tgccacacag aatggggaag acccctccca tgctcaatgt   2820
accagagcac ttcagaagac cattcaatat aggtctttac aagggaacga ttgagctcac   2880
aatgaccatc tacgatgatg agtcactgga agcagctcct atgatctggg atcatttcaa   2940
ttcttccaaa ttttctgatt tcagagagaa ggccttaatg tttggcctga ttgtcgagaa   3000
aaaggcatct ggagcttggg tcctggattc tgtcagccac ttcaaatgag ctagtctagc   3060
ttccagcttc tgaacaatcc ccggtttact cagtctctcc taattccagc ctttcgaaca   3120
actaatatcc tgtcttctct atccctatga aaaaaactaa cagagatcga tctgtttcct   3180
tgacaccagg agccacc atg aag tgc ctt ttg tac tta gct ttt tta ttc      3230
                    Met Lys Cys Leu Leu Tyr Leu Ala Phe Leu Phe
                     1               5                  10
```

| | | | | | | | | | | | | | | | | |
|---|---|---|---|---|---|---|---|---|---|---|---|---|---|---|---|---|
| atc | ggg | gtg | aat | tgc | aag | gct | agc | gca | gag | aat | ttg | tgg | gta | aca | gtc | 3278 |
| Ile | Gly | Val | Asn | Cys | Lys | Ala | Ser | Ala | Glu | Asn | Leu | Trp | Val | Thr | Val | |
| | | | 15 | | | | 20 | | | | | 25 | | | | |
| tac | tat | gga | gtc | cct | gta | tgg | aag | gat | gca | gag | aca | aca | ttg | ttc | tgt | 3326 |
| Tyr | Tyr | Gly | Val | Pro | Val | Trp | Lys | Asp | Ala | Glu | Thr | Thr | Leu | Phe | Cys | |
| | | 30 | | | | | 35 | | | | | 40 | | | | |
| gct | agt | gac | gca | aag | gct | tac | gag | acg | gag | aag | cac | aat | gtg | tgg | gca | 3374 |
| Ala | Ser | Asp | Ala | Lys | Ala | Tyr | Glu | Thr | Glu | Lys | His | Asn | Val | Trp | Ala | |
| | 45 | | | | | 50 | | | | | 55 | | | | | |
| act | cac | gca | tgt | gtc | cca | acc | gat | cca | aat | cct | caa | gag | att | cat | cta | 3422 |
| Thr | His | Ala | Cys | Val | Pro | Thr | Asp | Pro | Asn | Pro | Gln | Glu | Ile | His | Leu | |
| 60 | | | | | 65 | | | | | 70 | | | | | 75 | |
| gag | aat | gtg | act | gaa | gaa | ttc | aat | atg | tgg | aag | aat | aat | atg | gta | gag | 3470 |
| Glu | Asn | Val | Thr | Glu | Glu | Phe | Asn | Met | Trp | Lys | Asn | Asn | Met | Val | Glu | |
| | | | | 80 | | | | | 85 | | | | | 90 | | |
| caa | atg | cat | aca | gat | atc | att | agt | tta | tgg | gac | cag | tca | ctt | aaa | ccc | 3518 |
| Gln | Met | His | Thr | Asp | Ile | Ile | Ser | Leu | Trp | Asp | Gln | Ser | Leu | Lys | Pro | |
| | | | 95 | | | | | 100 | | | | | 105 | | | |
| tgc | gtt | aaa | ttg | acg | cct | cta | tgt | gtg | aca | ctt | caa | tgt | act | aat | gtt | 3566 |
| Cys | Val | Lys | Leu | Thr | Pro | Leu | Cys | Val | Thr | Leu | Gln | Cys | Thr | Asn | Val | |
| | | 110 | | | | | 115 | | | | | 120 | | | | |
| aca | aac | aac | ata | aca | gat | gat | atg | aga | gga | gaa | ctg | aag | aac | tgt | agt | 3614 |
| Thr | Asn | Asn | Ile | Thr | Asp | Asp | Met | Arg | Gly | Glu | Leu | Lys | Asn | Cys | Ser | |
| | 125 | | | | | 130 | | | | | 135 | | | | | |
| ttc | aac | atg | acg | aca | gag | ttg | cgt | gac | aag | aaa | cag | aaa | gtg | tat | tca | 3662 |
| Phe | Asn | Met | Thr | Thr | Glu | Leu | Arg | Asp | Lys | Lys | Gln | Lys | Val | Tyr | Ser | |
| 140 | | | | | 145 | | | | | 150 | | | | | 155 | |
| cta | ttc | tat | cgg | ttg | gat | gta | gta | cag | ata | aat | gag | aat | caa | gga | aac | 3710 |
| Leu | Phe | Tyr | Arg | Leu | Asp | Val | Val | Gln | Ile | Asn | Glu | Asn | Gln | Gly | Asn | |
| | | | | 160 | | | | | 165 | | | | | 170 | | |
| agg | tcc | aac | aac | tct | aac | aaa | gag | tac | aga | ctt | att | aat | tgc | aat | acc | 3758 |
| Arg | Ser | Asn | Asn | Ser | Asn | Lys | Glu | Tyr | Arg | Leu | Ile | Asn | Cys | Asn | Thr | |
| | | | 175 | | | | | 180 | | | | | 185 | | | |
| agt | gct | atc | acg | caa | gcc | tgt | cca | aag | gtt | tca | ttt | gaa | cca | ata | cct | 3806 |
| Ser | Ala | Ile | Thr | Gln | Ala | Cys | Pro | Lys | Val | Ser | Phe | Glu | Pro | Ile | Pro | |
| | | 190 | | | | | 195 | | | | | 200 | | | | |
| att | cat | tat | tgt | gca | cct | gct | gga | ttc | gcc | atc | ctc | aaa | tgt | aaa | gac | 3854 |
| Ile | His | Tyr | Cys | Ala | Pro | Ala | Gly | Phe | Ala | Ile | Leu | Lys | Cys | Lys | Asp | |
| | 205 | | | | | 210 | | | | | 215 | | | | | |
| aag | aag | ttc | aat | gga | aca | gga | ccc | tgc | cca | tca | gtt | tca | acc | gtt | cag | 3902 |
| Lys | Lys | Phe | Asn | Gly | Thr | Gly | Pro | Cys | Pro | Ser | Val | Ser | Thr | Val | Gln | |
| 220 | | | | | 225 | | | | | 230 | | | | | 235 | |
| tgc | acc | cac | gga | atc | aag | cct | gta | gtt | agt | act | caa | tta | ttg | tta | aat | 3950 |
| Cys | Thr | His | Gly | Ile | Lys | Pro | Val | Val | Ser | Thr | Gln | Leu | Leu | Leu | Asn | |
| | | | | 240 | | | | | 245 | | | | | 250 | | |
| ggg | agc | tta | gct | gaa | gaa | gaa | gtt | atg | att | aga | tca | gag | aat | att | acc | 3998 |
| Gly | Ser | Leu | Ala | Glu | Glu | Glu | Val | Met | Ile | Arg | Ser | Glu | Asn | Ile | Thr | |
| | | | 255 | | | | | 260 | | | | | 265 | | | |
| aat | aat | gcg | aag | aac | atc | ttg | gtt | caa | ttc | aat | act | cca | gtc | cag | atc | 4046 |
| Asn | Asn | Ala | Lys | Asn | Ile | Leu | Val | Gln | Phe | Asn | Thr | Pro | Val | Gln | Ile | |
| | | 270 | | | | | 275 | | | | | 280 | | | | |
| aat | tgc | aca | agg | cct | aat | aat | aat | acc | aga | aag | agt | ata | aga | att | ggg | 4094 |
| Asn | Cys | Thr | Arg | Pro | Asn | Asn | Asn | Thr | Arg | Lys | Ser | Ile | Arg | Ile | Gly | |
| | 285 | | | | | 290 | | | | | 295 | | | | | |
| cca | gga | cag | gca | ttc | tat | gca | aca | gga | gat | ata | atc | gga | gac | att | cga | 4142 |
| Pro | Gly | Gln | Ala | Phe | Tyr | Ala | Thr | Gly | Asp | Ile | Ile | Gly | Asp | Ile | Arg | |
| 300 | | | | | 305 | | | | | 310 | | | | | 315 | |
| caa | gcg | cac | tgc | act | gtt | tct | aag | gcc | act | tgg | aat | gaa | aca | ttg | ggt | 4190 |
| Gln | Ala | His | Cys | Thr | Val | Ser | Lys | Ala | Thr | Trp | Asn | Glu | Thr | Leu | Gly | |

|  |  |  |  |  |  |  |  |  |  |  |  |  |  |  |  |
|---|---|---|---|---|---|---|---|---|---|---|---|---|---|---|---|
|  |  |  | 320 |  |  |  | 325 |  |  |  | 330 |  |  |  |  |
| aaa | gtt | gta | aag | caa | ctt | cgg | aag | cat | ttc | gga | aat | aac | aca | att | att | 4238 |
| Lys | Val | Val | Lys | Gln | Leu | Arg | Lys | His | Phe | Gly | Asn | Asn | Thr | Ile | Ile |  |
|  |  |  | 335 |  |  |  | 340 |  |  |  | 345 |  |  |  |  |
| aga | ttt | gcg | aac | tca | tct | gga | ggg | gat | ctg | gaa | gtg | aca | aca | cac | tct | 4286 |
| Arg | Phe | Ala | Asn | Ser | Ser | Gly | Gly | Asp | Leu | Glu | Val | Thr | Thr | His | Ser |  |
|  |  | 350 |  |  |  |  | 355 |  |  |  |  | 360 |  |  |  |
| ttc | aat | tgc | ggt | ggc | gag | ttc | ttc | tat | tgt | aat | aca | agt | gga | tta | ttt | 4334 |
| Phe | Asn | Cys | Gly | Gly | Glu | Phe | Phe | Tyr | Cys | Asn | Thr | Ser | Gly | Leu | Phe |  |
| 365 |  |  |  |  | 370 |  |  |  |  | 375 |  |  |  |  |  |
| aac | tct | act | tgg | att | tca | aat | acc | tca | gtc | caa | gga | tct | aat | tca | aca | 4382 |
| Asn | Ser | Thr | Trp | Ile | Ser | Asn | Thr | Ser | Val | Gln | Gly | Ser | Asn | Ser | Thr |  |
| 380 |  |  |  | 385 |  |  |  |  | 390 |  |  |  |  | 395 |  |
| ggg | tct | aac | gat | tct | ata | aca | tta | cct | tgc | cgt | ata | aag | caa | att | att | 4430 |
| Gly | Ser | Asn | Asp | Ser | Ile | Thr | Leu | Pro | Cys | Arg | Ile | Lys | Gln | Ile | Ile |  |
|  |  |  |  | 400 |  |  |  |  | 405 |  |  |  |  | 410 |  |
| aat | atg | tgg | caa | aga | atc | ggg | caa | gcg | atg | tat | gct | cca | cct | att | caa | 4478 |
| Asn | Met | Trp | Gln | Arg | Ile | Gly | Gln | Ala | Met | Tyr | Ala | Pro | Pro | Ile | Gln |  |
|  |  |  | 415 |  |  |  | 420 |  |  |  | 425 |  |  |  |  |
| ggc | gtg | att | cgt | tgc | gtt | tca | aac | ata | aca | ggg | ttg | atc | ctg | acc | agg | 4526 |
| Gly | Val | Ile | Arg | Cys | Val | Ser | Asn | Ile | Thr | Gly | Leu | Ile | Leu | Thr | Arg |  |
|  |  | 430 |  |  |  |  | 435 |  |  |  |  | 440 |  |  |  |
| gat | gga | ggc | tct | acc | aat | tcc | acc | acc | gag | acc | ttc | cgt | ccc | ggt | ggc | 4574 |
| Asp | Gly | Gly | Ser | Thr | Asn | Ser | Thr | Thr | Glu | Thr | Phe | Arg | Pro | Gly | Gly |  |
| 445 |  |  |  |  | 450 |  |  |  |  | 455 |  |  |  |  |  |
| gga | gat | atg | cgg | gat | aac | tgg | aga | tca | gag | ctc | tat | aag | tat | aag | gtt | 4622 |
| Gly | Asp | Met | Arg | Asp | Asn | Trp | Arg | Ser | Glu | Leu | Tyr | Lys | Tyr | Lys | Val |  |
| 460 |  |  |  | 465 |  |  |  |  | 470 |  |  |  |  | 475 |  |
| gtg | aag | att | gaa | cct | ctt | gga | gtt | gcc | cct | aca | aga | gca | aag | aga | agg | 4670 |
| Val | Lys | Ile | Glu | Pro | Leu | Gly | Val | Ala | Pro | Thr | Arg | Ala | Lys | Arg | Arg |  |
|  |  |  |  | 480 |  |  |  |  | 485 |  |  |  |  | 490 |  |
| gtg | gtt | ggc | cga | gag | aag | aga | gca | gtt | ggc | atc | ggt | gct | gtc | ttt | ctc | 4718 |
| Val | Val | Gly | Arg | Glu | Lys | Arg | Ala | Val | Gly | Ile | Gly | Ala | Val | Phe | Leu |  |
|  |  |  | 495 |  |  |  | 500 |  |  |  | 505 |  |  |  |  |
| gga | ttt | ctt | gga | gca | gct | gga | tcc | act | atg | gga | gca | gca | tca | atg | aca | 4766 |
| Gly | Phe | Leu | Gly | Ala | Ala | Gly | Ser | Thr | Met | Gly | Ala | Ala | Ser | Met | Thr |  |
|  |  | 510 |  |  |  |  | 515 |  |  |  |  | 520 |  |  |  |
| cta | aca | gtg | cag | gct | aga | aat | ttg | ctt | agc | gga | atc | gtt | cag | cag | cag | 4814 |
| Leu | Thr | Val | Gln | Ala | Arg | Asn | Leu | Leu | Ser | Gly | Ile | Val | Gln | Gln | Gln |  |
|  | 525 |  |  |  |  | 530 |  |  |  |  | 535 |  |  |  |  |
| agc | aat | tta | cta | aga | gca | att | gaa | gca | cag | caa | cat | ctc | tta | aag | ttg | 4862 |
| Ser | Asn | Leu | Leu | Arg | Ala | Ile | Glu | Ala | Gln | Gln | His | Leu | Leu | Lys | Leu |  |
| 540 |  |  |  | 545 |  |  |  |  | 550 |  |  |  |  | 555 |  |
| acg | gtg | tgg | ggc | att | aaa | caa | cta | caa | gcg | aga | gtg | ctt | gcc | gtc | gaa | 4910 |
| Thr | Val | Trp | Gly | Ile | Lys | Gln | Leu | Gln | Ala | Arg | Val | Leu | Ala | Val | Glu |  |
|  |  |  | 560 |  |  |  | 565 |  |  |  | 570 |  |  |  |  |
| aga | tat | ttg | cga | gac | caa | cag | cta | ttg | ggt | att | tgg | ggt | tgt | tct | ggg | 4958 |
| Arg | Tyr | Leu | Arg | Asp | Gln | Gln | Leu | Leu | Gly | Ile | Trp | Gly | Cys | Ser | Gly |  |
|  |  | 575 |  |  |  |  | 580 |  |  |  |  | 585 |  |  |  |
| aaa | tta | att | tgc | aca | aca | aat | gtt | cca | tgg | aac | tcc | tcc | tgg | agt | aat | 5006 |
| Lys | Leu | Ile | Cys | Thr | Thr | Asn | Val | Pro | Trp | Asn | Ser | Ser | Trp | Ser | Asn |  |
| 590 |  |  |  |  | 595 |  |  |  |  | 600 |  |  |  |  |  |
| agg | aat | tta | agt | gag | ata | tgg | gac | aac | atg | aca | tgg | ttg | cag | tgg | gac | 5054 |
| Arg | Asn | Leu | Ser | Glu | Ile | Trp | Asp | Asn | Met | Thr | Trp | Leu | Gln | Trp | Asp |  |
| 605 |  |  |  |  | 610 |  |  |  |  | 615 |  |  |  |  |  |
| aag | gaa | atc | tca | aat | tat | aca | cag | ata | atc | tat | gga | tta | tta | gaa | gag | 5102 |
| Lys | Glu | Ile | Ser | Asn | Tyr | Thr | Gln | Ile | Ile | Tyr | Gly | Leu | Leu | Glu | Glu |  |
| 620 |  |  |  |  | 625 |  |  |  |  | 630 |  |  |  |  | 635 |
| tct | cag | aat | cag | caa | gag | aag | aat | gaa | cag | gat | ttg | ctt | gca | ttg | gat | 5150 |

```
Ser Gln Asn Gln Gln Glu Lys Asn Glu Gln Asp Leu Leu Ala Leu Asp
                640                 645                 650 aag tgg gct tct cta tgg aac tgg ttc gat att agt aat tgg ctc tgg      5198
Lys Trp Ala Ser Leu Trp Asn Trp Phe Asp Ile Ser Asn Trp Leu Trp
            655                 660                 665 tat att aag agc tct att gcc tct ttt ttc ttt atc ata ggg tta atc      5246
Tyr Ile Lys Ser Ser Ile Ala Ser Phe Phe Phe Ile Ile Gly Leu Ile
            670                 675                 680 att gga cta ttc ttg gtt ctc cga gtt ggt att tat ctt tgc att aaa      5294
Ile Gly Leu Phe Leu Val Leu Arg Val Gly Ile Tyr Leu Cys Ile Lys
            685                 690                 695 tta aag cac acc aag aaa aga cag att tat aca gac ata gag atg aac      5342
Leu Lys His Thr Lys Lys Arg Gln Ile Tyr Thr Asp Ile Glu Met Asn
700                 705                 710                 715 cga ctt gga aag taaagctcaa atcctgcaca acagattctt catgtttgaa          5394
Arg Leu Gly Lys ccaaatcaac ttgtgatatc atgctcaaag aggccttaat taaattttaa tttttaattt    5454
ttatgaaaaa aactaacagc aatcatggaa gtccacgatt ttgagaccga cgagttcaat    5514
gatttcaatg aagatgacta tgccacaaga gaattcctga atcccgatga gcgcatgacg    5574
tacttgaatc atgctgatta caatttgaat tctcctctaa ttagtgatga tattgacaat    5634
ttgatcagga aattcaattc tcttccgatt ccctcgatgt gggatagtaa gaactgggat    5694
ggagttcttg agatgttaac atcatgtcaa gccaatccca tctcaacatc tcagatgcat    5754
aaatggatgg gaagttggtt aatgtctgat aatcatgatg ccagtcaagg gtatagtttt    5814
ttacatgaag tggacaaaga ggcagaaata acatttgacg tggtggagac cttcatccgc    5874
ggctggggca acaaaccaat tgaatacatc aaaaaggaaa gatggactga ctcattcaaa    5934
attctcgctt atttgtgtca aaagtttttg gacttacaca agttgacatt aatcttaaat    5994
gctgtctctg aggtggaatt gctcaacttg gcgaggactt tcaaaggcaa agtcagaaga    6054
agttctcatg aacgaacat atgcaggctt agggttccca gcttgggtcc tactttatt      6114 tcagaaggat gggcttactt caagaaactt gatattctaa tggaccgaaa ctttctgtta    6174
atggtcaaag atgtgattat agggaggatg caaacggtgc tatccatggt atgtagaata    6234
gacaacctgt tctcagagca agacatcttc tcccttctaa atatctacag aattggagat    6294
aaaattgtgg agaggcaggg aaattttttct tatgacttga ttaaaatggt ggaaccgata   6354
tgcaacttga agctgatgaa attagcaaga gaatcaaggc ctttagtccc acaattccct    6414
cattttgaaa atcatatcaa gacttctgtt gatgaagggg caaaaattga ccgaggtata    6474
agattcctcc atgatcagat aatgagtgtg aaaacagtgg atctcacact ggtgatttat    6534
ggatcgttca gacattgggg tcatcctttt atagattatt acgctggact agaaaaatta    6594
cattcccaag taaccatgaa gaaagatatt gatgtgtcat atgcaaaagc acttgcaagt    6654
gatttagctc ggattgttct atttcaacag ttcaatgatc ataaaaagtg gttcgtgaat    6714
ggagacttgc tccctcatga tcatcccttt aaaagtcatg ttaaagaaaa tacatggcct    6774
acagctgctc aagttcaaga ttttggagat aaatggcatg aacttccgct gattaaatgt    6834
tttgaaatac ccgacttact agacccatcg ataatatact ctgacaaaag tcattcaatg    6894
aataggtcag aggtgttgaa acatgtccga atgaatccga acactcctat ccctagtaaa    6954
aaggtgttgc agactatgtt ggacacaaag gctaccaatt ggaaagaatt tcttaaagag    7014
attgatgaga agggcttaga tgatgatgat ctaattattg gtcttaaagg aaaggagagg    7074
gaactgaagt tggcaggtag attttttctcc ctaatgtctt ggaaattgcg agaatacttt    7134
```

```
gtaattaccg aatatttgat aaagactcat ttcgtccctg tgtttaaagg cctgacaatg   7194
gcggacgatc taactgcagt cattaaaaag atgttagatt cctcatccgg ccaaggattg   7254
aagtcatatg aggcaatttg catagccaat cacattgatt acgaaaaatg gaataaccac   7314
caaaggaagt tatcaaacgg cccagtgttc cgagttatgg gccagttctt aggttatcca   7374
tccttaatcg agagaactca tgaattttt gagaaaagtc ttatatacta caatggaaga    7434
ccagacttga tgcgtgttca caacaacaca ctgatcaatt caacctccca acgagtttgt   7494
tggcaaggac aagagggtgg actggaaggt ctacggcaaa aaggatggag tatcctcaat   7554
ctactggtta ttcaaagaga ggctaaaatc agaaacactg ctgtcaaagt cttggcacaa   7614
ggtgataatc aagttatttg cacacagtat aaaacgaaga aatcgagaaa cgttgtagaa   7674
ttacagggtc ctctcaatca aatggtttct aataatgaga aaattatgac tgcaatcaaa   7734
atagggacag ggaagttagg acttttgata aatgacgatg agactatgca atctgcagat   7794
tacttgaatt atggaaaaat accgattttc cgtggagtga ttagagggtt agagaccaag   7854
agatggtcac gagtgacttg tgtcaccaat gaccaaatac ccacttgtgc taatataatg   7914
agctcagttt ccacaaatgc tctcaccgta gctcattttg ctgagaaccc aatcaatgcc   7974
atgatacagt acaattattt tgggacattt gctagactct tgttgatgat gcatgatcct   8034
gctcttcgtc aatcattgta tgaagttcaa gataagatac cgggcttgca cagttctact   8094
ttcaaatacg ccatgttgta tttggaccct tccattggag gagtgtcggg catgtctttg   8154
tccaggtttt tgattagagc cttcccagat cccgtaacag aaagtctctc attctggaga   8214
ttcatccatg tacatgctcg aagtgagcat ctgaaggaga tgagtgcagt atttggaaac   8274
cccgagatag ccaagttccg aataactcac atagacaagc tagtagaaga tccaacctct   8334
ctgaacatcg ctatgggaat gagtccagcg aacttgttaa agactgaggt taaaaaatgc   8394
ttaatcgaat caagacaaac catcaggaac caggtgatta aggatgcaac catatatttg   8454
tatcatgaag aggatcggct cagaagtttc ttatggtcaa taaatcctct gttccctaga   8514
tttttaagtg aattcaaatc aggcactttt tggggagtcg cagacggct catcagtcta    8574 tttcaaaatt ctcgtactat tcggaactcc tttaagaaaa agtatcatag ggaattggat   8634
gatttgattg tgaggagtga ggtatcctct ttgacacatt tagggaaact tcatttgaga   8694
aggggatcat gtaaaatgtg gacatgttca gctactcatg ctgacacatt aagatacaaa   8754
tcctggggcc gtacagttat tgggacaact gtaccccatc cattagaaat gttgggtcca   8814
caacatcgaa aagagactcc ttgtgcacca tgtaacacat cagggttcaa ttatgtttct   8874
gtgcattgtc cagacgggat ccatgacgtc tttagttcac ggggaccatt gcctgcttat   8934
ctagggtcta aacatctgaa tctacatctc attttgcagc cttgggaaag ggaaagcaaa   8994
gtcccactga ttaaaagagc tacacgtctt agagatgcta tctcttggtt tgttgaaccc   9054
gactctaaac tagcaatgac tatactttct aacatccact ctttaacagg cgaagaatgg   9114
accaaaaggc agcatgggtt caaaagaaca gggtctgccc ttcataggtt ttcgacatct   9174
cggatgagcc atggtgggtt cgcatctcag agcactgcag cattgaccag gttgatggca   9234
actacagaca ccatgaggga tctgggagat cagaatttcg actttttatt ccaagcaacg   9294
ttgctctatg ctcaaattac caccactgtt gcaagagacg gatggatcac cagttgtaca   9354
gatcattatc atattgcctg taagtcctgt ttgagaccca tagaagagat caccctggac   9414
tcaagtatgg actacacgcc cccagatgta tcccatgtgc tgaagacatg gaggaatggg   9474
```

```
gaaggttcgt ggggacaaga gataaaacag atctatcctt tagaagggaa ttggaagaat    9534
ttagcacctg ctgagcaatc ctatcaagtc ggcagatgta taggttttct atatggagac    9594
ttggcgtata gaaaatctac tcatgccgag gacagttctc tatttcctct atctatacaa    9654
ggtcgtatta gaggtcgagg tttcttaaaa gggttgctag acggattaat gagagcaagt    9714
tgctgccaag taatacaccg gagaagtctg gctcatttga agaggccggc caacgcagtg    9774
tacggaggtt tgatttactt gattgataaa ttgagtgtat cacctccatt cctttctctt    9834
actagatcag gacctattag agacgaatta gaaacgattc cccacaagat cccaacctcc    9894
tatccgacaa gcaaccgtga tatgggggtg attgtcagaa attacttcaa ataccaatgc    9954
cgtctaattg aaaagggaaa atacagatca cattattcac aattatggtt attctcagat   10014
gtcttatcca tagacttcat tggaccattc tctatttcca ccaccctctt gcaaatccta   10074
tacaagccat ttttatctgg gaaagataag aatgagttga gagagctggc aaatctttct   10134
tcattgctaa gatcaggaga ggggtgggaa gacatacatg tgaaattctt caccaaggac   10194
atattattgt gtccagagga aatcagacat gcttgcaagt tcgggattgc taaggataat   10254
aataaagaca tgagctatcc cccttgggga agggaatcca gagggacaat tacaacaatc   10314
cctgtttatt atacgaccac cccttaccca aagatgctag agatgcctcc aagaatccaa   10374
aatcccctgc tgtccggaat caggttgggc caattaccaa ctggcgctca ttataaaatt   10434
cggagtatat tacatggaat gggaatccat tacagggact tcttgagttg tggagacggc   10494
tccggaggga tgactgctgc attactacga gaaaatgtgc atagcagagg aatattcaat   10554
agtctgttag aattatcagg gtcagtcatg cgaggcgcct ctcctgagcc ccccagtgcc   10614
ctagaaactt taggaggaga taaatcgaga tgtgtaaatg gtgaaacatg ttgggaatat   10674
ccatctgact tatgtgaccc aaggacttgg gactatttcc tccgactcaa agcaggcttg   10734
gggcttcaaa ttgatttaat tgtaatggat atggaagttc gggattcttc tactagcctg   10794
aaaattgaga cgaatgttag aaattatgtg caccggattt tggatgagca aggagttta   10854 atctacaaga cttatggaac atatatttgt gagagcgaaa agaatgcagt aacaatcctt   10914
ggtcccatgt tcaagacggt cgacttagtt caaacagaat ttagtagttc tcaaacgtct   10974
gaagtatata tggtatgtaa aggtttgaag aaattaatcg atgaacccaa tcccgattgg   11034
tcttccatca atgaatcctg gaaaaacctg tacgcattcc agtcatcaga acaggaattt   11094
gccagagcaa agaaggttag tacatacttt accttgacag gtattccctc ccaattcatt   11154
cctgatcctt ttgtaaacat tgagactatg ctacaaatat tcggagtacc cacgggtgtg   11214
tctcatgcgg ctgccttaaa atcatctgat agacctgcag atttattgac cattagcctt   11274
ttttatatgg cgattatatc gtattataac atcaatcata tcagagtagg accgatacct   11334
ccgaaccccc catcagatgg aattgcacaa aatgtgggga tcgctataac tggtataagc   11394
ttttggctga gtttgatgga gaaagacatt ccactatatc aacagtgttt agcagttatc   11454
cagcaatcat tcccgattag gtgggaggct gtttcagtaa aaggaggata caagcagaag   11514
tggagtacta gaggtgatgg gctcccaaaa gatacccgaa tttcagactc cttggcccca   11574
atcgggaact ggatcagatc tctggaattg gtccgaaacc aagttcgtct aaatccattc   11634
aatgagatct tgttcaatca gctatgtcgt acagtggata tcatttgaa atggtcaaat   11694 ttgcgaaaaa acacaggaat gattgaatgg atcaatagac gaatttcaaa agaagaccgg   11754
tctatactga tgttgaagag tgacctacac gaggaaaact cttggagaga ttaaaaaatc   11814
atgaggagac tccaaacttt aagtatgaaa aaaactttga tccttaagac cctcttgtgg   11874
```

```
tttttatttt ttatctggtt ttgtggtctt cgtggccggc atggtcccag cctcctcgct   11934
ggcgccggct gggcaacatt ccgaggggac cgtcccctcg gtaatggcga atgggacctg   11994
ctaacaaagc ccgaaaggaa gctgagttgg ctgctgccac cgctgagcaa taactagcat   12054
aaccccttgg ggcctctaaa cgggtcttga ggggttttt gctgaaagga ggaactatat   12114
ccggatgcgg ccgatccggc tgctaacaaa gcccgaaagg aagctgagtt ggctgctgcc   12174
accgctgagc aataactagc ataacccctt ggggcctcta acgggtctt gaggggtttt   12234 ttgctgaaag gaggaactat atccgggtta acctgcatta atgaatcggc caacgcgcgg   12294
ggagaggcgg tttgcgtatt gggcgctctt ccgcttcctc gctcactgac tcgctgcgct   12354
cggtcgttcg gctgcggcga gcggtatcag ctcactcaaa ggcggtaata cggttatcca   12414
cagaatcagg ggataacgca ggaaagaaca tgtgagcaaa aggccagcaa aaggccagga   12474
accgtaaaaa ggccgcgttg ctggcgtttt tccataggct ccgcccccct gacgagcatc   12534
acaaaaatcg acgctcaagt cagaggtggc gaaacccgac aggactataa agataccagg   12594
cgtttccccc tggaagctcc ctcgtgcgct ctcctgttcc gaccctgccg cttaccggat   12654
acctgtccgc ctttctccct tcgggaagcg tggcgctttc tcaatgctca cgctgtaggt   12714
atctcagttc ggtgtaggtc gttcgctcca agctgggctg tgtgcacgaa ccccccgttc   12774
agcccgaccg ctgcgcctta tccggtaact atcgtcttga gtccaacccg gtaagacacg   12834
acttatcgcc actggcagca gccactggta acaggattag cagagcgagg tatgtaggcg   12894
gtgctacaga gttcttgaag tggtggccta actacggcta cactagaagg acagtatttg   12954
gtatctgcgc tctgctgaag ccagttacct tcggaaaaag agttggtagc tcttgatccg   13014
gcaaacaaac caccgctggt agcggtggtt tttttgtttg caagcagcag attacgcgca   13074
gaaaaaaagg atctcaagaa gatcctttga tcttttctac ggggtctgac gctcagtgga   13134
acgaaaactc acgttaaggg attttggtca tgagattatc aaaaaggatc ttcacctaga   13194
tccttttaaa ttaaaaatga agttttaaat caatctaaag tatatatgag taaacttggt   13254
ctgacagtta ccaatgctta atcagtgagg cacctatctc agcgatctgt ctatttcgtt   13314
catccatagt tgcctgactc cccgtcgtgt agataactac gatacgggag ggcttaccat   13374
ctggccccag tgctgcaatg ataccgcgag acccacgctc accggctcca gatttatcag   13434
caataaacca gccagccgga agggccgagc gcagaagtgg tcctgcaact ttatccgcct   13494
ccatccagtc tattaattgt tgccgggaag ctagagtaag tagttcgcca gttaatagtt   13554
tgcgcaacgt tgttgccatt gctacaggca tcgtggtgtc acgctcgtcg tttggtatgg   13614
cttcattcag ctccggttcc caacgatcaa ggcgagttac atgatccccc atgttgtgca   13674
aaaaagcggt tagctccttc ggtcctccga tcgttgtcag aagtaagttg gccgcagtgt   13734
tatcactcat ggttatggca gcactgcata attctcttac tgtcatgcca tccgtaagat   13794
gcttttctgt gactggtgag tactcaacca agtcattctg agaatagtgt atgcggcgac   13854
cgagttgctc ttgcccggcg tcaatacggg ataataccgc gccacatagc agaactttaa   13914
aagtgctcat cattggaaaa cgttcttcgg ggcgaaaact ctcaaggatc ttaccgctgt   13974
tgagatccag ttcgatgtaa cccactcgtg cacccaactg atcttcagca tcttttactt   14034
tcaccagcgt ttctgggtga gcaaaaacag gaaggcaaaa tgccgcaaaa aagggaataa   14094
gggcgacacg gaaatgttga atactcatac tcttcctttt tcaatattat tgaagcattt   14154
atcagggtta ttgtctcatg agcggataca tatttgaatg tatttagaaa aataaacaaa   14214
```

-continued

```
tagggggttcc gcgcacattt ccccgaaaag tgccacctga cgtc                      14258
```

<210> SEQ ID NO 2
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Lys Cys Leu Leu Tyr Leu Ala Phe Leu Phe Ile Gly Val Asn Cys
1               5                   10                  15

Lys Ala Ser Ala Glu Asn Leu Trp Val Thr Val Tyr Tyr Gly Val Pro
            20                  25                  30

Val Trp Lys Asp Ala Glu Thr Thr Leu Phe Cys Ala Ser Asp Ala Lys
        35                  40                  45

Ala Tyr Glu Thr Glu Lys His Asn Val Trp Ala Thr His Ala Cys Val
    50                  55                  60

Pro Thr Asp Pro Asn Pro Gln Glu Ile His Leu Glu Asn Val Thr Glu
65                  70                  75                  80

Glu Phe Asn Met Trp Lys Asn Asn Met Val Glu Gln Met His Thr Asp
                85                  90                  95

Ile Ile Ser Leu Trp Asp Gln Ser Leu Lys Pro Cys Val Lys Leu Thr
            100                 105                 110

Pro Leu Cys Val Thr Leu Gln Cys Thr Asn Val Thr Asn Asn Ile Thr
        115                 120                 125

Asp Asp Met Arg Gly Glu Leu Lys Asn Cys Ser Phe Asn Met Thr Thr
    130                 135                 140

Glu Leu Arg Asp Lys Lys Gln Lys Val Tyr Ser Leu Phe Tyr Arg Leu
145                 150                 155                 160

Asp Val Val Gln Ile Asn Glu Asn Gln Gly Asn Arg Ser Asn Asn Ser
                165                 170                 175

Asn Lys Glu Tyr Arg Leu Ile Asn Cys Asn Thr Ser Ala Ile Thr Gln
            180                 185                 190

Ala Cys Pro Lys Val Ser Phe Glu Pro Ile Pro Ile His Tyr Cys Ala
        195                 200                 205

Pro Ala Gly Phe Ala Ile Leu Lys Cys Lys Asp Lys Lys Phe Asn Gly
    210                 215                 220

Thr Gly Pro Cys Pro Ser Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Val Met Ile Arg Ser Glu Asn Ile Thr Asn Asn Ala Lys Asn
            260                 265                 270

Ile Leu Val Gln Phe Asn Thr Pro Val Gln Ile Asn Cys Thr Arg Pro
        275                 280                 285

Asn Asn Asn Thr Arg Lys Ser Ile Arg Ile Gly Pro Gly Gln Ala Phe
    290                 295                 300

Tyr Ala Thr Gly Asp Ile Ile Gly Asp Ile Arg Gln Ala His Cys Thr
305                 310                 315                 320

Val Ser Lys Ala Thr Trp Asn Glu Thr Leu Gly Lys Val Val Lys Gln
                325                 330                 335

Leu Arg Lys His Phe Gly Asn Asn Thr Ile Ile Arg Phe Ala Asn Ser
            340                 345                 350
```

Ser Gly Gly Asp Leu Glu Val Thr Thr His Ser Phe Asn Cys Gly
355                 360                 365

Glu Phe Phe Tyr Cys Asn Thr Ser Gly Leu Phe Asn Ser Thr Trp Ile
370                 375                 380

Ser Asn Thr Ser Val Gln Gly Ser Asn Ser Thr Gly Ser Asn Asp Ser
385                 390                 395                 400

Ile Thr Leu Pro Cys Arg Ile Lys Gln Ile Ile Asn Met Trp Gln Arg
            405                 410                 415

Ile Gly Gln Ala Met Tyr Ala Pro Pro Ile Gln Gly Val Ile Arg Cys
                420                 425                 430

Val Ser Asn Ile Thr Gly Leu Ile Leu Thr Arg Asp Gly Gly Ser Thr
        435                 440                 445

Asn Ser Thr Thr Glu Thr Phe Arg Pro Gly Gly Gly Asp Met Arg Asp
    450                 455                 460

Asn Trp Arg Ser Glu Leu Tyr Lys Tyr Lys Val Val Lys Ile Glu Pro
465                 470                 475                 480

Leu Gly Val Ala Pro Thr Arg Ala Lys Arg Arg Val Val Gly Arg Glu
                485                 490                 495

Lys Arg Ala Val Gly Ile Gly Ala Val Phe Leu Gly Phe Leu Gly Ala
            500                 505                 510

Ala Gly Ser Thr Met Gly Ala Ala Ser Met Thr Leu Thr Val Gln Ala
        515                 520                 525

Arg Asn Leu Leu Ser Gly Ile Val Gln Gln Gln Ser Asn Leu Leu Arg
    530                 535                 540

Ala Ile Glu Ala Gln Gln His Leu Leu Lys Leu Thr Val Trp Gly Ile
545                 550                 555                 560

Lys Gln Leu Gln Ala Arg Val Leu Ala Val Glu Arg Tyr Leu Arg Asp
                565                 570                 575

Gln Gln Leu Leu Gly Ile Trp Gly Cys Ser Gly Lys Leu Ile Cys Thr
            580                 585                 590

Thr Asn Val Pro Trp Asn Ser Ser Trp Ser Asn Arg Asn Leu Ser Glu
        595                 600                 605

Ile Trp Asp Asn Met Thr Trp Leu Gln Trp Asp Lys Glu Ile Ser Asn
    610                 615                 620

Tyr Thr Gln Ile Ile Tyr Gly Leu Leu Glu Glu Ser Gln Asn Gln Gln
625                 630                 635                 640

Glu Lys Asn Glu Gln Asp Leu Leu Ala Leu Asp Lys Trp Ala Ser Leu
                645                 650                 655

Trp Asn Trp Phe Asp Ile Ser Asn Trp Leu Trp Tyr Ile Lys Ser Ser
            660                 665                 670

Ile Ala Ser Phe Phe Phe Ile Ile Gly Leu Ile Gly Leu Phe Leu
        675                 680                 685

Val Leu Arg Val Gly Ile Tyr Leu Cys Ile Lys Leu Lys His Thr Lys
    690                 695                 700

Lys Arg Gln Ile Tyr Thr Asp Ile Glu Met Asn Arg Leu Gly Lys
705                 710                 715

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
cactagrtgt ctctgcacta tytgttt                                          27

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtctgcgtca tytggtgcat                                                  20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cttcytcagt rtgtttca                                                    18

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Ser
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His His His
1               5
```

REPLICATION-COMPETENT VSV-HIV ENV VACCINES

INCORPORATION BY REFERENCE

This application claims benefit of and priority to U.S. provisional patent application Ser. No. 62/236,448 filed Oct. 2, 2015.

Reference is made to U.S. patent application Ser. No. 13/792,106 filed Mar. 10, 2013 which claims priority to U.S. provisional patent application Ser. No. 61/614,584 filed Mar. 23, 2012. Reference is made to U.S. patent application Ser. No. 12/708,940 filed Feb. 19, 2010, U.S. provisional patent application Ser. Nos. 61/537,497 filed Sep. 21, 2011; 61/552,240 filed Oct. 27, 2011 and 61/617,368 filed Mar. 29, 2012.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted electronically in ASCII format and is hereby incorporated by reference in its entirety. Said ASCII copy, created on Nov. 9, 2016, is named 43094_01_2039_SL.txt and is 34,098 bytes in size.

FIELD OF THE INVENTION

The present invention relates to recombinant vesicular stomatitis virus for use as prophylactic and therapeutic vaccines for infectious diseases of AIDS.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4$^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4$^+$ T-lymphocytes, which are critical to immune defense, is a major cause of the progressive immune dysfunction that is the hallmark of AIDS disease progression. The loss of CD4$^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

There remains a need to express immunogens that elicit broadly neutralizing antibodies. Strategies include producing molecules that mimic the mature trimer on the virion surface, producing Env molecules engineered to better present neutralizing antibody epitopes than wild-type molecules, generating stable intermediates of the entry process to expose conserved epitopes to which antibodies could gain access during entry and producing epitope mimics of the broadly neutralizing monoclonal antibodies determined from structural studies of the antibody-antigen complexes (Burton et al., Nat Immunol. 2004 March; 5(3):233-6). However, none of these approaches have yet efficiently elicited neutralizing antibodies with broad specificity.

Citation or identification of any document in this application is not an admission that such document is available as prior art to the present application.

SUMMARY OF THE INVENTION

To develop an HIV vaccine that could mimic the efficacy of live attenuated viral vaccines, a replication-competent chimeric virus (VSVΔG-Env.BG505) was developed from vesicular stomatitis virus (VSV) by replacing the G gene, which encodes the VSV glycoprotein, with sequence encoding functional clade A HIV Env.BG505. The Env-dependent chimeric virus expresses Env.BG505 abundantly during propagation in CD4+/CCR5+ cells, which generates infected cells and progeny virus particles with Env presented on their surface that is recognized by trimer-specific broadly neutralizing antibodies.

A study was initiated in Indian rhesus macaques to address safety, immunogenicity and efficacy of the VSVΔG-Env.BG505 vaccine candidate. Groups of 10 macaques (negative for Mamu-B*08 and -B*17 MHC alleles) were vaccinated at weeks 0, 4, and 29 by mucosal administration to both the nasal and oral cavities with $1 \times 10^8$ plaque-forming units (pfus) of VSVΔG-Env.BG505 at each site or a saline control. Five months after the last immunization monkeys were challenged by intrarectal exposure with heterologous SHIV 162P3 ($2 \times 10^4$ TCID50 per challenge) every 2 weeks for 10 weeks, after which they were rested for 6 weeks before challenge continued with an additional 5 bi-weekly exposures.

The invention relates to a recombinant vesicular stomatitis virus (VSV) vector wherein the gene encoding the VSV surface glycoprotein G (VSV G) may be functionally replaced by a functional clade A HIV Env BG505. Clade B, Clade C and/or Clade E Env counterparts are also contemplated in addition to other Clade A counterparts. The HIV Env may be recognized by antibodies PG9, PG16, 2G12, b12, 2F5, 4E10 or Z13 or other antibodies, including potent broadly neutralizing trimer-specific antibodies. VSV is a minus-strand RNA virus that can infect insects and mammals.

The present invention also encompasses methods of producing or eliciting an immune response, which may comprise administering to a mammal any one of the herein disclosed recombinant VSV vectors.

The present invention also encompasses other plus and minus strand viruses which may be used as recombinant viral vectors in the method of the invention. Such viruses include but are not limited to: Measles virus, Canine distemper virus, Parainfluenza viruses, Sendai virus, Newcastle disease virus, Venezuelan equine encephalitis virus, Sindbis virus, Semliki Forrest virus etc.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIGS. 1A-1C. Recombinant VSVΔG-Env. A) A linear map of the VSV genome, which contains 5 gene regions encoding the Nucleocapsid protein (N), the Phosphoprotein (P) RNA-dependent RNA polymerase subunit, Matrix protein (M), Glycoprotein (G), and the catalytic subunit of the polymerase (Large protein or L). The 11-kb RNA genome is single-stranded, nonsegmented, and negative-sense. A single promoter at the 3' end controls mRNA synthesis. Transcription initiated at the 3' end terminates and reinitiates at each gene boundary. Because reinitiation is not 100% efficient, gene regions distal to the promoter are transcribed less efficiently generating a protein expression gradient. Changing the gene order, particularly when N is placed downstream, attenuates virus replication. A schematic of the VSV particle is show next to the genome map. B) Genome of the VSVΔG-Env.BG505 chimera in which the G gene is replaced with sequence encoding HIV Env.BG505. C) Map of the VSVΔG-Env genomic clone. The VSV (Indiana serotype) genomic sequence was derived from a lab-adapted virus. The Env.BG505 gene sequence is optimized to reflect VSV codon usage and relatively A+T-rich nucleotide content. To support rescue of recombinant virus, the T7 bacteriophage promoter is positioned to transcribe a positive-sense genome copy precursor and subsequent cleavage by cis-acting ribozymes generate precise termini.

FIG. 9. Monitoring SHIV genome copies in the blood of infected animals. SHIV genome copies in blood samples were quantified by real-time quantitative PCR (RT-qPCR). Genome copies per ml of plasma are plotted from the time infection was first detected by a qPCR signal of ≥200 genome copies per ml. Animal identifiers are located to the right of the graphs. Bold indicates infected animals through the 10th challenge.

FIG. 12. Generation of VSVΔG-Env.BG505 from DNA and summary of steps to produce a seed virus for use in vaccine manufacturing.

FIG. 13. Preparation of VSVΔG-Env.BG505 with G pseudotype. The schematic summarizes a procedure for preparing pseudotyped VSVΔG-Env.BG505.

Figures 14, 15:
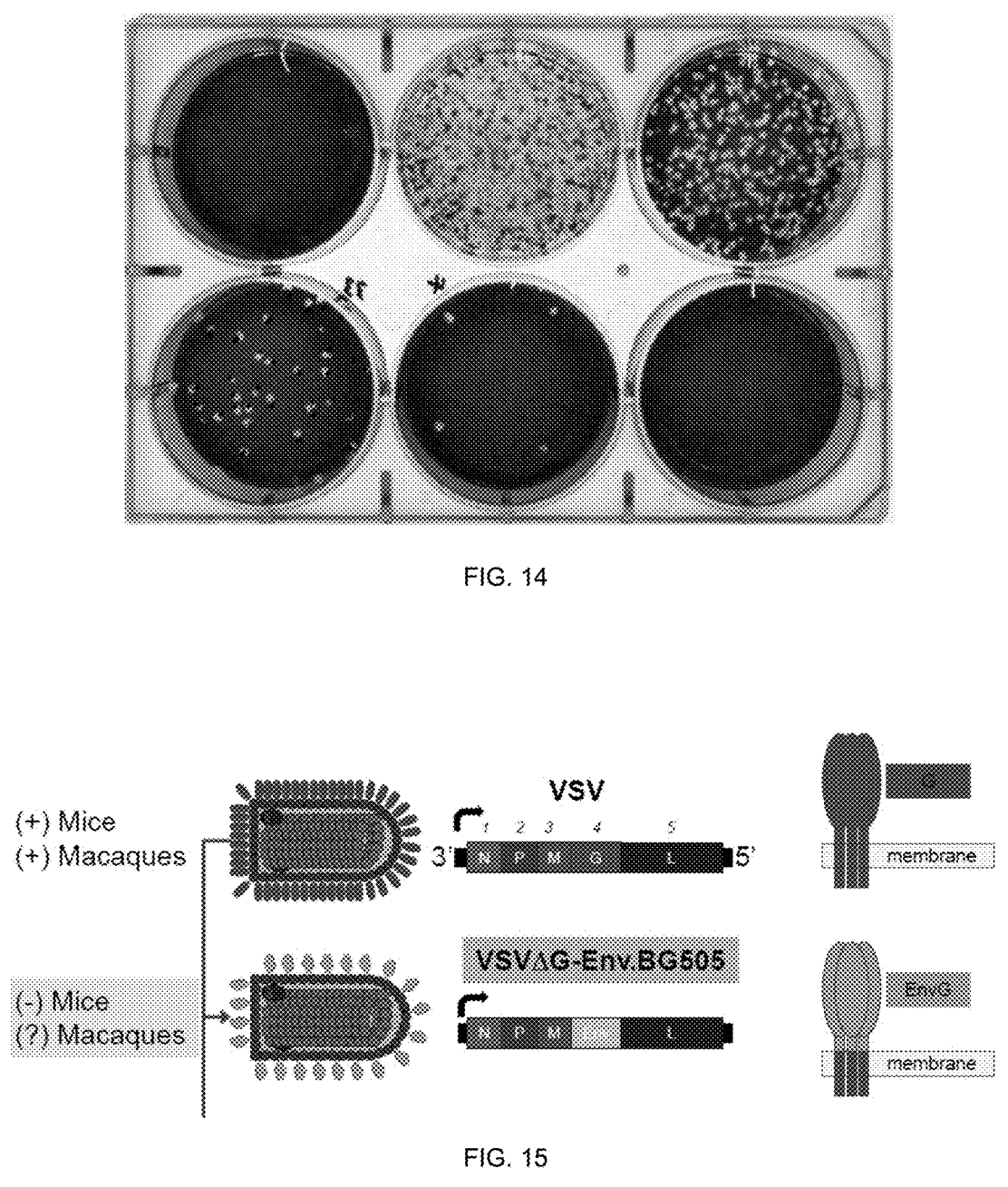

FIG. 14 shows that VSVΔG-Env.BG505 is cytolytic and that it forms real plaques after an overnight incubation.

FIG. 15 shows that VSV is neurovirulent after an intracranial injection.

Figure 16:
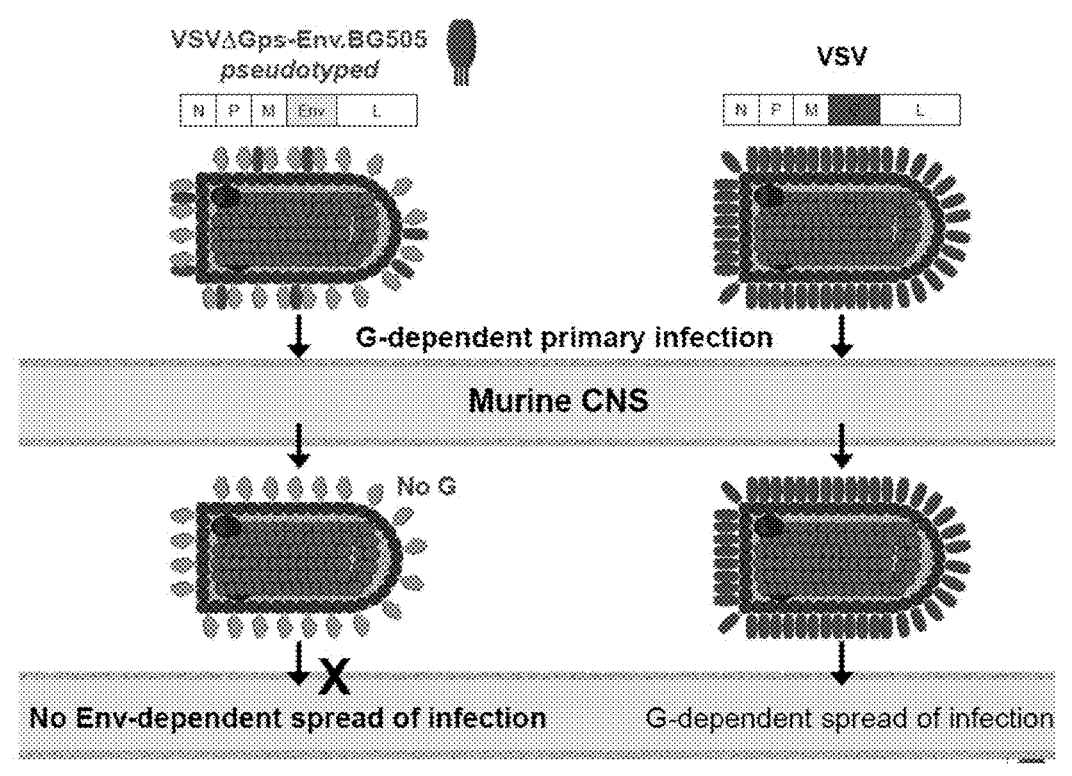

FIG. 16 shows that pseudotyped VSVΔGps-Env is not neurovirulent in mice.

Figure 19:
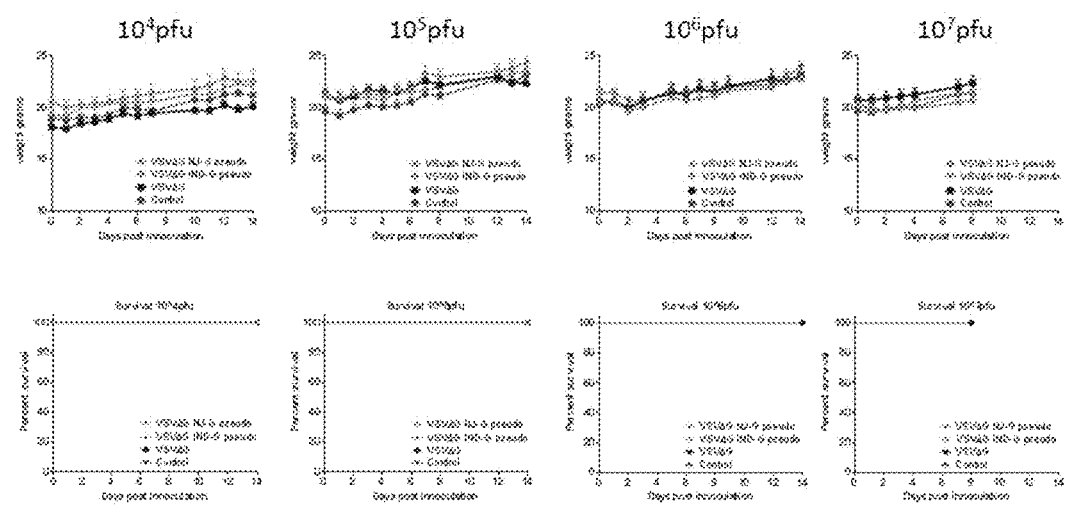

FIG. 19 shows a maximal tolerated dose study to test the safety of the VSVΔG-Env.BG505 using a mouse neurovirulence model. VSVΔG-Env.BG505 New Jersey G-pseudotype, VSVΔG-Env.BG505 Indiana G-pseudotype and VSVΔG-Env.BG505 were tested along with VSV-G5 and VSV-G4 vectors and negative control mice. No adverse events have been observed following intracranial inoculation with VSVΔG vectors. No weight lose in animals over the 14 days apart from a small decrease at day 1. There was 100% survival in 10^4, 10^5 and 10^6 pfu groups. No paralysis, limb weakness or loss of coordination was observed in any of the groups.

FIG. 20A shows binding of of PGT145 to sucrose purified VSVΔG-Env.BG505 chimera (2-fold serially diluted). FIG. 20B shows an association phase only. FIG. 20C shows a chimera virus standard curve: binding rate vs. concentration (pfu). The virus binding association data can be used to generate a standard curve of binding rate vs concentration and determine $K_D$.

Figure 21A:
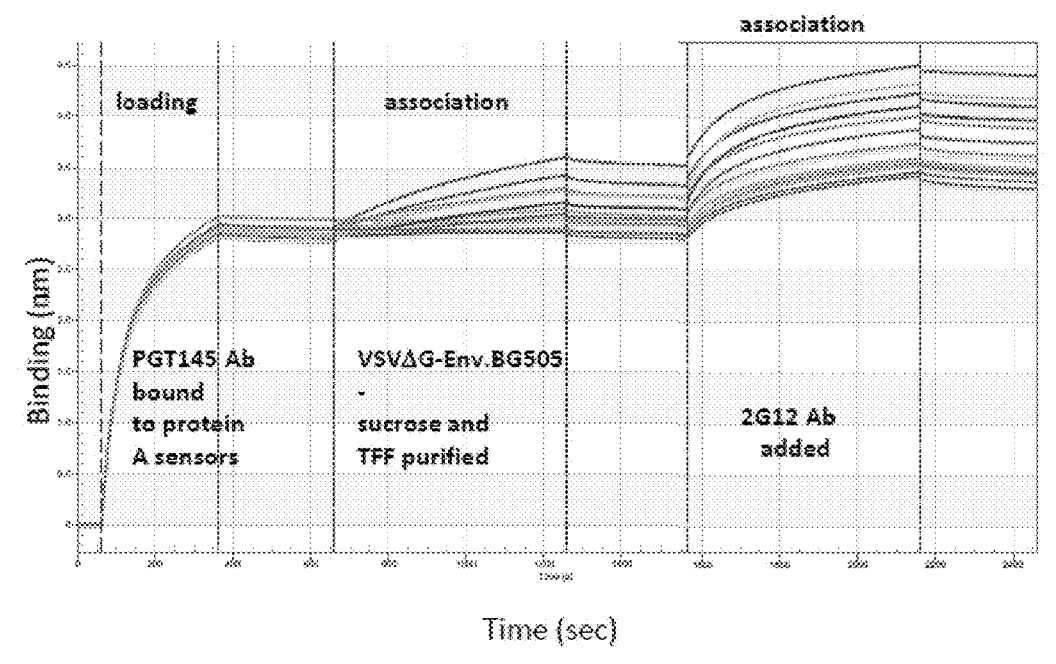

FIGS. 21A-21C show that PGT145 binds to sucrose and TFF purified VSVΔG-Env.BG505 batch to batch differences. FIG. 21A shows binding of PGT145 to sucrose and TFF purified VSVΔG-Env.BG505 chimera (2-fold serially diluted). FIG. 21B shows sucrose purified virus-association phase only. FIG. 21C shows TFF purified virus-association phase only. From the binding rates of the virus, use standard curve of protein to determine Env concentration. Data analyzed at the 2G12 binding step show better binding rates and therefore enhanced response signals with the sucrose purified sample. Batch to batch differences are determined.

FIG. 22 discloses "GGGGS" as SEQ ID NO: 6 and "8×His" as SEQ ID NO: 7.

FIG. 23A shows the baseline, loading of the HIV-Env subfragments and sera association, FIG. 23B shows loading samples PBS and C5V %, FIG. 23C shows loading samples BG505 and C4V4 and FIG. 23D shows loading samples GP41 and C3V3. The figures show that sera binds to all subfragments except C4V4.

FIGS. 28A-28D. Serum antibody analysis by Western blot. Western blot membranes were prepared using purified VSVΔG-Env.BG505 as a source of Env.BG505 and VSV polypeptides. The membranes were placed in multichannel devices to allow analysis of sera from individual animals. (A) Analysis of week-43 sera from all vaccinated animals and two controls. Labeled above the blot are the vaccine groups, animal numbers (NHP, nonhuman primate), and the SHIV challenge when infection occurred. Underlined NHP numbers indicate an animal that became infected during SHIV challenge. Polypeptide identities are labeled at the left side. Bands corresponding to Env gp41 were not clearly evident until after SHIV infection (FIG. 37). (B) Sera were analyzed from week 48. An independent full-length blot is included in FIG. 37A with all control animal sera. (C) Sera was analyzed from week 62 when 5 of 10 challenges were complete. Asterisks indicate animals infected after 5 challenges. Infected Control animal 31 did not produce an Env signal probably because it had a more severe progressive infection (FIG. 33) that interfered with humoral responses against Env and Gag (FIG. 34). (D) Analysis of sera from week 79, which was ~1 year after the final vaccination.

FIGS. 30A-30F. VSV-HIV vaccine design details. (A) Both vectors express HIV Env.BG505, which was modified to increase incorporation into the VSV particle by replacing the signal sequence, transmembrane region (TM) and cytoplasmic tail (CT) with sequence from G (serotype Indiana; IND). (B) VSVΔG-Env.BG505 particles used for vaccination were pseudotyped with G. Vaccinating with pseudotyped VSVΔG-Env.BG505 launches a more robust infection, because G binds ubiquitous cellular receptors allowing the initial round of infection to be independent of Env and the limited population of CD4+/CCR5+ cells. Pseudotyped virus was prepared by conducting the final amplification of vaccine material in VERO-CD4/CCR5 cells expressing G. (D-F) These schematics summarize how early stages of VSV vector infection progresses in macaques with pseudotyped VSVΔG-Env.BG505 (B) and VSV-G6-Env.BG505 (C). Both can use G to initiate primary infection (D), but subsequent cycles of VSVΔG-Env.BG505 infection and replication are Env-dependent while VSV-G6-Env.BG505 are G dependent. Additional information on the use of G in the vaccines is provided in FIG. 31.

FIGS. 31A-31C. VSV G serotype exchange. Because 3 vaccinations were planned and anti-G antibodies were known to develop when using VSV vectors that express G like VSV-G6-Env (FIG. 25C), Applicants used a G serotype exchange strategy to minimize potential effects of anti-G immunity (A) Timeline of vaccination and SHIV challenge shows how the vaccine G composition was varied. (B) For VSVΔG-Env.BG505, G was exchanged simply by pseudotyping with G from serotype New Jersey (NJ) or G IND. Only two different G pseudotypes were used for the three sequential vaccinations (A), because interim ELISA data showed that transient mucosal exposure to G in the pseudotyped VSVΔG-Env.BG505 particle did not elicit substantial amounts of anti-G antibodies (data not shown). (C) For sequential vaccination with VSV-G6-Env.BG505 (B), three vectors were used that differed in their G genes. The G genes came from different vesiculoviruses including VSV serotypes NJ or IND, or Maraba virus.

FIG. 32. VSV-HIV shedding in the oral cavity. Samples were collected at 3 days after each of the three vaccinations (FIG. 27A) by swabbing the oral cavity. Samples also were collected 7 days after the first vaccination. Material collected on the swabs was purified using procedures described in the Methods for detecting SHIV genomes in plasma after which qPCR was performed with an amplicon specific for the N gene. The lower limit of measurement was 50 genome copies per reaction. Low quantities of VSVΔG-EnvG.BG505 genomes were detected at 3 days following the first vaccination in 4 animals and in 3 macaques after the third vaccination. VSV-G6-Env.BG505 genomes were detected in swabs from 8 animals in greater quantities after the first vaccination and in 4 macaques following the third vaccination. These results indicated that VSVΔG-Env.BG505 shedding into the oral cavity was minimal to undetectable, while the quantity of VSV-G6-Env.BG505 genomes indicated that some virus shedding occurred although it remains to be determined whether live virus was present.

FIG. 33. SHIV infection and virus loads. Blood was collected at one and two weeks following each challenge to assess virus loads as described in the Methods. The plots show SHIV genome copies per ml of plasma as measured by RT-qPCR using a SIV Gag-specific amplicon. Animals with ≥200 copies on two successive blood draws were considered positive after which challenge was stopped. Animal numbers are shown to the right of the plots, and those positive for the Mamu-A*01 or Mamu-A*02 MHC alleles are indicated. Each group had two animals that were positive for Mamu-A*01 and two positive Mamu-A*02, which have been associated with control of disease progression. No macaques were included in the study with Mamu-B*17 or Mamu-B*08 alleles associated with strong replication control. Two animals in the Control group (indicated with X) experienced rapid disease progression and were euthanized before the end of the study.

FIGS. 34A-34C. Analysis of anti-Gag response to SHIV infection by Western blotting. (A) SHIV challenge timeline and labeling key for the blots below. (B-C) Gag-specific serum antibodies were detected by reactivity with recombinant SIV Gag (SIVmac239, p55 Gag; Protein Sciences Corp.) on Western blot membranes. Week-62 serum (B) was collected after completing the first 5 challenges and week-79 serum (C) was collected two months after the 10th challenge. Animal numbers are indicated above each lane, and in (B), an asterisk indicates that macaques were infected by the fifth challenge. Two infected animals in the control group (31 and 40) did not have strong anti-Gag or anti-Env (FIG. 37C) antibody responses, which was due to rapid disease progression (FIG. 33) inhibiting development of antibodies.

FIGS. 35A-35B. More detailed presentation of the SHIV infection timeline. (A) The Table supplements the survival curve shown in FIG. 26B and the antibody analysis in 3B by provides the timing of SHIV infection for each animal. (B) Boxplots showing ELISA titers during vaccination and challenge phases. The boxplots highlight the low titers in animals 11, 15, and 16 in the VSVΔG-Env.BG505 group prior to SHIV infection. Boxes show median and quartiles with whiskers extending at most 1.5 times the interquartile range.

FIG. 36. CD4 and CD8 T cell frequencies in peripheral blood. PBMCs harvested two weeks after the third vaccination (week 31) were stimulated with peptides representing Env.BG505 gp120, gp41, or VSV N after which intracellular cytokine staining and flow cytometry was conducted to quantify CD4 and CD8 T cells. Overall, the Env-specific T cell frequencies in peripheral blood were low (measurable limit set at 0.05%). In the VSV-G6-Env.BG505 group 5 of 10 animals were positive for gp120-specific CD4 T cells secreting IFNγ. VSV N-specific CD8 T cells also were detected secreting IFNγ in 9 of 10 macaques and TNFα in 4 or 10 animals. Notably, the frequency of T cells in peripheral blood specific for Env or N were below measurable limits in the group vaccinated with VSVΔG-Env.BG505.

FIG. 38. Cross clade Env binding detected with Western blot. A Western blot assay was performed using three different VSVΔG-Env.BG505 chimeras as the source of proteins on the blot. These included clade A.BG505 (different blot than in FIG. 4B), B.SF162.p3, and C.CH505 (week 100). The assay was performed as described in FIG. 28 using sera from the VSVΔG-Env.BG505 group (week 48). Animal numbers are at the top of the blot. Underlined animals were not protected during SHIV challenge.

DETAILED DESCRIPTION

Figures 2A, 2B, 2C, 2D:
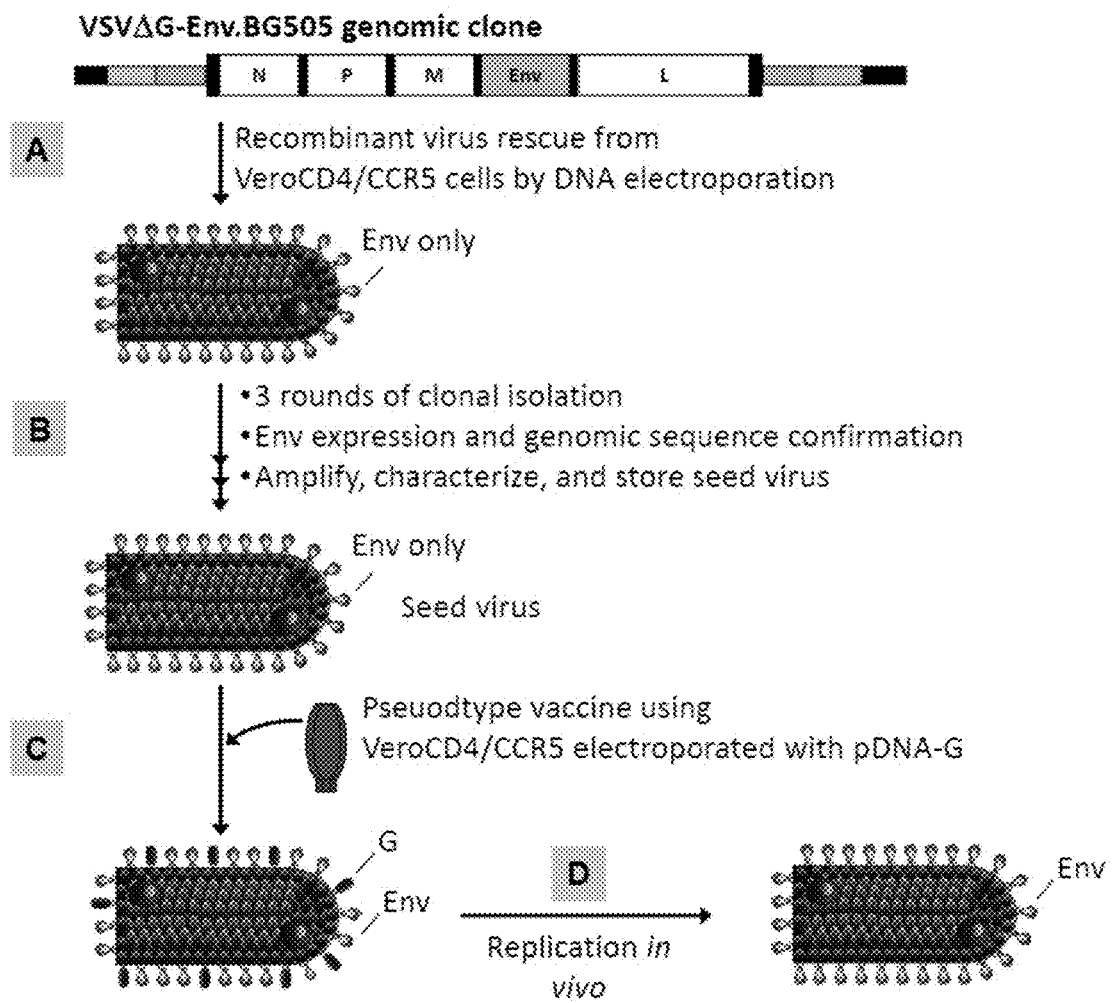
FIGS. 2A-2D. Summary of VSVΔG-Env.BG505 rescue and vaccine preparation. Steps in the process are summarized along with virus particle illustrations that show glycoprotein composition at different stages. Chimeric virus rescue is initiated by electroporating DNA (A) into Vero or VeroCD4/CCR5 cells. Virus that buds from electroporated cells then is expanded using VeroCD4/CCR5 cells before conducting 3 rounds of clonal isolation (B). Clonal isolates are characterized, and candidates are selected for seed virus amplification and storage. Conducting these steps using CD4+/CCR5+ ensures that the vector is genetically stable and is able to propagate efficiently using Env. When a pseudotyped vaccine preparation is produced (C), virus infection is performed using VeroCD4/CCR4 cells electroporated with DNA encoding G. Once the vaccine administered, replication in vivo (D) produces virus particles that lack the G glycoprotein.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the 20 heavy chain; two Fab' fragments are obtained per antibody molecule;

(iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the proteins of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

Advantageously, Applicants codon optimize the Env gene so it has the codon bias that is characteristic of VSV. This also results in a relatively low Guanine+Cytosine content of about 40-45%. See, e.g., Rabinovich et al., PLoS One. 2014 Sep. 12; 9(9):e106597. doi: 10.1371/journal.pone.0106597. eCollection 2014.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and proteins of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the proteins of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the proteins be expressed in vivo, for example when the transgenes of the invention are used in DNA or DNA-containing vaccines, any vector that allows for the expression of the proteins of the present invention and is safe for use in vivo may be used. In preferred embodiments the vectors used are safe for use in humans, mammals and/or laboratory animals.

For the proteins of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vesicular stomatitis virus (VSV) vector expressing a foreign epitope. Advantageously, the epitope is an HIV epitope. Any HIV epitope may be expressed in a VSV vector. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234;

5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610, 5,217,861; 5,208,321; 5,206,136; 5,198,346; 5,185,147; 5,178,865; 5,173,400; 5,173,399; 5,166,050; 5,156,951, 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

The vector of the present invention advantageously encodes for an Env.BG505 immunogen which may be encoded by a VSVΔG-Env.BG505 vaccine. The immunogen advantageously has the sequence as provided in SEQ ID NO: 2.

In another embodiment, the vector of the present invention may comprise a sequence of a VSVΔG-Env.BG505 genomic clone. The genomic clone advantageously has the sequence as provided as SEQ ID NO: 1.

Advantageously, the HIV epitope may be an Env precursor or gp160 epitope. The Env precursor or gp160 epitope may be recognized by antibodies PG9, PG16, 2G12, b12, 2F5, 4E10, Z13, or other broad potent neutralizing antibodies.

Figure 17:
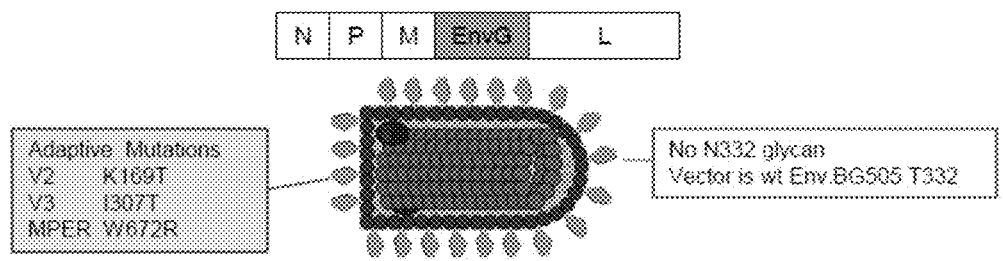
FIG. 17 shows that three Env mutations were present in the protective VSVΔG-Env.BG505 vaccine. Adaptive mutations emerged in Env during vector rescue and propagation that increased Env-dependent replication in VeroCD4/CCR5 cells (human CD4/CCR5). The substitutions are stable and included in vaccine vector tested in macaques. The 'adapted virus' is advanced as a genomic DNA clone containing these coding changes supports rescue of recombinant virus.
Figures 18A, 18B:
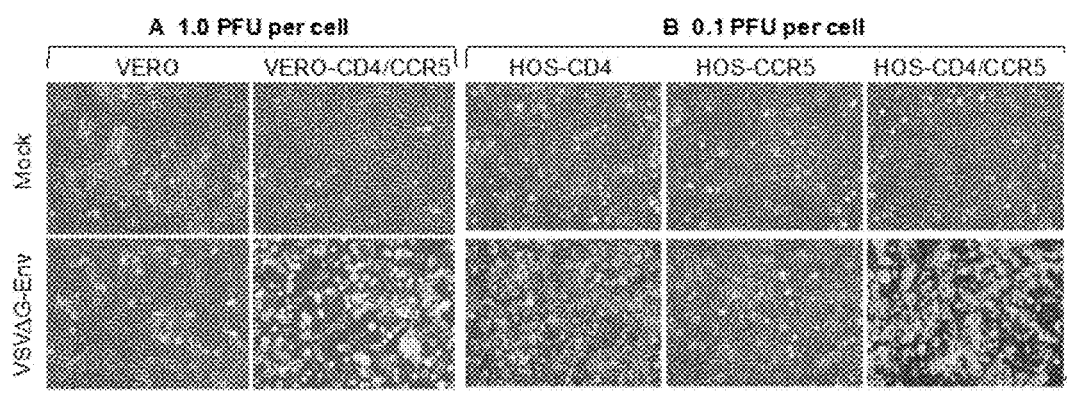
FIGS. 18A-18B show dependence of VSVΔG-EnvG.BG505 infection on CD4 and CCR5. The virus used in this experiment contained three adaptive amino: K169T, 1307T, and W672R. (A) VERO or VERO-CD4/CCR5 cell lines were infected with 1 plaque-forming unit per ml (PFU/ml) VSVΔG-Env.BG505 or a mock control. Cytopathic effect caused by VSVDG-Env.BG505 infection is evident only VERO-CD4/CCR5 cells. (B) HOS cells expressing CD4, CCR5 or both were infected with 0.1 PFU/ml of VSVDG-Env.BG505 or a mock control. Cytopathic effect produced by infection is only evident on cells expressing both CD4 and CCR5.
Figure 20A:
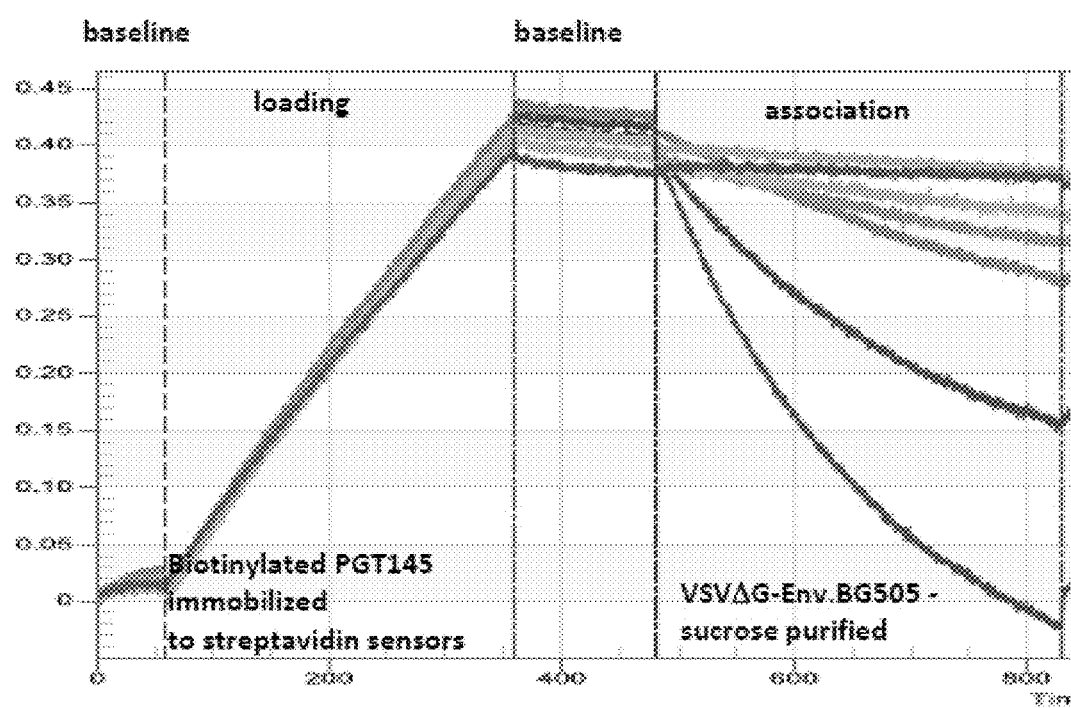
FIGS. 20A-20C show that PGT145 binds to sucrose purified VSVΔG-Env.BG505 and generates a standard curve of binding rate vs concentration (PFU).
Figure 20B:
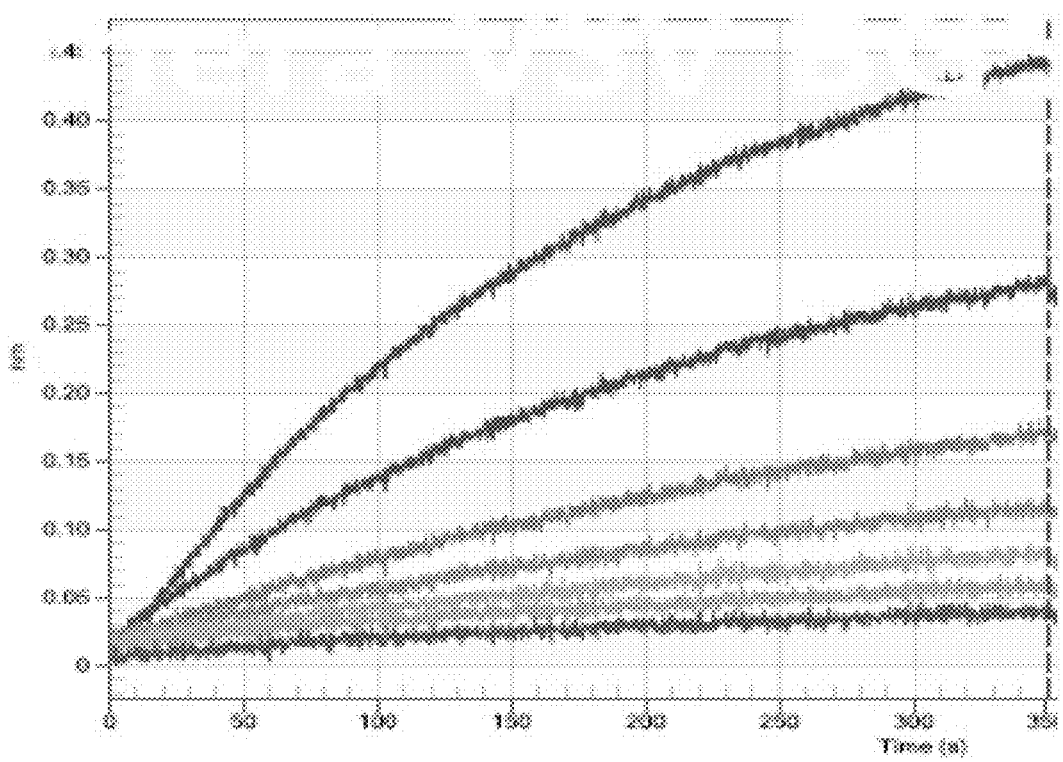
Figure 20C:
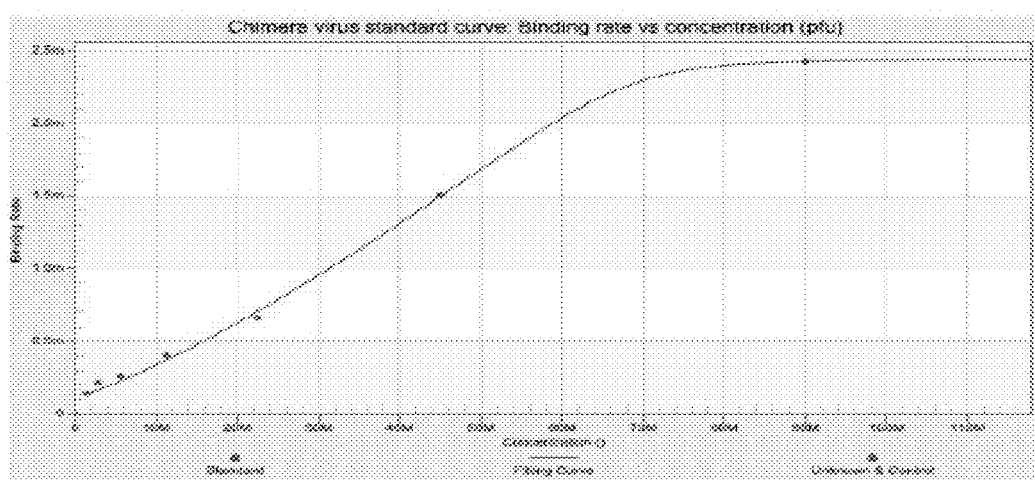
Figure 21B:
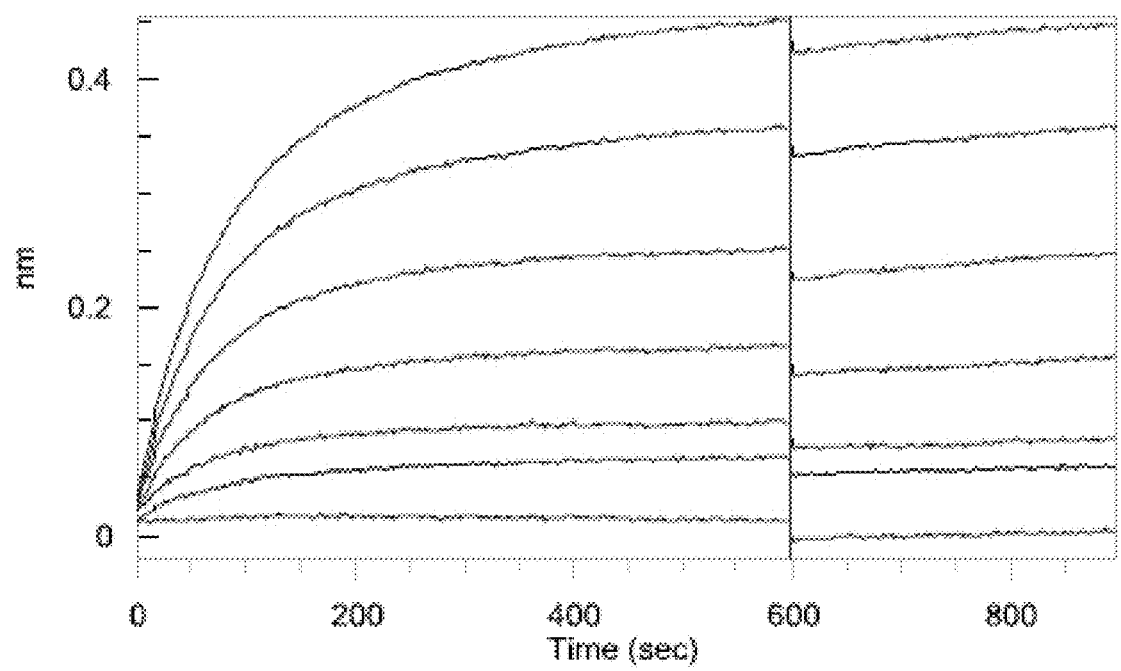
Figure 21C:
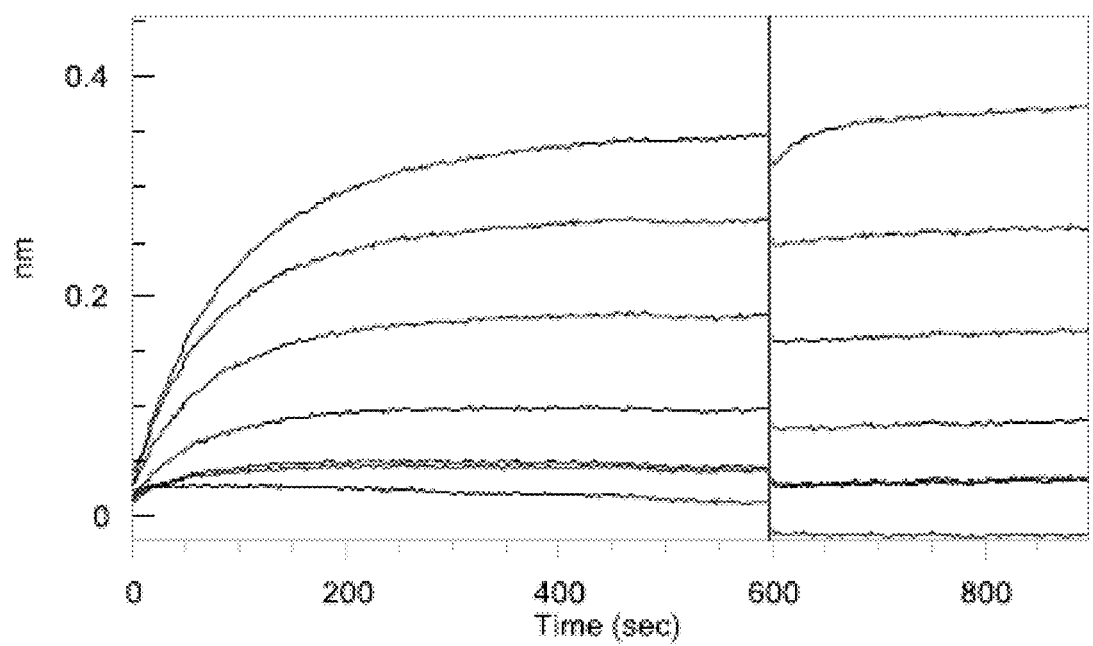
Figure 22:
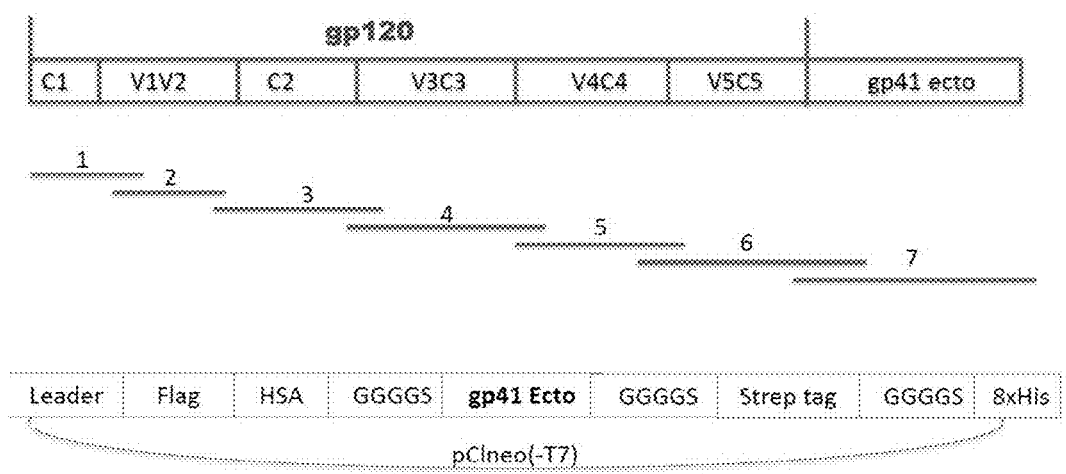
FIG. 22 depicts an octet application to monitor epitope mapping of sera from NHPs in the RM1401 and their binding profiles to HIV-Env subfragments.
Figure 23A:
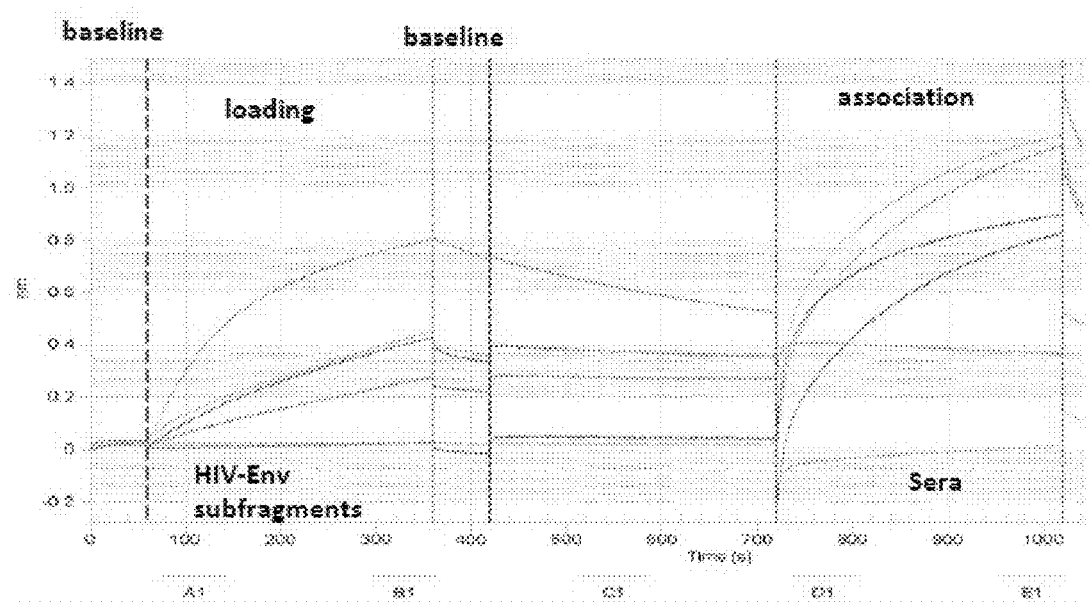
FIGS. 23A-23D show epitope mapping of sera from RM1401 indicate binding to HIV-Env subfragments. The biosensors are anti-HIS1K, the capture is different HIV-Env subfragments, the analyte molecule is sera 13 diluted 1:20 (from an NHP in the RM1401 study that showed protection after challenge with SHIV162p3) and the buffer is PBS/0.1% tween 20.
Figure 23B:
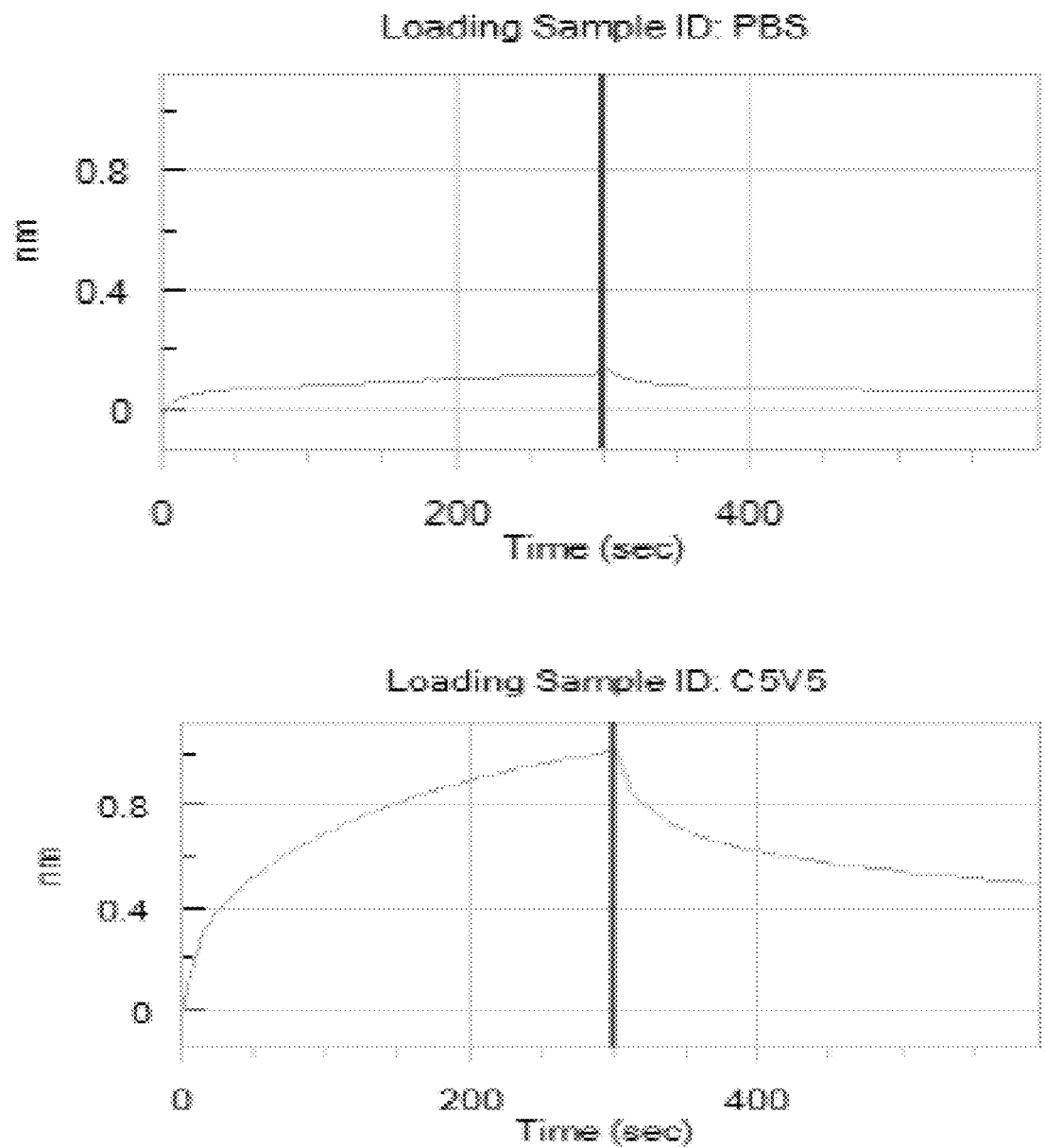
Figure 23C:
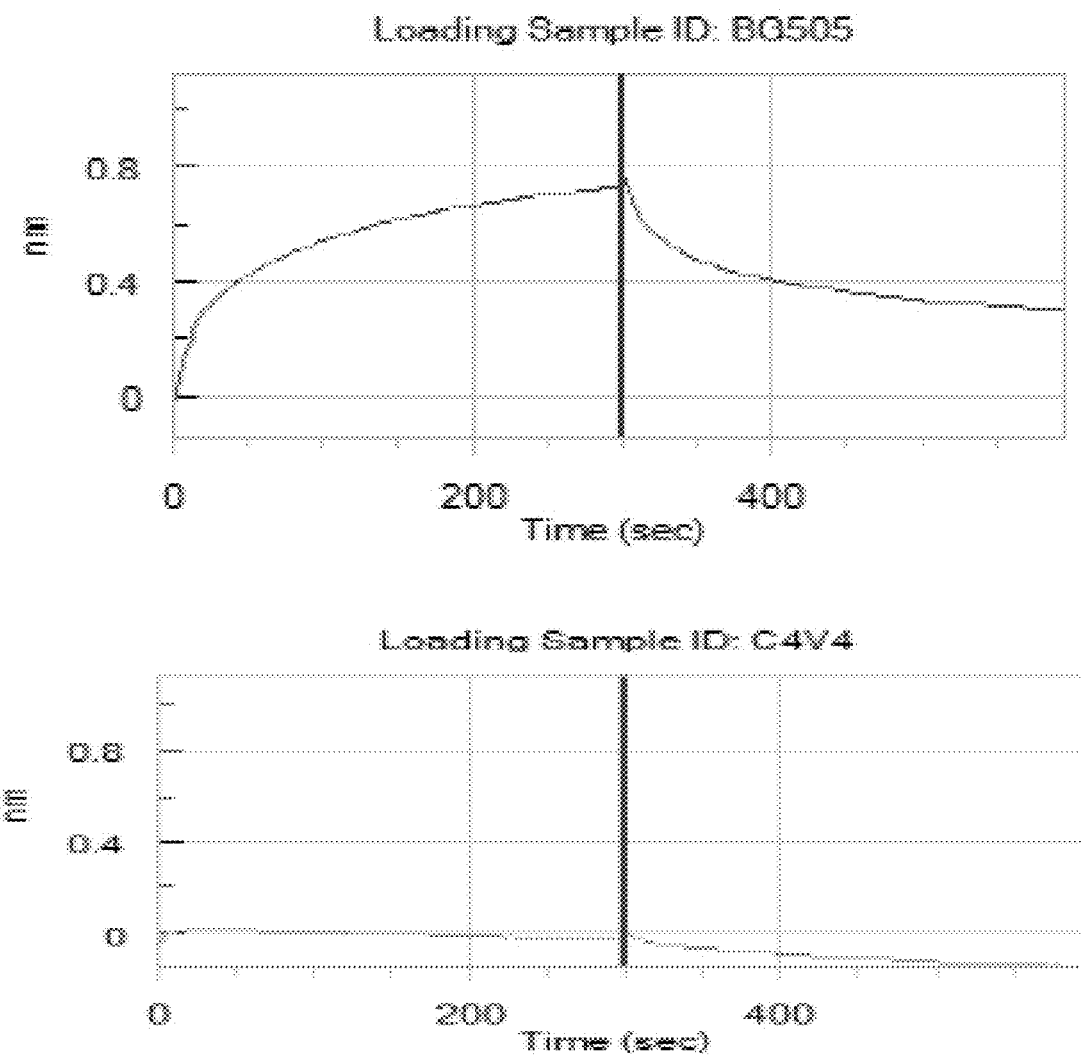
Figure 23D:
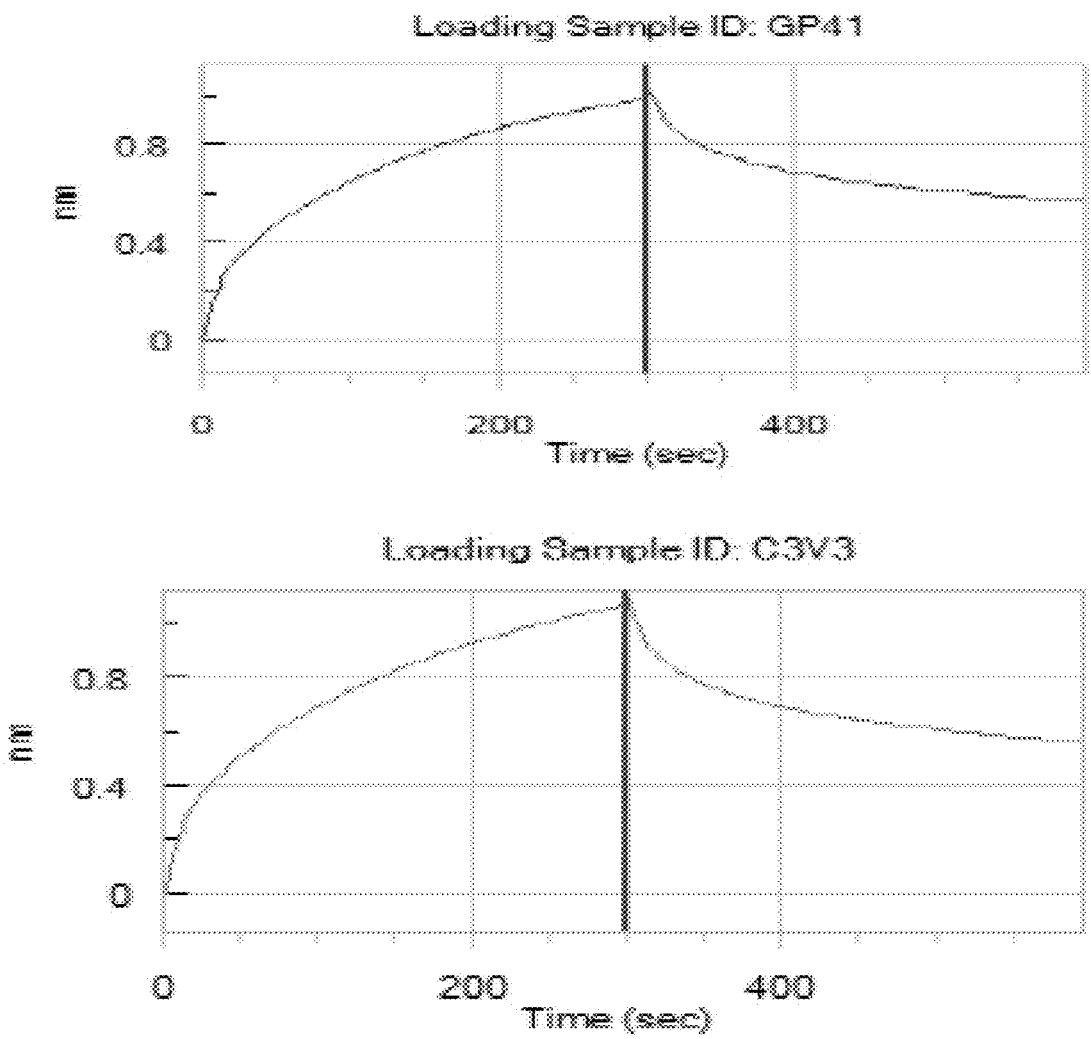
Figure 24:
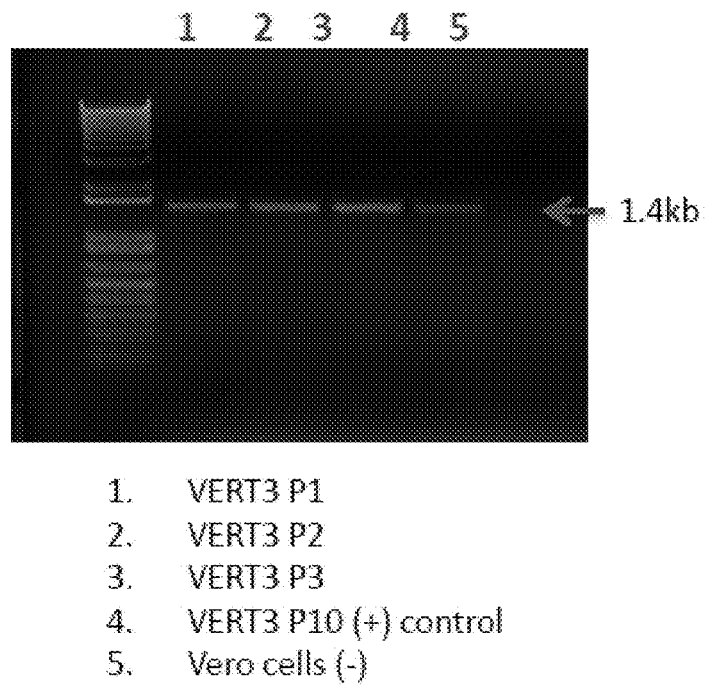
FIG. 24 depicts an evaluation of CD4 gene copy number in a VERT3 preclinical cell line. VERT3 cells were thawed, 3 passages were produced (P1, P2 and P3), gDNA was purified and RNase treated, DNA concentrations were determined by UV spectrophotometry (Nanodrop) and diluted to a stock concentration of 100 ng/ml, genetic integrity was determined by PCR/gel electrophoresis and stability was monitored by qPCR. Stability of CD4 and CCR5 genes in the VERT3 cell line is determined. Passage to passage consistency of the VERT3 cells is monitored. Three SYBR green qPCR assays (CD4, CCR5 and a reference gene β-glucuronidase) are designed. Absolute quantification is by a standard curve method. The stability of CD4 and CD4 copy number/cell is determined by the copy ration of CD4 to β-glucuronidase and likewise CCR5 stability.

Adaptive mutations emerged in Env during vector rescue and propagation that increased Env-dependent replication in VeroCD4/CCR5 cells (human CD4/CCR5) (see, e.g., FIG. 17). The substitutions are stable and included in vaccine vector tested in macaques. The 'adapted virus' is advanced as a genomic DNA clone containing these coding changes supports rescue of recombinant virus. Therefore, the present invention also encompasses mutations of env that may increase Env-dependent replication and/or contribute to immunogenicity. The EnvG mutations may include mutations of the lysine at AA position 169, the isoleucine at AA position 307 and/or the tryptophan at AA position 672. In an especially advantageous embodiment, the mutations are K169T, I307T and/or W672R. Other env mutations may be at P493, M343, K168, E168, Q440 and/or L494. In an advantageous embodiment, the mutations may be M343T, K168E, E168K, E164G, Q440R and/or L494F. see, e.g., Hoffenberg et al., J. Virol. May 2013 vol. 87 no. 10 5372-5383 for Env sequences and alignments.

In another embodiment, HIV, or immunogenic fragments thereof, may be utilized as the HIV epitope. For example, the HIV nucleotides of U.S. Pat. Nos. 7,393,949, 7,374,877 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an anti-HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the proteins of the invention can be expressed.

For example, when the aim is to express the proteins of the invention in vitro, or in cultured cells, or in any prokaryotic or eukaryotic system for the purpose of producing the protein(s), then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the proteins under the identified circumstances.

When the aim is to express the proteins of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the proteins of the invention in a laboratory animal, such as for pre-clinical testing of the HIV-1 immunogenic compositions and vaccines of the invention. In other embodiments, it will be desirable to express the proteins of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The present invention relates to recombinant vesicular stomatitis (VSV) vectors, however, other vectors may be contemplated in other embodiments of the invention such as, but not limited to, prime boost administration which may comprise administration of a recombinant VSV vector in combination with another recombinant vector expressing one or more HIV epitopes.

VSV is a very practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N-P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

The VSVs of U.S. Pat. Nos. 7,468,274; 7,419,829; 7,419,674; 7,344,838; 7,332,316; 7,329,807; 7,323,337; 7,259,015; 7,244,818; 7,226,786; 7,211,247; 7,202,079; 7,198,793; 7,198,784; 7,153,510; 7,070,994; 6,969,598; 6,958,226; RE38,824; PP15,957; 6,890,735; 6,887,377; 6,867,326; 6,867,036; 6,858,205; 6,835,568; 6,830,892; 6,818,209; 6,790,641; 6,787,520; 6,743,620; 6,740,764; 6,740,635; 6,740,320; 6,682,907; 6,673,784; 6,673,572; 6,669,936; 6,653,103; 6,607,912; 6,558,923; 6,555,107; 6,533,855; 6,531,123; 6,506,604; 6,500,623; 6,497,873; 6,489,142; 6,410,316; 6,410,313; 6,365,713; 6,348,312; 6,326,487; 6,312,682; 6,303,331; 6,277,633; 6,207,455; 6,200,811; 6,190,650; 6,171,862; 6,143,290; 6,133,027; 6,121,434; 6,103,462; 6,069,134; 6,054,127; 6,034,073; 5,969,211; 5,935,822; 5,888,727; 5,883,081; 5,876,727; 5,858,740; 5,843,723; 5,834,256; 5,817,491; 5,792,604; 5,789,229; 5,773,003; 5,763,406; 5,760,184; 5,750,396; 5,739,018; 5,698,446; 5,686,279; 5,670,354; 5,540,923; 5,512,421; 5,090,194; 4,939,176; 4,738,846; 4,622,292; 4,556,556 and 4,396,628 may be contemplated by the present invention.

The nucleotide sequences and vectors of the invention can be delivered to cells, for example if aim is to express and the HIV-1 antigens in cells in order to produce and isolate the expressed proteins, such as from cells grown in culture. For expressing the proteins in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the proteins can be carried out in any suitable type of host cells, such as bacterial cells, yeast, insect cells, and mammalian cells. The proteins of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, proteins of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the proteins of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, proteins of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the proteins of the invention to a subject, such as a human, such that the proteins are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof; buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratry animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen can also include VSV vectors that derive their G protein protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J Virol. 2000 December; 74(23):10903-10). The VSV vectors used in these examples contain a G protein derived from the Indiana serotype of VSV. Vectors can also be constructed to express epitopes in the context of G molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus an epitope like the HIV MPER can be delivered in a prime in the context of a G molecule that is from the Indiana serotype and the immune system can be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably which may comprise an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 0-29 or more weeks.

Preclinical efficacy in the SHIV challenge model was observed following mucosal vaccination with a total dose of $2 \times 10^8$ pfu per ml. The vaccine dose may be split between two sites, such as mucosal surfaces in the nasal and oral cavities, where each received $1 \times 10^8$ pfu applied in a buffered solution. Dosages ranging from about $1 \times 10^4$ to $1 \times 10^9$ pfu per ml are also contemplated. Single doses are also contemplated. Alternatively, a avaccination schedule from about 0 to 40 weeks is contemplated. A vaccination schedule may be at 0, 4 and 29 weeks.

Preclinical efficacy in the SHIV challenge model was observed with a vaccination schedule of 0, 4, and 29 weeks. Other vaccination schedules are also contemplated.

```
SEQ ID NO: 1:
   1   aaattaatac gactcactat agggagacca caacggtttc cctctagcgt tgtcttcgtc 61   tgatgagtcc gtgaggacga aactatagga aaggaattcc tatagtcACG AAGACAAACA

121   AACCATTATT ATCATTAAAA GGCTCAGGAG AAACTTTAAC AGTAATCAAA ATGTCTGTTA

181   CAGTCAAGAG AATCATTGAC AACACAGTCA TAGTTCCAAA ACTTCCTGCA AATGAGGATC

241   CAGTGGAATA CCCGGCAGAT TACTTCAGAA AATCAAAGGA GATTCCTCTT TACATCAATA

301   CTACAAAAAG TTTGTCAGAT CTAAGAGGAT ATGTCTACCA AGGCCTCAAA TCCGGAAATG

361   TATCAATCAT ACATGTCAAC AGCTACTTGT ATGGAGCATT GAAGGACATC CGGGGTAAGT

421   TGGATAAAGA TTGGTCAAGT TTCGGAATAA ACATCGGGAA GGCAGGGGAT ACAATCGGAA

481   TATTTGACCT TGTATCCTTG AAAGCCCTGG ACGGTGTACT TCCAGATGGA GTATCGGATG

541   CTTCCAGAAC CAGCGCAGAT GACAAATGGT TGCCTTTGTA TCTACTTGGC TTATACAGAG

601   TGGGCAGAAC ACAAATGCCT GAATACAGAA AAAGGCTCAT GGATGGGCTG ACAAATCAAT

661   GCAAAATGAT CAATGAACAG TTTGAACCTC TTGTGCCAGA AGGTCGTGAC ATTTTTGATG

721   TGTGGGGAAA TGACAGTAAT TACACAAAAA TTGTCGCTGC AGTGGACATG TTCTTCCACA

781   TGTTCAAAAA ACATGAATGT GCCTCGTTCA GATACGGAAC TATTGTTTCC AGATTCAAAG

841   ATTGTGCTGC ATTGGCAACA TTTGGACACC TCTGCAAAAT AACCGGAATG TCTACAGAAG

901   ATGTGACGAC CTGGATCTTG AACCGAGAAG TTGCAGATGA GATGGTCCAA ATGATGCTTC

961   CAGGCCAAGA AATTGACAAG GCTGATTCAT ACATGCCTTA TTTGATCGAC TTTGGATTGT

1021   CTTCTAAGTC TCCATATTCT TCCGTCAAAA ACCCTGCCTT CCACTTCTGG GGGCAATTGA

1081   CAGCTCTTCT GCTCAGATCC ACCAGAGCAA GGAATGCCCG ACAGCCTGAT GACATTGAGT

1141   ATACATCTCT TACTACAGCA GGTTTGTTGT ACGCTTATGC AGTAGGATCC TCTGCTGACT

1201   TGGCACAACA GTTTTGTGTT GGAGATAGCA AATACACTCC AGATGATAGT ACCGGAGGAT
```

-continued

```
1261  TGACGACTAA TGCACCGCCA CAAGGCAGAG ATGTGGTCGA ATGGCTCGGA TGGTTTGAAG

1321  ATCAAAACAG AAAACCGACT CCTGATATGA TGCAGTATGC GAAACGAGCA GTCATGTCAC

1381  TGCAAGGCCT AAGAGAGAAG ACAATTGGCA AGTATGCTAA GTCAGAGTTT GACAAATGAC

1441  CCTATAATTC TCAGATCACC TATTATATAT TATGCTAGCT ATGAAAAAAA CTAACAGATA

1501  TCATGGATAA TCTCACAAAA GTTCGTGAGT ATCTCAAGTC CTATTCTCGT CTAGATCAGG

1561  CGGTAGGAGA GATAGATGAG ATCGAAGCAC AACGAGCTGA AAAGTCCAAT TATGAGTTGT

1621  TCCAAGAGGA CGGAGTGGAA GAGCATACTA GGCCCTCTTA TTTTCAGGCA GCAGATGATT

1681  CTGACACAGA ATCTGAACCA GAAATTGAAG ACAATCAAGG CTTGTATGTA CCAGATCCGG

1741  AAGCTGAGCA AGTTGAAGGC TTTATACAGG GGCCTTTAGA TGACTATGCA GATGAGGACG

1801  TGGATGTTGT ATTCACTTCG GACTGGAAAC AGCCTGAGCT TGAATCCGAC GAGCATGGAA

1861  AGACCTTACG GTTGACATTG CCAGAGGGTT TAAGTGGAGA GCAGAAATCC CAGTGGCTTT

1921  TGACGATTAA AGCAGTCGTT CAAAGTGCCA ACACTGGAA TCTGGCAGAG TGCACATTTG

1981  AAGCATCGGG AGAAGGGGTC ATCATAAAAA AGCGCCAGAT AACTCCGGAT GTATATAAGG

2041  TCACTCCAGT GATGAACACA CATCCGTCCC AATCAGAAGC CGTATCAGAT GTTTGGTCTC

2101  TCTCAAAGAC ATCCATGACT TTCCAACCCA AGAAAGCAAG TCTTCAGCCT CTCACCATAT

2161  CCTTGGATGA ATTGTTCTCA TCTAGAGGAG AATTCATCTC TGTCGGAGGT AACGGACGAA

2221  TGTCTCATAA AGAGGCCATC CTGCTCGGTC TGAGGTACAA AAAGTTGTAC AATCAGGCGA

2281  GAGTCAAATA TTCTCTGTAG ACTAGTATGA AAAAAGTAA CAGATATCAC AATCTAAGTG

2341  TTATCCCAAT CCATTCATCA TGAGTTCCTT AAAGAAGATT CTCGGTCTGA AGGGGAAAGG

2401  TAAGAAATCT AAGAAATTAG GGATCGCACC ACCCCCTTAT GAAGAGGACA CTAACATGGA

2461  GTATGCTCCG AGCGCTCCAA TTGACAAATC CTATTTTGGA GTTGACGAGA TGGACACTCA

2521  TGATCCGAAT CAATTAAGAT ATGAGAAATT CTTCTTTACA GTGAAAATGA CGGTTAGATC

2581  TAATCGTCCG TTCAGAACAT ACTCAGATGT GGCAGCCGCT GTATCCCATT GGGATCACAT

2641  GTACATCGGA ATGGCAGGGA ACGTCCCTT CTACAAGATC TTGGCTTTTT TGGGTTCTTC

2701  TAATCTAAAG GCCACTCCAG CGGTATTGGC AGATCAAGGT CAACCAGAGT ATCATGCTCA

2761  CTGTGAAGGC AGGGCTTATT TGCCACACAG AATGGGGAAG ACCCCTCCCA TGCTCAATGT

2821  ACCAGAGCAC TTCAGAAGAC CATTCAATAT AGGTCTTTAC AAGGGAACGA TTGAGCTCAC

2881  AATGACCATC TACGATGATG AGTCACTGGA AGCAGCTCCT ATGATCTGGG ATCATTTCAA

2941  TTCTTCCAAA TTTTCTGATT TCAGAGAGAA GGCCTTAATG TTTGGCCTGA TTGTCGAGAA

3001  AAAGGCATCT GGAGCTTGGG TCCTGGATTC TGTCAGCCAC TTCAAATGAG CTAGTCTAGC

3061  TTCCAGCTTC TGAACAATCC CCGGTTTACT CAGTCTCTCC TAATTCCAGC CTTTCGAACA

3121  ACTAATATCC TGTCTTCTCT ATCCCTATGA AAAAACTAA CAGAGATCGA TCTGTTTCCT

3181  TGACACCAGG AGCCACCATG AAGTGCCTTT TGTACTTAGC TTTTTTATTC ATCGGGGTGA

3241  ATTGCAAGGC TAGCGCAGAG AATTTGTGGG TAACAGTCTA CTATGGAGTC CCTGTATGGA

3301  AGGATGCAGA GACAACATTG TTCTGTGCTA GTGACGCAAA GGCTTACGAG ACGGAGAAGC

3361  ACAATGTGTG GGCAACTCAC GCATGTGTCC CAACCGATCC AAATCCTCAA GAGATTCATC

3421  TAGAGAATGT GACTGAAGAA TTCAATATGT GGAAGAATAA TATGGTAGAG CAAATGCATA

3481  CAGATATCAT TAGTTTATGG GACCAGTCAC TTAAACCCTG CGTTAAATTG ACGCCTCTAT

3541  GTGTGACACT TCAATGTACT AATGTTACAA ACAACATAAC AGATGATATG AGAGGAGAAC

3601  TGAAGAACTG TAGTTTCAAC ATGACGACAG AGTTGCGTGA CAAGAAACAG AAAGTGTATT
```

```
-continued
3661  CACTATTCTA TCGGTTGGAT GTAGTACAGA TAAATGAGAA TCAAGGAAAC AGGTCCAACA
3721  ACTCTAACAA AGAGTACAGA CTTATTAATT GCAATACCAG TGCTATCACG CAAGCCTGCC
3781  CAAAGGTTTC ATTTGAACCA ATACCTATTC ATTATTGTGC ACCTGCTGGA TTCGCCATCC
3841  TCAAATGTAA AGACAAGAAG TTCAATGGAA CAGGACCCTG CCCATCAGTT TCAACCGTTC
3901  AGTGCACCCA CGGAATCAAG CCTGTAGTTA GTACTCAATT ATTGTTAAAT GGGAGCTTAG
3961  CTGAAGAAGA AGTTATGATT AGATCAGAGA ATATTACCAA TAATGCGAAG AACATCTTGG
4021  TTCAATTCAA TACTCCAGTC CAGATCAATT GCACAAGGCC TAATAATAAT ACCAGAAAGA
4081  GTATAAGAAT TGGGCCAGGA CAGGCATTCT ATGCAACAGG AGATATAATC GGAGACATTC
4141  GACAAGCGCA CTGCACTGTT TCTAAGGCCA CTTGGAATGA AACATTGGGT AAAGTTGTAA
4201  AGCAACTTCG GAAGCATTTC GGAAATAACA CAATTATTAG ATTTGCGAAC TCATCTGGAG
4261  GGGATCTGGA AGTGACAACA CACTCTTTCA ATTGCGGTGG CGAGTTCTTC TATTGTAATA
4321  CAAGTGGATT ATTTAACTCT ACTTGGATTT CAAATACCTC AGTCCAAGGA TCTAATTCAA
4381  CAGGGTCTAA CGATTCTATA ACATTACCTT GCCGTATAAA GCAAATTATT AATATGTGGC
4441  AAAGAATCGG GCAAGCGATG TATGCTCCAC CTATTCAAGG CGTGATTCGT TGCGTTTCAA
4501  ACATAACAGG GTTGATCCTG ACCAGGGATG GAGGCTCTAC CAATTCCACC ACCGAGACCT
4561  TCCGTCCCGG TGGCGGAGAT ATGCGGGATA ACTGGAGATC AGAGCTCTAT AAGTATAAGG
4621  TTGTGAAGAT TGAACCTCTT GGAGTTGCCC CTACAAGAGC AAAGAGAAGG GTGGTTGGCC
4681  GAGAGAAGAG AGCAGTTGGC ATCGGTGCTG TCTTTCTCGG ATTTCTTGGA GCAGCTGGAT
4741  CCACTATGGG AGCAGCATCA ATGACACTAA CAGTGCAGGC TAGAAATTTG CTTAGCGGAA
4801  TCGTTCAGCA GCAGAGCAAT TTACTAAGAG CAATTGAAGC ACAGCAACAT CTCTTAAAGT
4861  TGACGGTGTG GGGCATTAAA CAACTACAAG CGAGAGTGCT TGCCGTCGAA AGATATTTGC
4921  GAGACCAACA GCTATTGGGT ATTTGGGGTT GTTCTGGGAA ATTAATTTGC ACAACAAATG
4981  TTCCATGGAA CTCCTCCTGG AGTAATAGGA ATTAAGTGA GATATGGGAC AACATGACAT
5041  GGTTGCAGTG GGACAAGGAA ATCTCAAATT ATACACAGAT AATCTATGGA TTATTAGAAG
5101  AGTCTCAGAA TCAGCAAGAG AAGAATGAAC AGGATTTGCT TGCATTGGAT AAGTGGGCTT
5161  CTCTATGGAA CTGGTTCGAT ATTAGTAATT GGCTCTGGTA TATTAAGAGC TCTATTGCCT
5221  CTTTTTTCTT TATCATAGGG TTAATCATTG GACTATTCTT GGTTCTCCGA GTTGGTATTT
5281  ATCTTTGCAT TAAATTAAAG CACACCAAGA AAGACAGAT TTATACAGAC ATAGAGATGA
5341  ACCGACTTGG AAAGTAAAGC TCAAATCCTG CACAACAGAT TCTTCATGTT TGAACCAAAT
5401  CAACTTGTGA TATCATGCTC AAAGAGGCCT TAATTAAATT TTAATTTTTA ATTTTTATGA
5461  AAAAAACTAA CAGCAATCAT GGAAGTCCAC GATTTTGAGA CCGACGAGTT CAATGATTTC
5521  AATGAAGATG ACTATGCCAC AAGAGAATTC CTGAATCCCG ATGAGCGCAT GACGTACTTG
5581  AATCATGCTG ATTACAATTT GAATTCTCCT CTAATTAGTG ATGATATTGA CAATTTGATC
5641  AGGAAATTCA ATTCTCTTCC GATTCCCTCG ATGTGGGATA GTAAGAACTG GGATGGAGTT
5701  CTTGAGATGT TAACATCATG TCAAGCCAAT CCCATCTCAA CATCTCAGAT GCATAAATGG
5761  ATGGGAAGTT GGTTAATGTC TGATAATCAT GATGCCAGTC AAGGGTATAG TTTTTTACAT
5821  GAAGTGGACA AAGAGGCAGA ATAACATTT GACGTGGTGG AGACCTTCAT CCGCGGCTGG
5881  GGCAACAAAC CAATTGAATA CATCAAAAAG GAAAGATGGA CTGACTCATT CAAAATTCTC
5941  GCTTATTTGT GTCAAAAGTT TTTGGACTTA CACAAGTTGA CATTAATCTT AAATGCTGTC
6001  TCTGAGGTGG AATTGCTCAA CTTGGCGAGG ACTTTCAAAG GCAAAGTCAG AAGAAGTTCT
6061  CATGGAACGA ACATATGCAG GCTTAGGGTT CCCAGCTTGG GTCCTACTTT TATTTCAGAA
```

```
6121  GGATGGGCTT ACTTCAAGAA ACTTGATATT CTAATGGACC GAAACTTTCT GTTAATGGTC

6181  AAAGATGTGA TTATAGGGAG GATGCAAACG GTGCTATCCA TGGTATGTAG AATAGACAAC

6241  CTGTTCTCAG AGCAAGACAT CTTCTCCCTT CTAAATATCT ACAGAATTGG AGATAAAATT

6301  GTGGAGAGGC AGGGAAATTT TTCTTATGAC TTGATTAAAA TGGTGGAACC GATATGCAAC

6361  TTGAAGCTGA TGAAATTAGC AAGAGAATCA AGGCCTTTAG TCCCACAATT CCCTCATTTT

6421  GAAAATCATA TCAAGACTTC TGTTGATGAA GGGGCAAAAA TTGACCGAGG TATAAGATTC

6481  CTCCATGATC AGATAATGAG TGTGAAAACA GTGGATCTCA CACTGGTGAT TTATGGATCG

6541  TTCAGACATT GGGGTCATCC TTTTATAGAT TATTACGCTG GACTAGAAAA ATTACATTCC

6601  CAAGTAACCA TGAAGAAAGA TATTGATGTG TCATATGCAA AGCACTTGC AAGTGATTTA

6661  GCTCGGATTG TTCTATTTCA ACAGTTCAAT GATCATAAAA AGTGGTTCGT GAATGGAGAC

6721  TTGCTCCCTC ATGATCATCC CTTTAAAAGT CATGTTAAAG AAAATACATG GCCTACAGCT

6781  GCTCAAGTTC AAGATTTTGG AGATAAATGG CATGAACTTC CGCTGATTAA ATGTTTTGAA

6841  ATACCCGACT TACTAGACCC ATCGATAATA TACTCTGACA AAAGTCATTC AATGAATAGG

6901  TCAGAGGTGT TGAAACATGT CCGAATGAAT CCGAACACTC CTATCCCTAG TAAAAAGGTG

6961  TTGCAGACTA TGTTGGACAC AAAGGCTACC AATTGGAAAG AATTTCTTAA AGAGATTGAT

7021  GAGAAGGGCT TAGATGATGA TGATCTAATT ATTGGTCTTA AAGGAAAGGA GAGGGAACTG

7081  AAGTTGGCAG GTAGATTTTT CTCCCTAATG TCTTGGAAAT TGCGAGAATA CTTTGTAATT

7141  ACCGAATATT TGATAAAGAC TCATTTCGTC CCTATGTTTA AAGGCCTGAC AATGGCGGAC

7201  GATCTAACTG CAGTCATTAA AAAGATGTTA GATTCCTCAT CCGGCCAAGG ATTGAAGTCA

7261  TATGAGGCAA TTTGCATAGC CAATACACAT TGATTACGAAA AATGGAATAA CCACCAAAGG

7321  AAGTTATCAA ACGGCCCAGT GTTCCGAGTT ATGGGCCAGT TCTTAGGTTA TCCATCCTTA

7381  ATCGAGAGAA CTCATGAATT TTTTGAGAAA AGTCTTATAT ACTACAATGG AAGACCAGAC

7441  TTGATGCGTG TTCACAACAA CACACTGATC AATTCAACCT CCCAACGAGT TTGTTGGCAA

7501  GGACAAGAGG GTGGACTGGA AGGTCTACGG CAAAAAGGAT GGAGTATCCT CAATCTACTG

7561  GTTATTCAAA GAGAGGCTAA AATCAGAAAC ACTGCTGTCA AAGTCTTGGC ACAAGGTGAT

7621  AATCAAGTTA TTTGCACACA GTATAAAACG AAGAAATCGA GAAACGTTGT AGAATTACAG

7681  GGTGCTCTCA ATCAAATGGT TTCTAATAAT GAGAAAATTA TGACTGCAAT CAAAATAGGG

7741  ACAGGGAAGT TAGGACTTTT GATAAATGAC GATGAGACTA TGCAATCTGC AGATTACTTG

7801  AATTATGGAA AAATACCGAT TTTCCGTGGA GTGATTAGAG GGTTAGAGAC CAAGAGATGG

7861  TCACGAGTGA CTTGTGTCAC CAATGACCAA ATACCCACTT GTGCTAATAT AATGAGCTCA

7921  GTTTCCACAA ATGCTCTCAC CGTAGCTCAT TTTGCTGAGA ACCCAATCAA TGCCATGATA

7981  CAGTACAATT ATTTTGGGAC ATTTGCTAGA CTCTTGTTGA TGATGCATGA TCCTGCTCTT

8041  CGTCAATCAT TGTATGAAGT TCAAGATAAG ATACCGGGCT TGCACAGTTC TACTTTCAAA

8101  TACGCCATGT TGTATTTGGA CCCTTCCATT GGAGGAGTGT CGGGCATGTC TTTGTCCAGG

8161  TTTTTGATTA GAGCCTTCCC AGATCCCGTA ACAGAAAGTC TCTCATTCTG GAGATTCATC

8221  CATGTACATG CTCGAAGTGA GCATCTGAAG GAGATGAGTG CAGTATTTGG AAACCCCGAG

8281  ATAGCCAAGT TCCGAATAAC TCACATAGAC AAGCTAGTAG AAGATCCAAC CTCTCTGAAC

8341  ATCGCTATGG GAATGAGTCC AGCGAACTTG TTAAAGACTG AGGTTAAAAA ATGCTTAATC

8401  GAATCAAGAC AAACCATCAG GAACCAGGTG ATTAAGGATG CAACCATATA TTTGTATCAT

8461  GAAGAGGATC GGCTCAGAAG TTTCTTATGG TCAATAAATC CTCTGTTCCC TAGATTTTA
```

```
8521   AGTGAATTCA AATCAGGCAC TTTTTTGGGA GTCGCAGACG GGCTCATCAG TCTATTTCAA

8581   AATTCTCGTA CTATTCGGAA CTCCTTTAAG AAAAAGTATC ATAGGGAATT GGATGATTTG

8641   ATTGTGAGGA GTGAGGTATC CTCTTTGACA CATTTAGGGA AACTTCATTT GAGAAGGGGA

8701   TCATGTAAAA TGTGGACATG TTCAGCTACT CATGCTGACA CATTAAGATA CAAATCCTGG

8761   GGCCGTACAG TTATTGGGAC AACTGTACCC CATCCATTAG AAATGTTGGG TCCACAACAT

8821   CGAAAAGAGA CTCCTTGTGC ACCATGTAAC ACATCAGGGT TCAATTATGT TTCTGTGCAT

8881   TGTCCAGACG GGATCCATGA CGTCTTTAGT TCACGGGAC CATTGCCTGC TTATCTAGGG

8941   TCTAAAACAT CTGAATCTAC ATCTATTTTG CAGCCTTGGG AAAGGGAAAG CAAAGTCCCA

9001   CTGATTAAAA GAGCTACACG TCTTAGAGAT GCTATCTCTT GGTTTGTTGA ACCCGACTCT

9061   AAACTAGCAA TGACTATACT TTCTAACATC CACTCTTTAA CAGGCGAAGA ATGGACCAAA

9121   AGGCAGCATG GGTTCAAAAG AACAGGGTCT GCCCTTCATA GGTTTTCGAC ATCTCGGATG

9181   AGCCATGGTG GGTTCGCATC TCAGAGCACT GCAGCATTGA CCAGGTTGAT GGCAACTACA

9241   GACACCATGA GGGATCTGGG AGATCAGAAT TTCGACTTTT TATTCCAAGC AACGTTGCTC

9301   TATGCTCAAA TTACCACCAC TGTTGCAAGA GACGGATGGA TCACCAGTTG TACAGATCAT

9361   TATCATATTG CCTGTAAGTC CTGTTTGAGA CCCATAGAAG AGATCACCCT GGACTCAAGT

9421   ATGGACTACA CGCCCCCAGA TGTATCCCAT GTGCTGAAGA CATGGAGGAA TGGGGAAGGT

9481   TCGTGGGGAC AAGAGATAAA ACAGATCTAT CCTTTAGAAG GGAATTGAA GAATTTAGCA

9541   CCTGCTGAGC AATCCTATCA AGTCGGCAGA TGTATAGGTT TTCTATATGG AGACTTGGCG

9601   TATAGAAAAT CTACTCATGC CGAGGACAGT TCTCTATTTC CTCTATCTAT ACAAGGTCGT

9661   ATTAGAGGTC GAGGTTTCTT AAAAGGGTTG CTAGACGGAT TAATGAGAGC AAGTTGCTGC

9721   CAAGTAATAC ACCGGAGAAG TCTGGCTCAT TTGAAGAGGC CGGCCAACGC AGTGTACGGA

9781   GGTTTGATTT ACTTGATTGA TAAATTGAGT GTATCACCTC CATTCCTTTC TCTTACTAGA

9841   TCAGGACCTA TTAGAGACGA ATTAGAAACG ATTCCCCACA AGATCCCAAC CTCCTATCCG

9901   ACAAGCAACC GTGATATGGG GGTGATTGTC AGAAATTACT TCAAATACCA ATGCCGTCTA

9961   ATTGAAAAGG GAAAATACAG ATCACATTAT TCACAATTAT GGTTATTCTC AGATGTCTTA

10021  TCCATAGACT TCATTGGACC ATTCTCTATT TCCACCACCC TCTTGCAAAT CCTATACAAG

10081  CCATTTTTAT CTGGGAAAGA TAAGAATGAG TTGAGAGAGC TGGCAAATCT TTCTTCATTG

10141  CTAAGATCAG GAGAGGGGTG GGAAGACATA CATGTGAAAT TCTTCACCAA GGACATATTA

10201  TTGTGTCCAG AGGAAATCAG ACATGCTTGC AAGTTCGGGA TTGCTAAGGA TAATAATAAA

10261  GACATGAGCT ATCCCCCTTG GGGAAGGGAA TCCAGAGGGA CAATTACAAC AATCCCTGTT

10321  TATTATACGA CCACCCCTTA CCCAAAGATG CTAGAGATGC CTCCAAGAAT CCAAAATCCC

10381  CTGCTGTCCG GAATCAGGTT GGGCCAATTA CCAACTGGCG CTCATTATAA AATTCGGAGT

10441  ATATTACATG GAATGGGAAT CCATTACAGG GACTTCTTGA GTTGTGGAGA CGGCTCCGGA

10501  GGGATGACTG CTGCATTACT ACGAGAAAAT GTGCATAGCA GAGGAATATT CAATAGTCTG

10561  TTAGAATTAT CAGGGTCAGT CATGCGAGGC GCCTCTCCTG AGCCCCCCAG TGCCCTAGAA

10621  ACTTTAGGAG GAGATAAATC GAGATGTGTA AATGGTGAAA CATGTTGGGA ATATCCATCT

10681  GACTTATGTG ACCCAAGGAC TTGGGACTAT TTCCTCCGAC TCAAAGCAGG CTTGGGGCTT

10741  CAAATTGATT TAATTGTAAT GGATATGGAA GTTCGGGATT CTTCTACTAG CCTGAAAATT

10801  GAGACGAATG TTAGAAATTA TGTGCACCGG ATTTTGGATG AGCAAGGAGT TTTAATCTAC

10861  AAGACTTATG GAACATATAT TTGTGAGAGC GAAAAGAATG CAGTAACAAT CCTTGGTCCC

10921  ATGTTCAAGA CGGTCGACTT AGTTCAAACA GAATTTAGTA GTTCTCAAAC GTCTGAAGTA
```

-continued

```
10981   TATATGGTAT GTAAAGGTTT GAAGAAATTA ATCGATGAAC CCAATCCCGA TTGGTCTTCC
11041   ATCAATGAAT CCTGGAAAAA CCTGTACGCA TTCCAGTCAT CAGAACAGGA ATTTGCCAGA
11101   GCAAAGAAGG TTAGTACATA CTTTACCTTG ACAGGTATTC CCTCCCAATT CATTCCTGAT
11161   CCTTTTGTAA ACATTGAGAC TATGCTACAA ATATTCGGAG TACCCACGGG TGTGTCTCAT
11221   GCGGCTGCCT TAAAATCATC TGATAGACCT GCAGATTTAT TGACCATTAG CCTTTTTTAT
11281   ATGGCGATTA TATCGTATTA TAACATCAAT CATATCAGAG TAGGACCGAT ACCTCCGAAC
11341   CCCCCATCAG ATGGAATTGC ACAAAATGTG GGATCGCTA  TAACTGGTAT AAGCTTTTGG
11401   CTGAGTTTGA TGGAGAAAGA CATTCCACTA TATCAACAGT GTTTAGCAGT TATCCAGCAA
11461   TCATTCCCGA TTAGGTGGGA GGCTGTTTCA GTAAAAGGAG GATACAAGCA GAAGTGGAGT
11521   ACTAGAGGTG ATGGGCTCCC AAAAGATACC CGAATTTCAG ACTCCTTGGC CCCAATCGGG
11581   AACTGGATCA GATCTCTGGA ATTGGTCCGA AACCAAGTTC GTCTAAATCC ATTCAATGAG
11641   ATCTTGTTCA ATCAGCTATG TCGTACAGTG GATAATCATT TGAAATGGTC AAATTTGCGA
11701   AAAACACAG  GAATGATTGA ATGGATCAAT AGACGAATTT CAAAAGAAGA CCGGTCTATA
11761   CTGATGTTGA AGAGTGACCT ACACGAGGAA AACTCTTGGA GAGATTAAAA ATCATGAGG
11821   AGACTCCAAA CTTTAAGTAT GAAAAAAACT TTGATCCTTA AGACCCTCTT GTGGTTTTTA
11881   TTTTTTATCT GGTTTTGTGG TCTTCGTggc cggcatggtc ccagcctcct cgctggcgcc
11941   ggctgggcaa cattccgagg ggaccgtccc ctcggtaatg gcgaatggga cctgctaaca
12001   aagcccgaaa ggaagctgag ttggctgctg ccaccgctga gcaataacta gcataacccc
12061   ttggggcctc taaacgggtc ttgagggggtt ttttgctgaa aggaggaact atatccggat
12121   gcggccgatc cggctgctaa caaagcccga aggaagctg  agttggctg  tgccaccgct
12181   gagcaataac tagcataacc ccttgggggcc tctaaacggg tcttgagggg tttttttgctg
12241   aaaggaggaa ctatatccgg gttaacctgc attaatgaat cggccaacgc gcggggagag
12301   gcggtttgcg tattgggcgc tcttccgctt cctcgctcac tgactcgctg cgctcggtcg
12361   ttcggctgcg gcgagcggta tcagctcact caaaggcggt aatacggtta tccacagaat
12421   caggggataa cgcaggaaag aacatgtgag caaaaggcca gcaaaaggcc aggaaccgta
12481   aaaaggccgc gttgctggcg ttttttccata ggctccgccc cctgacgag  catcacaaaa
12541   atcgacgctc aagtcagagg tggcgaaacc cgacaggact ataaagatac caggcgtttc
12601   cccctggaag ctccctcgtg cgctctcctg ttccgaccct gccgcttacc ggatacctgt
12661   ccgcctttct cccttcggga agcgtggcgc tttctcaatg ctcacgcgt  aggtatctca
12721   gttcggtgta ggtcgttcgc tccaagctgg gctgtgtgca cgaaccccc  gttcagcccg
12781   accgctgcgc cttatccggt aactatcgtc ttgagtccaa cccggtaaga cacgacttat
12841   cgccactggc agcagccact ggtaacagga ttagcagagc gaggtatgta ggcggtgcta
12901   cagagttctt gaagtggtgg cctaactacg gctacactag aaggacagta tttggtatct
12961   gcgctctgct gaagccagtt accttcggaa aaagagttgg tagctcttga tccggcaaac
13021   aaaccaccgc tggtagcggt ggttttttg  tttgcaagca gcagattacg cgcagaaaaa
13081   aaggatctca agaagatcct ttgatctttt ctacggggtc tgacgctcag tggaacgaaa
13141   actcacgtta agggattttg gtcatgagat tatcaaaaag gatcttcacc tagatccttt
13201   taaattaaaa atgaagtttt aaatcaatct aaagtatata tgagtaaact tggtctgaca
13261   gttaccaatg cttaatcagt gaggcaccta tctcagcgat ctgtctattt cgttcatcca
13321   tagttgcctg actccccgtc gtgtagataa ctacgatacg ggagggctta ccatctggcc
```

-continued

```
13381   ccagtgctgc aatgataccg cgagacccac gctcaccggc tccagattta tcagcaataa 13441   accagccagc cggaagggcc gagcgcagaa gtggtcctgc aactttatcc gcctccatcc 13501   agtctattaa ttgttgccgg gaagctagag taagtagttc gccagttaat agtttgcgca 13561   acgttgttgc cattgctaca ggcatcgtgg tgtcacgctc gtcgtttggt atggcttcat 13621   tcagctccgg ttcccaacga tcaaggcgag ttacatgatc ccccatgttg tgcaaaaaag 13681   cggttagctc cttcggtcct ccgatcgttg tcagaagtaa gttggccgca gtgttatcac 13741   tcatggttat ggcagcactg cataattctc ttactgtcat gccatccgta agatgctttt 13801   ctgtgactgg tgagtactca accaagtcat tctgagaata gtgtatgcgg cgaccgagtt 13861   gctcttgccc ggcgtcaata cgggataata ccgcgccaca tagcagaact ttaaaagtgc 13921   tcatcattgg aaaacgttct tcggggcgaa aactctcaag gatcttaccg ctgttgagat 13981   ccagttcgat gtaacccact cgtgcaccca actgatcttc agcatctttt actttcacca 14041   gcgtttctgg gtgagcaaaa acaggaaggc aaaatgccgc aaaaaaggga ataagggcga 14101   cacggaaatg ttgaatactc atactcttcc tttttcaata ttattgaagc atttatcagg 14161   gttattgtct catgagcgga tacatatttg aatgtattta gaaaaataaa caaatagggg 14221   ttccgcgcac atttccccga aaagtgccac ctgacgtc
```

An annotated sequence of SEQ ID NO 1 is provided below. Coded protein disclosed as SEQ ID NO: 2.

```
                                 >T7-g10 Promoter
                                 |
aa att aat acg act cac tat agg gag acc aca acg gtt tcc ctc tag cgt tgt ctt cgt c      < 60
             10           20           30           40           50

>Hammerhead Ribozyme
                         |
tg atg agt ccg tga gga cga aac tat agg aaa gga att cct ata gtc ACG AAG ACA AAC A     < 120
             70           80           90          100          110

>VSV Leader
                          |
AA CCA TTA TTA TCA TTA AAA GGC TCA GGA GAA ACT TTA ACA GTA ATC AAA ATG TCT GTT A     < 180
            130          140          150          160          170

CA GTC AAG AGA ATC ATT GAC AAC ACA GTC ATA GTT CCA AAA CTT CCT GCA AAT GAG GAT C     < 240
            190          200          210          220          230

CA GTG GAA TAC CCG GCA GAT TAC TTC AGA AAA TCA AAG GAG ATT CCT CTT TAC ATC AAT A     < 300
            250          260          270          280          290

CT ACA AAA AGT TTG TCA GAT CTA AGA GGA TAT GTC TAC CAA GGC CTC AAA TCC GGA AAT G     < 360
            310          320          330          340          350

TA TCA ATC ATA CAT GTC AAC AGC TAC TTG TAT GGA GCA TTG AAG GAC ATC CGG GGT AAG T     < 420
            370          380          390          400          410

TG GAT AAA GAT TGG TCA AGT TTC GGA ATA AAC ATC GGG AAG GCA GGG GAT ACA ATC GGA A     < 480
            430          440          450          460          470

TA TTT GAC CTT GTA TCC TTG AAA GCC CTG GAC GGT GTA CTT CCA GAT GGA GTA TCG GAT G     < 540
            490          500          510          520          530

CT TCC AGA ACC AGC GCA GAT GAC AAA TGG TTG CCT TTG TAT CTA CTT GGC TTA TAC AGA G     < 600
            550          560          570          580          590

TG GGC AGA ACA CAA ATG CCT GAA TAC AGA AAA AGG CTC ATG GAT GGG CTG ACA AAT CAA T     < 660
            610          620          630          640          650

GC AAA ATG ATC AAT GAA CAG TTT GAA CCT CTT GTG CCA GAA GGT CGT GAC ATT TTT GAT G     < 720
            670          680          690          700          710

TG TGG GGA AAT GAC AGT AAT TAC ACA AAA ATT GTC GCT GCA GTG GAC ATG TTC TTC CAC A     < 780
            730          740          750          760          770
```

-continued

```
                           >N
                           |
TG TTC AAA AAA CAT GAA TGT GCC TCG TTC AGA TAC GGA ACT ATT GTT TCC AGA TTC AAA G   < 840
          790         800         810         820         830

AT TGT GCT GCA TTG GCA ACA TTT GGA CAC CTC TGC AAA ATA ACC GGA ATG TCT ACA GAA G   < 900
          850         860         870         880         890

AT GTG ACG ACC TGG ATC TTG AAC CGA GAA GTT GCA GAT GAG ATG GTC AAA TGA TGC TTC     < 960
          910         920         930         940         950

CA GGC CAA GAA ATT GAC AAG GCT GAT TCA TAC ATG CCT TAT TTG ATC GAC TTT GGA TTG T   < 1020
          970         980         990        1000        1010

CT TCT AAG TCT CCA TAT TCT TCC GTC AAA AAC CCT GCC TTC CAC TTC TGG GGG CAA TTG A   < 1080
         1030        1040        1050        1060        1070

CA GCT CTT CTG CTC AGA TCC ACC AGA GCA AGG AAT GCC CGA CAG CCT SAT GAC ATT GAG T   < 1140
         1090        1100        1110        1120        1130

AT ACA TCT CTT ACT ACA GCA GGT TTG TTG TAC GCT TAT GCA GTA GGA TCC TCT GCT GAC T   < 1200
         1150        1160        1170        1180        1190

TG GCA CAA CAG TTT TGT GTT GGA GAT AGC AAA TAC ACT CCA GAT GAT AGT ACC GGA GGA T   < 1260
         1210        1220        1230        1240        1250

TG ACG ACT AAT GCA CCG CCA CAA GGC AGA GAT GTG GTC GAA TGG CTC GGA TGG TTT GAA G   < 1320
         1270        1280        1290        1300        1310

AT CAA AAC AGA AAA CCG ACT CCT GAT ATG ATG CAG TAT GCG AAA CGA GCA GTC ATG TCA C   < 1380
         1330        1340        1350        1360        1370

TG CAA GGC CTA AGA GAG AAG ACA ATT GGC AAG TAT GCT AAG TCA GAG TTT GAC AAA TGA C   < 1440
         1390        1400        1410        1420        1430

CC TAT AAT TCT CAG ATC ACC TAT TAT ATA TTA TGC TAG CTA TGA AAA AAA CTA ACA GAT A   < 1500
         1450        1460        1470        1480        1490

TC ATG GAT AAT CTC ACA AAA GTT CGT GAG TAT CTC AAG TCC TAT TCT CGT CTA GAT CAG G   < 1560
         1510        1520        1530        1540        1550

CG GTA GGA GAG ATA GAT GAG ATC GAA GCA CAA CGA GCT GAA AAG TCC AAT TAT GAG TTG T   < 1620
         1570        1580        1590        1600        1610

TC CAA GAG GAC GGA GTG GAA GAG CAT ACT AGG CCC TCT TAT TTT CAG GCA GCA GAT GAT T   < 1680
         1630        1640        1650        1660        1670

CT GAC ACA GAA TCT GAA CCA GAA ATT GAA GAC AAT CAA GGC TTG TAT GTA CCA GAT CCG G   < 1740
         1690        1700        1710        1720        1730

AA GCT GAG CAA GTT GAA GGC TTT ATA CAG GGG CCT TTA GAT GAC TAT GCA GAT GAG GAC G   < 1800
         1750        1760        1770        1780        1790

TG GAT GTT GTA TTC ACT TCG GAC TGG AAA CAG CCT GAG CTT GAA TCC GAC GAG CAT GGA A   < 1860
         1810        1820        1830        1840        1850
                                                                       >P
                                                                       |
AG ACC TTA CGG TTG ACA TTG CCA GAG GGT TTA AGT GGA GAG CAG AAA TCC CAG TGG CTT T   < 1920
         1870        1880        1890        1900        1910

TG ACG ATT AAA GCA GTC GTT CAA AGT GCC AAA CAC TGG AAT CTG GCA GAG TGC ACA TTT G   < 1980
         1930        1940        1950        1960        1970

AA GCA TCG GGA GAA GGG GTC ATC ATA AAA AAG CGC CAG ATA ACT CCG GAT GTA TAT AAG G   < 2040
         1990        2000        2010        2020        2030

TC ACT CCA GTG ATG AAC ACA CAT CCG TCC CAA TCA GAA GCC GTA TCA GAT GTT TGG TCT C   < 2100
         2050        2060        2070        2080        2090

TC TCA AAG ACA TCC ATG ACT TTC AAA CCC AAG AAA GCA AGT CTT CAG CCT CTC ACC ATA T   < 2160
         2110        2120        2130        2140        2150

CC TTG GAT GAA TTG TTC TCA TCT AGA GGA GAA TTC ATC TCT GTC GGA GGT AAC GGA CGA A   < 2220
         2170        2180        2190        2200        2210

TG TCT CAT AAA GAG GCC ATC CTG CTC GGT CTG AGG TAC AAA AAG TTG TAC AAT CAG GCG A   < 2280
         2230        2240        2250        2260        2270

GA GTC AAA TAT TCT CTG TAG ACT AGT ATG AAA AAA AGT AAC AGA TAT CAC AAT CTA AGT G   < 2340
         2290        2300        2310        2320        2330
```

```
TT ATC CCA ATC CAT TCA TCA TGA GTT CCT TAA AGA AGA TTC TCG GTC TGA AGG GGA AAG G       < 2400
        2350          2360          2370          2380          2390

TA AGA AAT CTA AGA AAT TAG GGA TCG CAC CAC CCC CTX ATG AAG AGG ACA CTA ACA TGG A       < 2460
        2410          2420          2430          2440          2450

GT ATG CTC CGA GCG CTC CAA TTG ACA AAT CCT ATT TTG GAG TTG ACQ AGA TGG ACA CTC A       < 2520
        2470          2480          2490          2500          2510

TG ATC CGA ATC AAT TAA GAT ATG AGA AAT TCT TCT TTA CAG TGA AAA TGA CGG TTA GAT C       < 2580
        2530          2540          2550          2560          2570

TA ATC GTC CGT TCA GAA CAT ACT CAG ATG TGG CAG CCG CTG TAT CCC ATT GGG ATC ACA T       < 2640
        2590          2600          2610          2620          2630

GT ACA TCG GAA TGG CAG GGA AAC GTC CCT TCT ACA AGA TCT TGG CTT TTT TGG GTT CTT C       < 2700
        2650          2660          2670          2680          2690

>M
    |
TA ATC TAA AGG CCA CTC CAG CGG TAT TGG CAG ATC AAG GTC AAC CAG AGT ATC ATG CTC A       < 2760
        2710          2720          2730          2740          2750

CT GTG AAG GCA GGG CTT ATT TGC CAC ACA GAA TGG GGA AGA CCC CTC CCA TGC TCA ATG T       < 2820
        2770          2780          2790          2800          2810

AC CAG AGC ACT TCA GAA GAC CAT TCA ATA TAG GTC TTT ACA AGG GAA CGA TTG AGC TCA C       < 2880
        2830          2840          2850          2860          2870

AA TGA CCA TCT ACG ATG ATG AGT CAC TGG AAG CAG CTC CTA TGA TCT GGG ATC ATT CA A       < 2940
        2890          2900          2910          2920          2930

TT CTT CCA AAT TTT CTG ATT TCA GAG AGA AGG CCT AAT GT TTG GCC TGA TTG TCG AGA A       < 3000
        2950          2960          2970          2980          2990

AA AGG CAT CTG GAG CTT GGG TCC TGG ATT CTG TCA GCC ACT TCA AAT GAG CTA GTC TAG C       < 3060
        3010          3020          3030          3040          3050

TT CCA GCT TCT GAA CAA TCC CCG GTT TAC TCA GTC TCT CCT AAT TCC AGC CTT TCG AAC A       < 3120
        3070          3080          3090          3100          3110

AC TAA TAT CCT GTC TTC TCT ATC CCT ATG AAA AAA ACT AAC AGA GAT CGA TCT GTT TCC T       < 3180
        3130          3140          3150          3160          3170

TG ACA CCA GGA GCC ACC ATG AAG TGC CTT TTG TAC TTA GCT TTT TTA TTC ATC GGG GTG A       < 3240
                         M   K   C   L   L   Y   L   A   F   L   F   I   G   V   N
        3190          3200          3210          3220          3230

AT TGC AAG GCT AGC GCA GAG AAT TTG TGG GTA ACA GTC TAC TAT GGA GTC CCT GTA TGG A       < 3300
 C   K   A   S   A   E   N   L   W   V   T   V   Y   Y   G   V   P   V   W
        3250          3260          3270          3280          3290

AG GAT GCA GAG ACA ACA TTG TTC TGT GCT AGT GAC GCA AAG GCT TAG GAG ACG GAG AAG C       < 3360
 D   A   E   T   T   L   F   C   A   S   D   A   X   A   Y   E   T   E   K   H
        3310          3320          3330          3340          3350

AC AAT GTG TGG GCA ACT CAC GCA TGT GTC CCA ACC GAT CCA AAT CCT CAA GAG ATT CAT C       < 3420
 N   V   W   A   T   H   A   C   V   P   T   D   P   N   P   Q   E   I   H   L
        3370          3380          3390          3400          3410

TA GAG AAT GTG ACT GAA GAA TTC AAT ATG TGG AAG AAT AAT ATG GTA GAG CAA ATG CAT A       < 3480
 E   N   V   T   E   E   F   N   M   W   K   N   N   M   V   E   Q   M   H   T
        3430          3440          3450          3460          3470

CA GAT ATC ATT AGT TTA TGG GAC CAG TCA CTT AAA CCC TGC GTT AAA TTG ACG CCT CTA T       < 3540
 D   I   I   S   L   W   D   Q   S   L   K   P   C   V   K   L   T   P   L   C
        3490          3500          3510          3520          3530

GT GTG ACA CTT CAA TGT ACT AAT GTT ACA AAC AAC ATA ACA GAT GAT ATG AGA GGA GAA C       < 3600
 V   L   Q   C   T   N   V   T   N   N   I   T   D   D   M   R   S   E   L
        3550          3560          3570          3580          3590

TG AAG AAC TGT AGT TTC AAC ATG ACG ACA GAG TTG CGT GAC AAG AAA CAG AAA GTG TAT T       < 3660
 K   N   C   S   F   N   K   T   T   E   L   R   D   K   K   Q   K   V   Y   S
        3610          3620          3630          3640          3650

CA CTA TTC TAT CGG TTG GAT GTA GTA CAG ATA AAT GAG AAT CAA GGA AAC AGG TCC AAC A       < 3720
 L   F   Y   R   L   D   V   V   Q   I   N   E   N   Q   G   N   R   S   N   N
        3670          3680          3690          3700          3710
```

```
                                                       -continued
AC TCT AAC AAA GAG TAC AGA CTT ATT AAT TGC AAT AAC AGT GCT ATC ACG CAA GCC TGC C   < 3780
   S   N   K   E   Y   R   L   I   N   C   N   N   S   A   I   T   Q   A   C   P
          3730            3740            3750            3760            3770

CA AAG GTT TCA TTT GAA CCA ATA CCT ATT CAT TAT TGT GCA CCT GCT GGA TTC GCC ATC C   < 3840
   K   V   S   F   E   P   I   P   I   H   Y   C   A   P   A   G   F   A   I   L
          3790            3800            3810            3820            3830

TC AAA TGT AAA GAC AAG AAG TTC AAT GGA ACA GGA CCC TGC CCA TCA GTT TCA ACC GTT C   < 3900
   K   C   K   D   K   K   F   N   G   T   G   P   C   P   S   V   S   T   V   Q
          3850            3860            3870            3880            3890

AG TGC ACC CAC GGA ATC AAG CCT GTA GTT AGT ACT CAA TTA TTG TTA AAT GGG AGC TTA G   < 3960
   C   T   H   G   I   K   P   V   V   S   T   Q   L   L   L   N   G   S   L   A
          3910            3920            3930            3940            3950

CT GAA GAA GAA GTT ATG ATT AGA TCA GAG AAT ATT ACC AAT AAT GCG AAG AAC ATC TTG G   < 4020
   E   E   E   V   M   I   R   S   E   N   I   T   N   N   A   K   N   I   L   V
          3970            3980            3990            4000            4010

TT CAA TTC AAT ACT CCA GTC CAG ATC AAT TGC ACA AGG CCT AAT AAT AAT ACC AGA AAG A   < 4080
   Q   F   N   T   P   V   Q   I   N   C   T   R   P   N   N   N   T   R   K   S
          4030            4040            4050            4060            4070

GT ATA AGA ATT GGG CCA GGA CAG GCA TTC TAT GCA ACA GGA GAT ATA ATC GGA GAC ATT C   < 4140
   I   R   I   G   P   G   Q   A   F   Y   A   T   G   D   I   I   G   D   I   R
          4090            4100            4110            4120            4130

GA CAA GCG CAC TGC ACT GTT TCT AAG GCC ACT TGG AAT GAA ACA TTG GGT AAA GTT GTA A   < 4200
   Q   A   H   C   T   V   S   K   A   T   W   N   E   T   L   G   K   V   V   K
          4150            4160            4170            4180            4190

AG CAA CTT CGG AAG CAT TTC GGA AAT AAC ACA ATT ATT AGA TTT GCG AAC TCA TCT GGA G   < 4260
   Q   L   R   K   H   F   G   N   N   T   I   I   R   F   A   S   S   S   G   G
          4210            4220            4230            4240            4250

>Env.BG505 immunogen
                        |
GG GAT CTG GAA GTG ACA ACA CAC TCT TTC AAT TGC GGT GGC GAG TTC TTC TAT TGT AAT A   < 4320
   D   L   E   V   T   T   H   S   F   N   C   G   G   E   F   F   Y   C   N   T
          4270            4280            4290            4300            4310

CA AGT GGA TTA TTT AAC TCT ACT TGG ATT TCA AAT ACC TCA GTC CAA GGA TCT AAT TCA A   < 4380
   S   G   L   F   N   S   T   W   I   S   N   T   S   V   Q   G   S   N   S   T
          4330            4340            4350            4360            4370

CA GGG TCT AAC GAT TCT ATA ACA TTA CCT TGC CGT ATA AAG CAA ATT ATT AAT ATG TGG C   < 4440
   G   S   N   D   S   I   T   L   P   C   R   I   K   Q   I   I   N   M   W   Q
          4390            4400            4410            4420            4430

AA AGA ATC GGG CAA GCG ATG TAT GCT CCA CCT ATT CAA GGC GTG ATT CGT TGC GTT TCA A   < 4500
   K   R   I   G   Q   A   M   Y   A   P   P   I   Q   G   V   I   R   C   V   S
          4450            4460            4470            4480            4490

AC ATA ACA GGG TTG ATC CTG ACC AGG GAT GGA GGC TCT ACC AAT TCC ACC ACC GAG ACC T   < 4560
   N   I   T   G   L   I   L   T   R   D   G   G   S   T   N   S   T   T   E   T
          4510            4520            4530            4540            4550

TC CGT CCC GGT GGC GGA GAT ATG CGG GAT AAC TGG AGA TCA GAG CTC TAT AAG TAT AAG G   < 4620
   F   R   P   G   G   G   D   M   R   D   N   W   R   S   E   L   Y   K   Y   K
          4570            4580            4590            4600            4610

TT GTG AAG ATT GAA CCT CTT GGA GTT GCC CCT ACA AGA GCA AAG AGA AGG GTG GTT GGC C   < 4680
   V   V   K   I   E   P   L   G   V   A   P   T   R   A   K   R   R   V   V   G
          4630            4640            4650            4660            4670

GA GAG AAG AGA GCA GTT GGC ATC GGT GCT GTC TTT CTC GGA TTT CTT GGA GCA GCT GGA T   < 4740
   R   E   K   R   A   V   G   I   G   A   V   F   L   G   F   L   G   A   A   G
          4690            4700            4710            4720            4730

CC ACT ATG GGA GCA GCA TCA ATG ACA CTA ACA GTG CAG GCT AGA AAT TTG CTT AGC GGA A   < 4800
   S   T   M   G   A   A   S   M   T   L   T   V   Q   A   R   N   L   L   S   G
          4750            4760            4770            4780            4790

TC GTT CAG CAG CAG AGC AAT TTA CTA AGA GCA ATT GAA GCA CAG CAA CAT CTC TTA AAG T   < 4860
   I   V   Q   Q   Q   S   N   L   L   R   A   I   E   A   Q   Q   H   L   L   K
          4810            4820            4830            4840            4850

TC ACG GTG TGG GGC ATT AAA CAA CTA CAA GCG AGA GTG CTT GCC GTC GAA AGA TAT TTG C   < 4920
   L   T   V   W   G   I   K   Q   L   Q   A   R   V   L   A   V   E   R   Y   L
          4870            4880            4890            4900            4910
```

```
GA GAC CAA CAG CTA TTG GGT ATT TGG GGT TGT TCT GGG AAA TTA ATT TGC ACA ACA AAT G    < 4980
   D   Q   Q   L   L   G   I   W   G   C   S   G   K   L   I   C   T   T   N   V
              4930        4940        4950        4960        4970

TT CCA TGG AAC TCC TCC TGG AGT AAT AGG AAT TTA AGT GAG ATA TGG AAC AAC ATG ACA T    < 5040
   P   W   S   S   W   S   N   R   N   L   S   E   I   W   N   M   T   W
           4990        5000        5010        5020        5030

GG TTG CAG TGG GAC AAG GAA ATC TCA AAT TAT ACA CAG ATA ATC TAT GGA TTA TTA GAA G    < 5100
   L   Q   W   D   K   E   I   S   N   Y   T   Q   I   I   Y   G   L   L   E   E
              5050        5060        5070        5080        5090

AG TCT CAG AAT CAG CAA GAG AAG AAT GAA CAG GAT TTG CTT GCA TTG GAT AAG TGG GCT T    < 5160
   S   Q   N   Q   Q   E   K   N   E   Q   D   L   L   A   L   D   K   W   A   S
              5110        5120        5130        5140        5150

CT CTA TGG AAC TGG TTC GAT ATT AGT AAT TGG CTC TGG TAT ATT AAG AGC TCT ATT GCC T    < 5220
   L   K   N   W   F   D   I   S   N   W   L   W   Y   I   K   S   S   I   A   S
              5170        5180        5190        5200        5210

CT TTT TTC TTT ATC ATA GGG TTA ATC ATT GGA CTA TTC TTG GTT CTC CGA GTT GGT ATT T    < 5280
   F   F   F   I   I   G   L   I   I   G   L   F   L   V   L   R   V   G   I   Y
              5230        5240        5250        5260        5270

AT CTT TGC ATT AAA TTA AAG CAC ACC AAG AAA AGA CAG ATT TAT ACA GAC ATA GAG ATG A    < 5340
   L   C   I   K   L   K   H   T   K   K   R   Q   I   Y   T   D   I   E   M   N
              5290        5300        5310        5320        5330

AC CGA CTT GGA AAG TAA AGC TCA AAT CCT GCA CAA CAG ATT CTT CAT GTT TGA ACC AAA T    < 5400
   R   L   G   K   *
              5350        5360        5370        5380        5390

CA ACT TGT GAT ATC ATG CTC AAA GAG GCC TTA ATT AAA TTT TAA TTT TTA ATT TTT ATG A    < 5460
              5410        5420        5430        5440        5450

AA AAA ACT AAC AGC AAT CAT GGA AGT CCA CGA TTT TGA GAC CGA CGA GTT CAA TGA TTT C    < 5520
              5470        5480        5490        5500        5510

AA TGA AGA TGA CTA TGC CAC AAG AGA ATT CCT GAA TCC CGA TGA GCG CAT GAC GTA CTT G    < 5580
              5530        5540        5550        5560        5570

AA TCA TGC TGA TTA CAA TTT GAA TTC TCC TCT AAT TAG TGA TGA TAT TGA CAA TTT GAT C    < 5640
              5590        5600        5610        5620        5630

AG GAA ATT CAA TTC TCT TCC GAT TCC CTC GAT GTG GGA TAG TAA GAA CTG GGA TGG AGT T    < 5700
              5650        5660        5670        5680        5690

CT TGA GAT GTT AAC ATC ATG TCA AGC CAA TCC CAT CTC AAC ATC TCA GAT GCA TAA ATG G    < 5760
              5710        5720        5730        5740        5750

AT GGG AAG TTG GTT AAT GTC TGA TAA TCA TGA TGC CAG TCA AGG GTA TAG TTT TTT ACA T    < 5820
              5770        5780        5790        5800        5810

GA AGT GGA CAA AGA GGC AGA AAT AAC ATT TGA CGT GGT GGA GAC CTT CAT CCG CGG CTG G    < 5880
              5830        5840        5850        5860        5870

GG CAA CAA ACC AAT TGA ATA CAT CAA AAA GGA AAG ATG GAC TGA CTC ATT CAA AAT TCT C    < 5940
              5890        5900        5910        5920        5930

GC TTA TTT GTG TCA AAA GTT TTT GGA CTT ACA CAA GTT GAC ATT AAT CTT AAA TGC TGT C    < 6000
              5950        5960        5970        5980        5990

TC TGA GGT GGA ATT GCT CAA CTT GGC GAG GAC TTT CAA AGG CAA AGT CAG AAG AAG TTC T    < 6060
              6010        6020        6030        6040        6050

CA TGG AAC GAA CAT ATG CAG GCT TAG GGT TCC CAG CTT GGG TCC TAC TTT TAT TTC AGA A    < 6120
              6070        6080        6090        6100        6110

GG ATG GGC TTA CTT CAA GAA ACT TGA TAT TCT AAT GGA CCG AAA CTT TCT GTT AAT GGT C    < 6180
              6130        6140        6150        6160        6170

AA AGA TGT GAT TAT AGG GAG GAT GCA ACG GGT GCT ATC CAT GGT ATG TAG AAT AGA CAA C    < 6240
              6190        6200        6210        6220        6230

CT GTT CTC AGA GCA AGA CAT CTT CTC CCT TCT AAA TAT CTA CAG AAT TGG AGA TAA AAT T    < 6300
              6250        6260        6270        6280        6290

GT GGA GAG GCA GGG AAA TTT TTC TTA TGA CTT GAT TAA AAT GGT GGA ACC GAT ATG CAA C    < 6360
              6310        6320        6330        6340        6350
```

```
TT GAA GCT GAT GAA ATT AGC AAG AGA ATC AAG GCC TTT AGT CCC ACA ATT CCC TCA TTT T    < 6420
      6370         6380         6390         6400         6410
GA AAA TCA TAT CAA GAC TTC TGT TGA TGA AGG GGC AAA AAT TGA CCG AGG TAT AAG ATT C    < 6480
     6430         6440         6450         6460         6470
CT CCA TGA TCA GAT AAT GAG TGT GAA AAC AGT GGA TCT CAC ACT GGT GAT TTA TGG ATC G    < 6540
     6490         6500         6510         6520         6530
TT CAG ACA TTG GGG TCA TCC TTT TAT AGA TTA TTA CGC TGG ACT AGA AAA ATT ACA TTC C    < 6600
     6550         6560         6570         6580         6590
CA AGT AAC CAT GAA GAA AGA TAT TGA TGT GTC ATA TGC AAA AGC ACT TGC AAG TGA TTT A    < 6660
     6610         6620         6630         6640         6650
GC TCG GAT TGT TCT ATT TCA ACA GTT CAA TGA TCA TAA AAA GTG GTT CGT GAA TGG AGA C    < 6720
     6670         6680         6690         6700         6710
TT GCT CCC TCA TGA TCA TCC CTT TAA AAG TCA TGT TAA AGA AAA TAC ATG GCC TAC AQC T    < 6780
     6730         6740         6750         6760         6770
GC TCA AGT TCA AGA TTT TGG AGA TAA ATG GCA TGA ACT TCC GCT GAT TAA ATG TTT TGA A    < 6840
     6790         6800         6810         6820         6830
AT ACC CGA CTT ACT AGA CCC ATC GAT AAT ATA CTC TGA CAA AAG TCA TTC AAT GAA TAG G    < 6900
     6850         6860         6870         6880         6890
TC AGA GGT GTT GAA ACA TGT CCG AAT GAA TCC GAA CAC TCC TAT CCC TAG TAA AAA GGT G    < 6960
     6910         6920         6930         6940         6950
TT GCA GAC TAT GTT GGA CAC AAA GGC TAC CAA TTG GAA AGA ATT TCT AAA AGA GAT TGA T    < 7020
     6970         6980         6990         7000         7010
GA GAA GGG CTT AGA TGA TGA TGA TCT AAT TAT TGG TCT TAA AGG AAA GGA GAG GGA ACT G    < 7080
     7030         7040         7050         7060         7070
AA GTT GGC AGG TAG ATT TTT CTC CCT AAT GTC TTG GAA ATT GCG AGA ATA CTT TGT AAT T    < 7140
     7090         7100         7110         7120         7130
AC CGA ATA TTT GAT AAA GAC TCA TTT CGT CCC TAT GTT TAA AGG CCT GAC AAT GGC GGA C    < 7200
     7150         7160         7170         7180         7190
GA TCT AAC TGC AGT CAT AAA AAA GAT GTT AGA TTC CTC ATC CGG CCA AGG ATT GAA GTC A    < 7260
     7210         7220         7230         7240         7250
TA TGA GGC AAT TTG CAT AGC CAA TCA CAT TGA TTA CGA AAA ATG GAA TAA CCA CCA AAG G    < 7320
     7270         7280         7290         7300         7310
AA GTT ATC AAA CGG CCC AQT GTT CCG AGT TAT GGG CCA GTT CTT AGG TTA TCC ATC CTT A    < 7380
     7330         7340         7350         7360         7370
AT CGA GAG AAC TCA TGA ATT TTT TGA GAA AAG TCT TAT ATA CTA CAA TGG AAG ACC AGA C    < 7440
     7390         7400         7410         7420         7430
TT GAT GCG TGT TCA CAA CAA CAC ACT GAT CAA TTC AAC CTC CCA ACQ AGT TTG TTG GCA A    < 7500
     7450         7460         7470         7480         7490
GG ACA AGA GGG TGG ACT GGA AGG TCT ACG GCA AAA AGG ATG GAG TAT CCT CAA TCT ACT G    < 7560
     7510         7520         7530         7540         7550
GT TAT TCA AAG AGA GGC TAA AAT CAG AAA CAC TGC TGT CAA AGT CTT GGC ACA AGG TGA T    < 7620
     7570         7580         7590         7600         7610
AA TCA AGT TAT TTG CAC ACA GTA TAA AAC GAA GAA ATC GAG AAA CGT TGT AGA ATT ACA G    < 7680
     7630         7640         7650         7660         7670
GG TGC TCT CAA TCA AAT GGT TTC TAA TAA TGA GAA AAT TAT GAC TGC AAT CAA AAT AGG G    < 7740
     7690         7700         7710         7720         7730
AC AGG GAA GTT AGG ACT TTT GAT AAA TGA CGA TGA GAC TAT GCA ATC TGC AGA TTA CTT G    < 7800
     7750         7760         7770         7780         7790
AA TTA TGG AAA AAT ACC GAT TTT CCG TGG AGT GAT TAG AGG GTT AGA GAC CAA GAG ATG G    < 7860
     7810         7820         7830         7840         7850
TC ACG AGT GAC TTG TGT CAC CAA TGA CCA AAT ACC CAC TTG TGC TAA TAT AAT GAG CTC A    < 7920
     7870         7880         7890         7900         7910
GT TTC CAC AAA TGC TCT CAC CGT AGC TCA TTT TGC TGA GAA CCC AAT CAA TGC CAT GAT A    < 7980
     7930         7940         7950         7960         7970
```

-continued

```
CA GTA CAA TTA TTT TGG GAC ATT TGC TAG ACT CTT GTT GAT GAT GCA TGA TCC TGC TCT T      < 8040
      7990         8000         8010         8020         8030

CG TCA ATC ATT GTA TGA AGT TCA AGA TAA GAT ACC GGG CTT GCA CAG TTC TAC TTT CAA A      < 8100
      8050         8060         8070         8080         8090

TA CGC CAT GTT GTA TTT GGA CCC TTC CAT TGG AGG AGT GTC GGG CAT GTC TTT GTC CAG G      < 8160
      8110         8120         8130         8140         8150

TT TTT GAT TAG AGC CTT CCC AGA TCC CGT AAC AGA AAG TCT CTC ATT CTG GAG ATT CAT C      < 8220
      8170         8180         8190         8200         8210

CA TGT ACA TGC TCG AAG TGA GCA TCT GAA GGA GAT GAG TGC AGT ATT TGG AAA CCC CGA G      < 8280
      8230         8240         8250         8260         8270

AT AGC CAA GTT CCG AAT AAC TCA CAT AGA CAA GCT AGT AGA AGA TCC AAC CTC TCT GAA C      < 8340
      8290         8300         8310         8320         8330

AT CGC TAT GGG AAT GAG TCC AGC GAA CTT GTT AAA GAC TGA GGT TAA AAA ATG CTT AAT C      < 8400
      8350         8360         8370         8380         8390

GA ATC AAG ACA AAC CAT CAG GAA CCA GGT GAT TAA GGA TGC AAC CAT ATA TTT GTA TCA T      < 8460
      8410         8420         8430         8440         8450

GA AGA GGA TCG GCT CAG AAG TTT CTT ATG GTC AAT AAA TCC TCT GTT CCC TAG ATT TTT A      < 8520
      8470         8480         8490         8500         8510

AG TGA ATT CAA ATC AGG CAC TTT TTT GGG AGT CGC AGA CGG GCT CAT CAG TCT ATT TCA A      < 8580
      8530         8540         8550         8560         8570

AA TTC TCG TAC TAT TCG GAA CTC CTT TAA GAA AAA GTA TCA TAG GGA ATT GGA TGA TTT G      < 8640
      8590         8600         8610         8620         8630

>L
    |
AT TGT GAG GAG TGA GGT ATC CTC TTT GAC ACA TTT AGG GAA ACT TCA TTT GAG AAG GGG A      < 8700
      8650         8660         8670         8680         8690

TC ATG TAA AAT GTG GAC ATG TTC AGC TAG TCA TGC TGA CAC ATT AAG ATA CAA ATC CTG G      < 8760
      8710         8720         8730         8740         8750

GG CCG TAC AGT TAT TGG GAC AAC TGT ACC CCA TCC ATT AGA AAT GTT GGG TCC ACA ACA T      < 8820
      8770         8780         8790         8800         8810

CG AAA AGA GAC TCC TTG TGC ACC ATG TAA CAC ATC AGG GTT CAA TTA TGT TTC TGT GCA T      < 8880
      8830         8840         8850         8860         8870

TG TCC AGA CGG GAT CCA TGA CGT CTT TAG TTC ACG GGA CCA TTG CCT GCT TAT CTA GG G      < 8940
      8890         8900         8910         8920         8930

TC TAA AAC ATC TGA ATC TAC ATC TAT TTT GCA GCC TTG GGA AAG GGA AAG CAA AGT CCC A      < 9000
      8950         8960         8970         8980         8990

CT GAT TAA AAG AGC TAC ACG TCT TAG AGA TGC TAT CTC TTG GTT TGT TGA ACC CGA CTC T      < 9060
      9010         9020         9030         9040         9050

AA ACT AGC AAT GAC TAT ACT TTC TAA CAT CCA CTC TTT AAC AGG CGA AGA ATG GAC CAA A      < 9120
      9070         9080         9090         9100         9110

AG GCA GCA TGG GTT CAA AAG AAC AGG GTC TGC CCT TCA TAG GTT TTC GAC ATC TCG GAT G      < 9180
      9130         9140         9150         9160         9170

AG CCA TGG TGG GTT CGC ATC TCA GAG CAC TGC AGC ATT GAC CAG GTT GAT GGC AAC TAC A      < 9240
      9190         9200         9210         9220         9230

GA CAC CAT GAG GGA TCT GGG AGA TCA GAA TTT CGA CTT TTT ATT CCA AGC AAC GTT GCT C      < 9300
      9250         9260         9270         9280         9290

TA TQC TCA AAT TAC CAC CAC TGT TGC AAG AGA CGG ATG GAT CAC CAG TTG TAC AGA TCA T      < 9360
      9310         9320         9330         9340         9350

TA TCA TAT TGC CTG TAA GTC CTG TTT GAG ACC CAT AGA AGA GAT CAC CCT GGA CTC AAG T      < 9420
      9370         9380         9390         9400         9410

AT GGA CTA CAC GCC CCC AGA TGT ATC CCA TGT GCT GAA GAC ATG GAG GAA TGG GGA AGG T      < 9480
      9430         9440         9450         9460         9470

TC GTG GGG ACA AGA GAT AAA ACA GAT CTA TCC TTT AGA AGG GAA TTG GAA GAA TTT AGC A      < 9540
      9490         9500         9510         9520         9530

CC TGC TGA GCA ATC CTA TCA AGT CGG CAG ATG TAT AGG TTT TCT ATA TGG AGA CTT GGC G      < 9600
```

```
                        9550       9560       9570       9580       9590
TA TAG AAA ATC TAC TCA TGC CGA GGA CAG TTC TCT ATT TCC TCT ATC TAT ACA AGG TCG T    < 9660
     9610       9620       9630       9640       9650

AT TAG AGG TCG AGG TTT CTT AAA AGG GTT GCT AGA CGG ATT AAT GAG AGC AAG TTG CTG C    < 9720
     9670       9680       9690       9700       9710

CA AGT AAT ACA CCG GAG AAG TCT GGC TCA TTT GAA GAG GCC GGC CAA CGC AGT GTA CGG A    < 9780
     9730       9740       9750       9760       9770

GG TTT GAT TTA CTT GAT TGA TAA ATT GAG TGT ATC ACC TCC ATT CCT TTC TCT TAC TAG A    < 9840
     9790       9800       9810       9820       9830

TC AGG ACC TAT TAG AGA CGA ATT AGA AAC GAT TCC CCA CAA GAT CCC AAC CTC CTA TCC G    < 9900
     9850       9860       9870       9880       9890

AC AAG CAA CCG TGA TAT GGG GGT GAT TGT CAG AAA TTA CTT CAA ATA CCA ATG CCG TCT A    < 9960
     9910       9920       9930       9940       9950

AT TGA AAA GGG AAA ATA CAG ATC ACA TTA TTC ACA ATT ATG GTT ATT CTC AGA TGT CTT A    < 10020
     9970       9980       9990       10000      10010

TC CAT AGA CTT CAT TGG ACC ATT CTC TAT TTC CAC CAC CCT CTT GCA AAT CCT ATA CAA G    < 10080
     10030      10040      10050      10060      10070

CC ATT TTT ATC TGG GAA AGA TAA GAA TGA GTT GAG AGA GCT GGC AAA TCT TTC TTC ATT G    < 10140
     10090      10100      10110      10120      10130

CT AAG ATC AGG AGA GGG GTG GGA AGA CAT ACA TGT GAA ATT CTT CAC CAA GGA CAT ATT A    < 10200
     10150      10160      10170      10180      10190

TT GTG TCC AGA GGA AAT CAG ACA TGC TTG CAA GTT CGG GAT TGC TAA GGA TAA TAA TAA A    < 10260
     10210      10220      10230      10240      10250

GA CAT GAG CTA TCC CCC TTG GGG AAG GGA ATC CAG AGG GAC AAT TAC AAC AAT CCC TGT T    < 10320
     10270      10280      10290      10300      10310

TA TTA TAC GAC CAC CCC TTA CCC AAA GAT GCT AGA GAT GCC TCC AAG AAT CCA AAA TCC C    < 10380
     10330      10340      10350      10360      10370

CT GCT GTC CGG AAT CAG GTT GGG CCA ATT ACC AAC TGG CGC TCA TTA TAA AAT TCG GAG T    < 10440
     10390      10400      10410      10420      10430

AT ATT ACA TGG AAT GGG AAT CCA TTA CAG GGA CTT CTT GAG TTG TGG AGA CGG CTC CGG A    < 10500
     10450      10460      10470      10480      10490

GG GAT GAC TGC TGC ATT ACT ACG AGA AAA TGT GCA TAG CAG AGG AAT ATT CAA TAG TCT G    < 10560
     10510      10520      10530      10540      10550

TT AGA ATT ATC AGG GTC AGT CAT GCG AGG CGC CTC TCC TGA GCC CCG CAG TGC CCT AGA A    < 10620
     10570      10580      10590      10600      10610

AC TTT AGG AGG AGA TAA ATC GAG ATG TGT AAA TGG TGA AAC ATG TTG GGA ATA TCC ATC T    < 10680
     10630      10640      10650      10660      10670

GA CTT ATG TGA CCC AAG GAG TTG GGA CTA TTT CCT CCG ACT CAA AGC AGG CTT GGG GCT T    < 10740
     10690      10700      10710      10720      10730

CA AAT TGA TTT AAT TGT AAT GGA TAT GGA AGT TCG GGA TTC TTC TAG TAG CCT GAA AAT T    < 10800
     10750      10760      10770      10780      10790

GA GAC GAA TGT TAG AAA TTA TGT GCA CCG GAT TTT GGA TGA GCA AGG AGT TTT AAT CTA C    < 10860
     10810      10820      10830      10840      10850

AA GAC TTA TGG AAC ATA TAT TTG TGA GAG CGA AAA GAA TGC AGT AAC AAT CCT TGG TCC C    < 10920
     10870      10880      10890      10900      10910

AT GTT CAA GAC GGT CGA CTT AGT TCA AAC AGA ATT TAG TAG TTC TCA AAC GTC TGA AGT A    < 10980
     10930      10940      10950      10960      10970

TA TAT GGT ATG TAA AGG TTT GAA GAA ATT AAT CGA TGA ACC CAA TCC CGA TTG GTC TTC C    < 11040
     10990      11000      11010      11020      11030

AT CAA TGA ATC CTG GAA AAA CCT GTA CGC ATT CCA GTC ATC AGA ACA GGA ATT GCA GA     < 11100
     11050      11060      11070      11080      11090

GC AAA GAA GGT TAG TAC ATA CTT TAG CTT GAC AGG TAT TCC CTC CCA ATT CAT TCC TGA T    < 11160
     11110      11120      11130      11140      11150
```

-continued

```
CC TTT TGT AAA CAT TGA GAC TAT GCT ACA AAT ATT CGG AGT ACC CAC GGG TGT GTC TCA T    < 11220
       11170       11180       11190       11200       11210

GC GGC TGC CTT AAA ATC ATC TGA TAG ACC TGC AGA TTT ATT GAC CAT TAG CCT TTT TTA T    < 11280
       11230       11240       11250       11260       11270

AT GGC GAT TAT ATC GTA TTA TAA CAT CAA TCA TAT CAG AGT AGG ACC GAT ACC TCC GAA C    < 11340
       11290       11300       11310       11320       11330

CC CCC ATC AGA TGG AAT TGC ACA AAA TGT GGG GAT CGC TAT AAC TGG TAT AAG CTT TTG G    < 11400
       11350       11360       11370       11380       11390

CT GAG TTT GAT GGA GAA AGA CAT TCC ACT ATA TCA ACA GTG TTT AGC AGT TAT CCA GCA A    < 11460
       11410       11420       11430       11440       11450

TC ATT CCC GAT TAG GTG GGA GGC TGT TTC AGT AAA AGG AGG ATA CAA GCA GAA GTG GAG T    < 11520
       11470       11480       11490       11500       11510

AC TAG AGG TGA TGG GCT CCC AAA AGA TAG CCG AAT TTC AGA CTC CTT GGC CCC AAT CGG G    < 11580
       11530       11540       11550       11560       11570

AA CTG GAT CAG ATC TCT GGA ATT GGT CCG AAA CCA AGT CGT CTA AAT CCA TTC AAT GAG     < 11640
       11590       11600       11610       11620       11630

AT CTT GTT CAA TCA GCT ATG TCG TAC AGT GGA TAA TCA TTT GAA ATG GTC AAA TTT GCG A    < 11700
       11650       11660       11670       11680       11690

AA AAA CAC AGG AAT GAT TGA ATG GAT CAA TAG ACG AAT TTC AAA AGA AGA CCG GTC TAT A    < 11760
       11710       11720       11730       11740       11750

CT GAT GTT GAA GAG TGA CCT AGA CGA GGA AAA CTC TTG GAG AGA TTA AAA AAT CAT GAG G    < 11820
       11770       11780       11790       11800       11810
                                                  >VSV Trailer
                                                  |
AG ACT CCA AAC TTT AAG TAT GAA AAA AAC TTT GAT CCT TAA GAC CCT CTT GTG GTT TTT A    < 11880
       11830       11840       11850       11860       11870

TT TTT TAT CTG GTT TGG TCT TCG Tgg ccg gca tgg tcc cag cct cct cgc tgg cgc c        < 11940
       11890       11900       11910       11920       11930

>Hepatitis Delta Virus Ribozyme
            |
gg ctg ggc aac att ccg agg gga ccg tcc cct cgg taa tgg cga atg gga cct gct aac a    < 12000
       11950       11960       11970       11980       11990 aa gcc cga aag gaa gct gag ttg gct gct gcc acc gct gag caa taa cta gca taa ccc c    < 12060
       12010       12020       12030       12040       12050 tt ggg gcc tct aaa cgg gtc ttg agg ggt ttt ttg ctg aaa gga gga act ata tcc gga t    < 12120
       12070       12080       12090       12100       12110

>T7 Terminators
            |
gc ggc cga tcc ggc tgc taa caa agc ccg aaa gga agc tga gtt ggc tgc tgc cac cgc t    < 12180
       12130       12140       12150       12160       12170 ga gca ata act agc ata acc cct tgg ggc ctc taa acg ggt ctt gag ggg ttt ttt gct g    < 12240
       12190       12200       12210       12220       12230 aa agg agg aac tat atc cgg gtt aac ctg cat taa tga atc ggc caa cgc gcg ggg aga g    < 12300
       12250       12260       12270       12280       12290 gc ggt ttg cgt att ggg cgc tct tcc gct tcc tcg ctc act gac tcg ctg cgc tcg gtc g    < 12360
       12310       12320       12330       12340       12350 tt cgg ctg cgg cga gcg gta tca gct cac tca aag gcg gta ata cgg tta tcc aca gaa t    < 12420
       12370       12380       12390       12400       12410 ca ggg gat aac gca gga aag aac atg tga gca aaa ggc cag caa aag gcc agg aac cgt a    < 12480
       12430       12440       12450       12460       12470 aa aag gcc gcg ttg ctg gcg ttt ttc cat agg ctc cgc ccc cct gac gag cat cac aaa a    < 12540
       12490       12500       12510       12520       12530 at cga cgc tca agt cag agg tgg cga aac ccg aca gga cta taa aga tac cag gcg ttt c    < 12600
       12550       12560       12570       12580       12590 cc cct gga agc tcc ctc gtg cgc tct cct gtt ccg acc ctg ccg ctt acc gga tac ctg t    < 12660
       12610       12620       12630       12640       12650
```

```
cc gcc ttt ctc cct tcg gga agc gtg gcg ctt tct caa tgc tca cgc tgt agg tat ctc a    < 12720
      12670           12680           12690           12700           12710 gt tcg gtg tag gtc gtt cgc tcc aag ctg ggc tgt gtg cac gaa ccc ccc gtt cag ccc g    < 12780
      12730           12740           12750           12760           12770 ac cgc tgc gcc tta tcc ggt aac tat cgt ctt gag tcc aac ccg gta aga cac gac tta t    < 12840
      12790           12800           12810           12820           12830 cg cca ctg gca gca gcc act ggt aac agg att agc aga gcg agg tat gta ggc ggt gct a    < 12900
      12850           12860           12870           12880           12890 ca gag ttc ttg aag tgg tgg cct aac tac ggc tac act aga agg aca gta ttt ggt atc t    < 12960
      12910           12920           12930           12940           12950 gc gct ctg ctg aag cca gtt acc ttc gga aaa aga gtt ggt agc tct tga tcc ggc aaa c    < 13020
      12970           12980           12990           13000           13010 aa acc acc gct ggt agc ggt ggt ttt ttt gtt tgc aag cag cag att acg cgc aga aaa a    < 13080
      13030           13040           13050           13060           13070 aa gga tct caa gaa gat cct ttg atc ttt tct acg ggg tct gac gct cag tgg aac gaa a    < 13140
      13090           13100           13110           13120           13130 ac tca cgt taa ggg att ttg gtc atg aga tta tca aaa agg atc ttc acc tag atc ctt t    < 13200
      13150           13160           13170           13180           13190
                                                                              >pSP72
                                                                              |
ta aat taa aaa tga agt ttt aaa tca atc taa agt ata tat gag taa act tgg tct gac a    < 13260
      13210           13220           13230           13240           13250 gt tac caa tgc tta atc agt gag gca cct atc tca gcg atc tgt cta ttt cgt tca tcc a    < 13320
      13270           13280           13290           13300           13310 ta gtt gcc tga ctc ccc gtc gtg tag ata act acg ata cgg gag ggc tta cca tct ggc c    < 13380
      13330           13340           13350           13360           13370 cc agt gct gca atg ata ccg cga gac cca cgc tca ccg gct cca gat tta tca gca ata a    < 13440
      13390           13400           13410           13420           13430 ac cag cca gcc gga agg gcc gag cgc aga agt ggt cct gca act tta tcc gcc tcc atc c    < 13500
      13450           13460           13470           13480           13490 ag tct att aat tgt tgc cgg gaa gct aga gta agt agt tcg cca gtt aat agt ttg cgc a    < 13560
      13510           13520           13530           13540           13550 ac gtt gtt gcc att gct aca ggc atc gtg gtg tca cgc tcg tcg ttt ggt atg gct tca t    < 13620
      13570           13580           13590           13600           13610 tc agc tcc ggt tcc caa cga tca agg cga gtt aca tga tcc ccc atg ttg tgc aaa aaa g    < 13680
      13630           13640           13650           13660           13670 cg gtt agc tcc ttc ggt cct ccg atc gtt gtc aga agt aag ttg gcc gca gtg tta tca c    < 13740
      13690           13700           13710           13720           13730 tc atg gtt atg gca gca ctg cat aat tct ctt act gtc atg cca tcc gta aga tgc ttt t    < 13800
      13750           13760           13770           13780           13790 ct gtg act ggt gag tac tca acc aag tca ttc tga gaa tag tgt atg cgg cga ccg agt t    < 13860
      13810           13820           13830           13840           13850 gc tct tgc ccg gcg tca ata cgg gat aat acc gcg cca cat agc aga act tta aaa gtg c    < 13920
      13870           13880           13890           13900           13910 tc atc att gga aaa cgt tct tcg ggg cga aaa ctc tca agg atc tta ccg ctg ttg aga t    < 13980
      13930           13940           13950           13960           13970 cc agt tcg atg taa ccc act cgt gca ccc aac tga tct tca gca tct ttt act ttc acc a    < 14040
      13990           14000           14010           14020           14030 gc gtt tct ggg tga gca aaa aca gga agg caa aat gcc gca aaa aag gga ata ggg cg a    < 14100
      14050           14060           14070           14080           14090 ca cgg aaa tgt tga ata ctc ata ctc ttc ctt ttt caa tat tat tga agc att tat cag g    < 14160
      14110           14120           14130           14140           14150 gt tat tgt ctc atg agc gga tac ata ttt gaa tgt att tag aaa aat aaa caa ata ggg g    < 14220
      14170           14180           14190           14200           14210
```

```
                                -continued
tt ccg cgc aca ttt ccc cga aaa gtg cca cct gac gtc                                < 14258
       14230        14240        14250
```

| Features: | |
|---|---|
| T7-g10 Promoter | [1:49] |
| Hammerhead Ribozyme | [50:107] |
| VSV Leader | [108:170] |
| N | [171:1439] |
| P | [1503:2300] |
| M | [2360:3049] |
| Env.BG505 immunogen | [3198:5357] |
| L | [5479:11808] |
| VSV Trailer | [11809:11907] |
| Hepatitis Delta Virus Ribozyme | [11913:11991] |
| T7 Terminators | [11992:12260] |
| pSP72 | [12261:14258] |

Example 1: VSVΔG-Env.BG505 Vaccine—Live Attenuated VSV-HIV Chimera Delivering Env Trimers Vesicular stomatitis virus (VSV) has been modified to generate a live chimeric virus vaccine (VSVΔG-Env.BG505) for active immunization against HIV. The replication-competent recombinant chimera delivers a functional HIV Env glycoprotein trimer (clade A.BG505) in the context of viral replication mimicking native HIV spike presentation during an HIV infection.

Figures 1A, 1B, 1C:
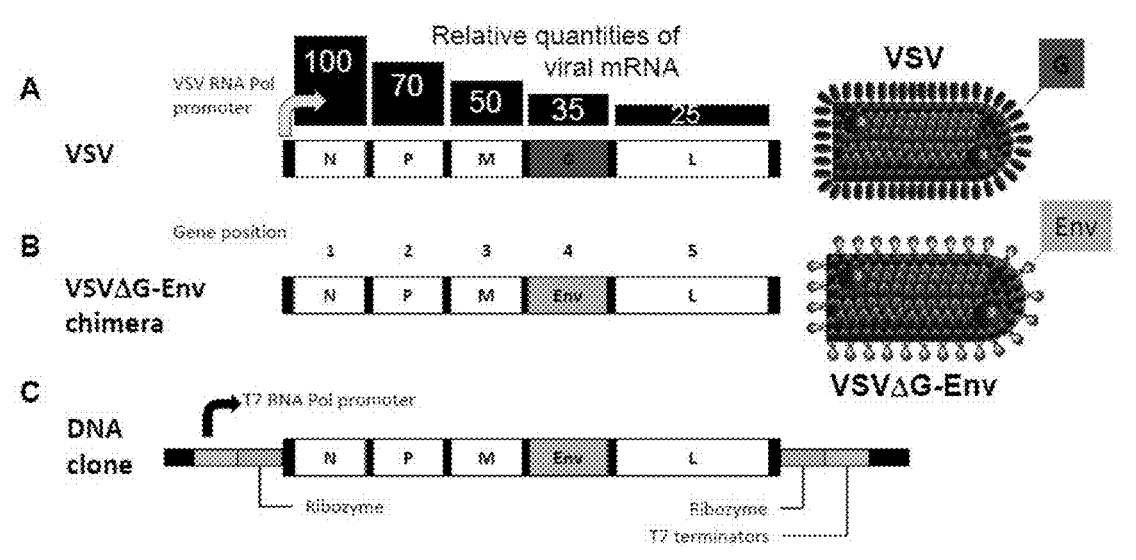

The VSVΔG-Env.BG505 chimera was constructed by replacing the natural VSV glycoprotein (G) gene with coding sequence for Env.BG505 (FIG. 1). As a result, Env is the

SEQ ID NO: 2

```
1   mkcllylafl figvnckasa enlwvtvyyg vpvwkdaett lfcadakay  etekhnvwat 61  hacvptdpnp qeihlenvte efnmwknnmv eqmhtdiisl wdqslkpcvk ltplcvtlqc 121 tnvtnnitdd mrgelkncsf nmttelrdkk qkvyslfyrl dvvqinenqg nrsnnsnkey 181 rlincntsai tqacpkvsfe pipihycapa gfailkckdk kfngtgpcps vstvqcthgi 241 kpvvstqlll ngslaeeevm irsenitnna knilvqfntp vqinctrpnn ntrksirigp 301 gqafyatgdi igdirgahct vskatwnetl gkvvkqlrkh fgnntiirfa nssggdlevt 361 thsfncggef fycntsglfn stwisntsvq gsnstgsnds itlperikqi inmwqrigqa 421 myappiqgvi rcvsnitgli ltrdggstns ttetfrpggg dmrdnwrsel ykykvvkiep 481 lgvaptrakr rvvgrekrav gigavflgfl gaagstmgaa smtltvgarn llsgivqqqs 541 nllraieagq hllkltvwgi kqlqarvlav erylrdqqll giwgcsgkli cttnvpwnss 601 wsnrnlseiw dnmtwlqwdk eisnytqiiy glleesqnqq ekneqdllal dkwaslwnwf 661 disnwlwyik ssiasfffii gliiglflvl rvgiylcikl khtkkrqiyt diemnrlgk VSV G signal peptide Ala-Ser amino acid linker Env.BG505 ectodomain VSV G transmembrane region VSV G cytoplasmic tail
```

It is to be understood and expected that variations in the principles of invention as described above may be made by one skilled in the art and it is intended that such modifications, changes, and substitutions are to be included within the scope of the present invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

only transmembrane glycoprotein encoded by the chimera, and virus propagation and spread is dependent on expression of functional Env trimers and infection of CD4+/CCR5+ cells.

VSVΔG-Env.BG505 is generated from a VSV genomic DNA clone that was developed from a lab-adapted strain of VSV (Indiana serotype). The genomic sequence is similar, but not identical, to the VSV genomic clone developed at Yale University (1), which is used for other VSV-based vaccine candidates including the attenuated VSV-N4CT1 vector developed by Profectus and NIAID (2), and the VSVΔG-Ebola virus chimera developed by the National Microbiology Laboratory in Canada (3), NewLink Genetics, and Merck Vaccines (4-6). About 100 nucleotides out 11 kb differ between the Yale and IAVI genomic clones.

Live VSVΔG-Env.BG505 is recovered from plasmid DNA by electroporating cells with the modified VSV genomic clone (FIG. 1C), a plasmid encoding T7 RNA polymerase to synthesize genomic RNA copies, and five plasmids that provide VSV polypeptides (N, P, M, G, L) in trans to initiate virus replication (9). The virus rescue protocol does not require proprietary transfection reagents or helper virus, and it has been optimized for use with Vero cell substrates (protocol adapted from (10, 11)). Recovery of infectious VSVΔG-Env.BG505 can be initiated by electroporating plasmids into Vero cells derived from a qualified cell bank (cells from Meridian Life Science, Inc. are used at IAVI), after which the virus must be propagated in cells that express CD4 and CCR5 to support Env-dependent replication. Thus, recombinant virus amplification, clonal isolation, virus seed preparation, and vaccine production is performed with a modified Vero cell line that contains the genes for human CD4 and CCR5 (VeroCD4/CCR5).

Applicants developed a stable VeroCD4/CCR5 cell line for propagation of the VSVΔG-Env.BG505 chimera. The cell line used in the lab currently encodes human CD4 and CCR5 and was developed under research conditions starting with cells obtained from the Meridian Life Science qualified Vero cell bank. The research VeroCD4/CCR5 cell line is stable and has been used for several years to support work on VSVΔG-Env.BG505 and a number of similar chimeric viruses. Yields of VSVΔG-Env.BG505 produced in VeroCD4/CCR5 monolayers typically are $>1\times10^7$ pfus per ml of harvested culture medium. Work on deriving a new cell line has been initiated for the purpose of generating VeroCD4/CCR5 cells that will meet requirements associated with future VSVΔG-Env.BG505 cGMP manufacturing. As used herein, VeroCD4/CCR5 and VERT or VERT3 are used interchangeably.

The VSVΔG-Env.BG505 vaccine tested in rhesus macaques contained 'pseudotyped' (12) virus particles to enhance vaccine uptake and promote a vigorous initial round of infection and replication. When virus was grown to produce a batch of vaccine, infection was conducted under conditions in which the VSV G glycoprotein was transiently expressed in VeroCD4/CCR5 cells allowing production of particles containing G. An efficient laboratory method was developed to simplify addition of the G pseudotype. A suspension of VeroCD4/CCR5 cells is mixed with plasmid DNA encoding G and VSVΔG-Env.BG505 particles after which the mixture is subjected to electroporation. The electroporated cells are then distributed into cell factories containing culture medium. Virus is harvested and purified 48 hours post-electroporation.

Two points about G pseudotyping and the VSVΔG-Env.BG505 vaccine are worth emphasizing. First, VSVΔG-Env.BG505 does not contain the G gene; thus, infected cells do not express G and the VSV glycoprotein is present only in pseudotyped virus particles used for vaccination. Following vaccination, progeny VSVΔG-Env.BG505 particles produced by the first round of replication will lack the G glycoprotein making all subsequent rounds of infection dependent on HIV Env and infection of CD4+/CCR5+ cells of lymphoid origin. Because G is present only transiently (FIG. 2), it cannot promote spread of infection to other types of cells and tissues (i.e. neurons in the central nervous system).

The second point is related to the benefit of the pseudotyping. It is well established that G is a very effective virus attachment protein, which has been used to pseudotype a variety of different candidate viral vaccines, gene therapy vectors, and oncolytic agents (12-15). A positive effect of pseudotyping on immunogenicity of a prototype VSVΔG-SIV Env chimera was demonstrated experimentally in a small pilot macaque study in which animals were vaccinated mucosally (combination of oral and nasal cavity) with a vaccine prepared with and without a G pseudotype. In animals vaccinated with pseudotyped virus particles, anti-SIV Env antibody titers were greater than 100-fold higher (FIG. 5). Moreover, the transient exposure to G in the virus inoculumn did not elicit significant titers of anti-G antibodies (data not shown).

Many different glycoproteins may be used to pseudotype VSV particles besides G. Alternative pseudotypes may be useful for targeting vaccine delivery to different areas. Examples include F plus H from morbilliviruses, the F and HN from various parainfluenza viruses, the F and G from various pneumoviruses, the F plus HN from various rubulla viruses. Also, the glycorpteins from filoviruses or arena viruses, among others.

Although the efficacious VSVΔG-Env.BG505 vaccine was a pseudotyped particle, it is important to note that studies have not yet been done in macaques to assess whether pseudotyping contributes to vaccine efficacy. Furthermore, G was selected for pseudotyping because it was known to be highly effective, but other alternative viral glycoproteins can be used if it becomes necessary to develop a pseudotyped vaccine that targets a more limited cell population.

The VSVΔG-Env.BG505 vaccine was designed to deliver authentic HIV envelope (Env) trimers mimicking the presentation of Env spikes by HIV infection or a live attenuated HIV vaccine. As designed, the replication competent chimeric virus provides several important immunostimulants once administered, including: 1) innate signaling initiated by infection and replication of an RNA virus; 2) infected cells containing Env incorporated in the cell surface membrane; and 3) progeny virus particles containing Env spikes arrayed on their surface. Moreover, like HIV or SIV, Env-dependent VSVΔG-Env.BG505 propagation in vivo might contribute to vaccine efficacy by providing more persistent antigen exposure and immune stimulation that is associated with infection occurring in lymphoid tissues (16, 17).

VSVΔG-Env.BG505 is designed to propagate using Env as its attachment and entry protein. This has several important consequences during chimeric virus replication in the vaccinee, including: 1) there is strong selective pressure to maintain the gene encoding functional Env; 2) it ensures that the replicating chimeric virus will present the immune system with authentic Env spike targets; and 3) because Env is functional and incorporated in the membrane, it has the conformational flexibility of a native spike and will expose the immune system with a full range of authentic antigenic determinants. Related to the last point, it also is important to emphasize that the functional Env.BG505 trimer expressed by VSVΔG-Env.BG505 is not a conformationally constrained trimer like some other experimental vaccines that have been develop recently like Env.BG505 SOSIP or Env.BG505 NFL described by others (18, 19).

Figures 3A, 3B:
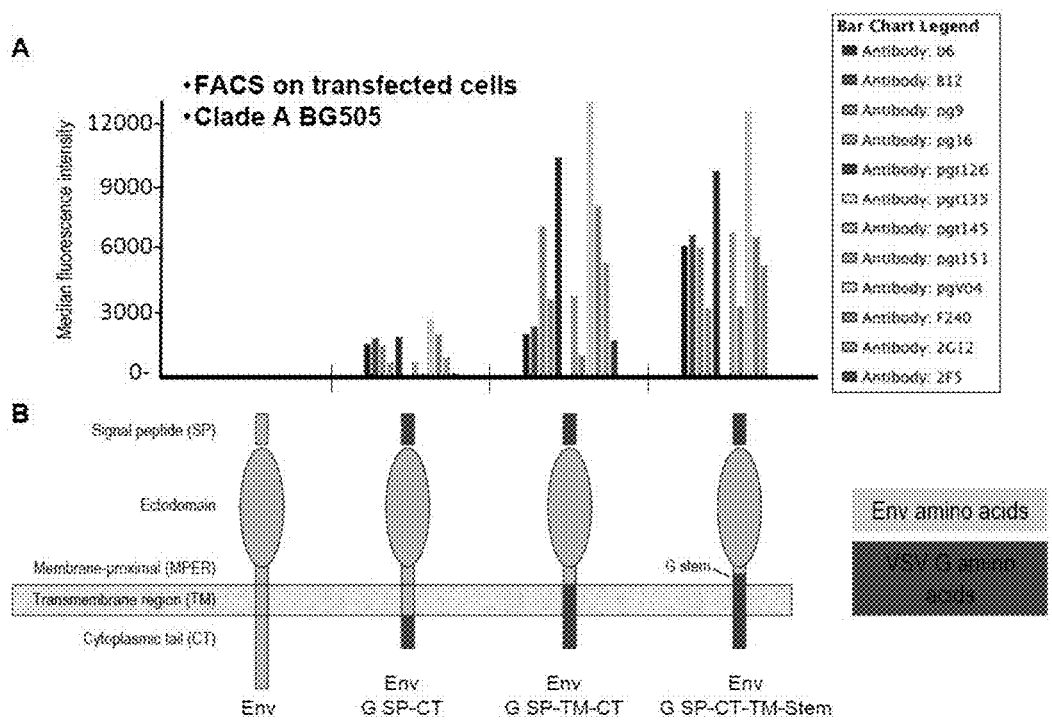
FIGS. 3A-3B. Improvement of Env spike surface expression. A) Flow cytometry conducted with transfected 293T cells expressing modified Envs. Monoclonal bnAbs used for detection are indicated at the right. Notably, antibodies PG16, PGT151, and PGT145 preferentially react with epitopes that are formed by well-ordered trimers. The linear structure of the corresponding Env-G hybrids (B) is shown below the flow cytometry data in Part A. SP, signal peptide, which is cleaved during translational processing; TM, transmembrane; CT, cytoplasmic tail; MPER, the Env membrane proximal external region; G stem; membrane proximal external region of G.

Rose and colleagues first demonstrated that it was feasible to generate an infectious VSVΔG-Env chimera using a clade B Env (23), but additional development was necessary to advance an effective vaccine candidate. First, the Env.BG505 immunogen was selected specifically because it was known to have a broad antigenicity profile (24) and it was isolated from an infected infant that produced bnAbs (25, 26). Second, it was necessary to investigate Env modifications for a number of reasons, including 1) to ensure Env gene genetic stability; 2) to enable vigorous replication in cell culture that would support vaccine production; and 3) to substantially increase Env incorporation into to the infected cell membrane and virus particle to provide improved display of Env spike immunogens. Following an approached suggested by earlier data showing that the Env cytoplasmic tail caused vector genetic instability (unpublished and (27)) and suppressed incorporation into VSV particles (28), a number of hybrid Envs were designed and evaluated (FIG. 3) in which various combinations of the Env signal peptide (SP), transmembrane (TM) region, and cytoplasmic tail (CT) were replaced with sequence from VSV G (Indiana serotype). A hybrid Env containing the VSV G SP, TM and CT was found to be expressed abundantly on the cell surface of transfected cells and also was found to support efficient Env-dependent replication of the VSVΔG-Env.BG505 chimera in CD4+/CCR5+ cells. A hybrid in which the Env membrane-proximal external region (MPER) also was replaced with the analogous 'Stem' domain of G was expressed in modestly greater quantities on the surface of transfected cells, but since it lacked the important Env MPER epitope, all subsequent vector design has focused on the Env hybrids where the SP, TM, and CT are substituted with VSV G sequences. Therefore, the VSVΔG-Env.BG505 vaccine encodes a highly expressed Env-G hybrid, which is designed so that all sequence displayed on the membrane surface is Env ectodomain while intracellular and membrane-spanning sequences are derived from G.

Figure 4A:
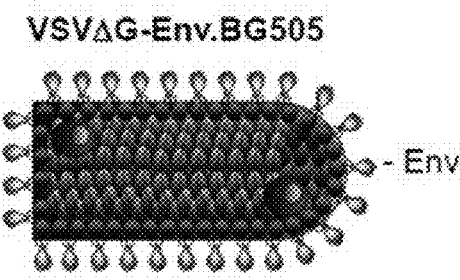
FIGS. 4A-4C. Antigenicity of Env.BG505 trimers delivered with VSVΔG-Env.BG505. Chimeric virus particles containing Env.BG505 Env only (A) were used for analyses in panels C-D. In B, infected VeroCD4/CCR5 were analyzed by flow cytometry using antibodies listed on the X-axis. In C, purified virus was adsorbed to alum after which the alum-virus complexes were reacted with mAbs and analyzed by flow cytometry. The asterisks in B and C highlight antibodies that preferentially recognized well order trimers.
Figure 4B:
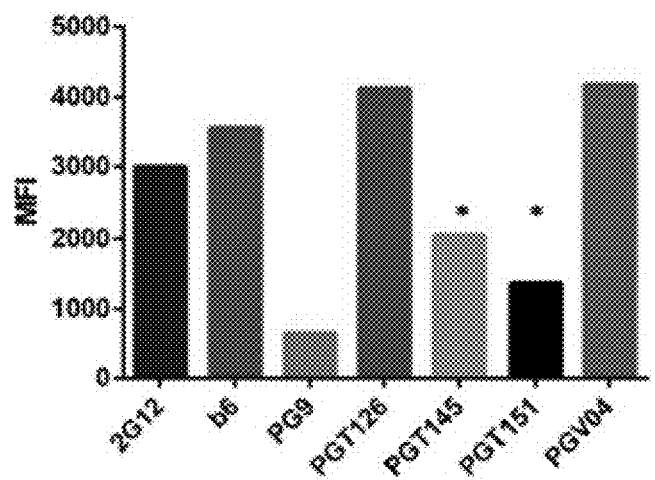
Figure 4C:
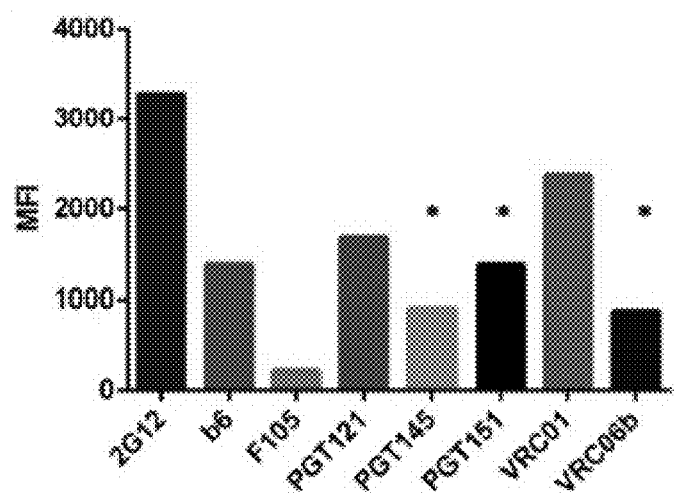

The Env-G hybrid immunogen incorporated on the surface of infected cells and VSVΔG-Env.BG505 particles is broadly antigenic. An example of infected cells analyzed by flow cytometry (FIG. 4B) shows that multiple mAbs bind the cell surface including PGT145, PGT151 and VRC06, which bind preferentially to determinants formed by well-ordered trimmers (19, 21, 22). Similarly, bnAbs recognize purified virions when they are adsorbed to alum and the alum-virus complexes are analyzed by flow cytometry (FIG. 4D), which agrees with electron microscope images (FIG. 4C) showing surface density consistent with the present of glycoprotein complexes on the surface of VSVΔG-Env.BG505 particles.

Part of the vaccine design objective was to develop a chimeric virus that could be administered effectively by a mucosal route to stimulate immune protection at the mucosal barrier. Even though a mucosal barrier is advantageous, Applicants do not envision the vaccine to be limited to this route of administration. Because research and development on lentivirus virus vectors has shown that Env is not an effective attachment protein for virus particle delivery, VSVΔG-Env.BG505 modifications were considered that might significantly improve virus uptake without changing the key feature of the chimeric virus, which is its unique design in which Env is the sole glycoprotein expressed following infection. Thus, rather than genetically modifying the VSVΔG-Env.BG505 vector further, a decision was made to test vaccines in which the virus particles were prepared with a G pseudotype, as a considerable body of work on lentiviruses (12) as well as a variety of chimeric VSV vectors (29) showed that pseudotyping with G was effective.

To support testing of a pseudotyped VSVΔG-Env vaccine, a simple system was developed to add G to virus particles. Briefly, a suspension of VeroCD4/CCR5 cells is mixed with plasmid DNA encoding G and VSVΔG-Env.BG505 particles and then mixture is subjected to electroporation. The electroporated cell suspension is then distributed into cell stacks and cultured for ~48 hours after which pseudotyped virus particles are harvested and purified. The efficiency of pseudotyping can then be quantified by evaluating plaque formation on CD4+/CCR5+ cell monolayers in which Env or G can direct infection, and comparing this to G-mediated infection of standard Vero monolayers, which support a single-cycle of infection that can be quantified by immunostaining to detect individual cells expressing viral proteins.

Figures 5A, 5B, 5C:
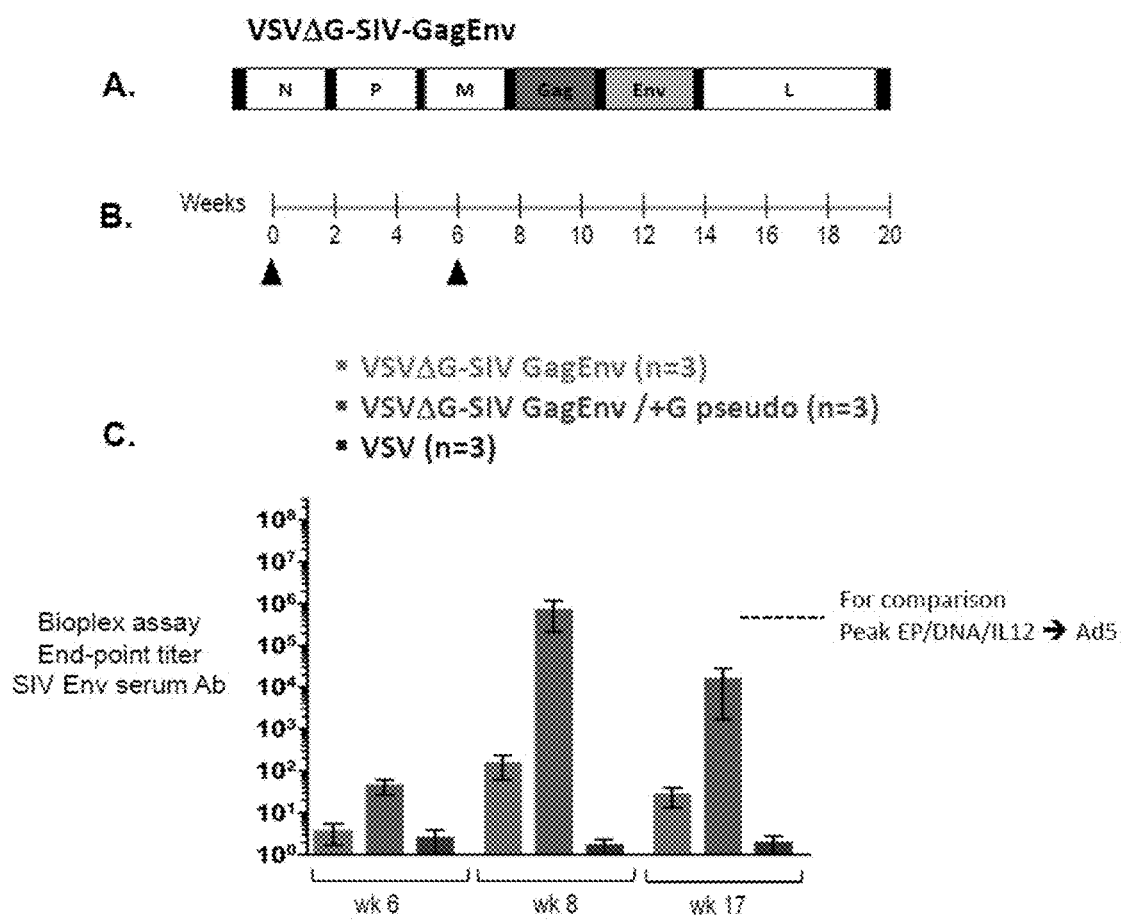
FIGS. 5A-5C. Anti-Env antibodies elicited by mucosal vaccination with a VSVΔG-SIV chimeric virus vaccine prototype. A) Genome map of the VSVΔG-SIV-GagEnv chimera, which contains the SIV Gag and Env genes. B) Three groups of animals (3 per group) were vaccinated with VSVΔG-SIV-GagEnv, VSVΔG-SIV-GagEnv prepared with a G pseudotype, or a negative control, which was live recombinant VSV. Animals were vaccinated twice (0 and 6 weeks) with $2\times10^8$ pfus. Live virus in buffered solution was administered in drops applied to the nasal and oral cavities ($1\times10^8$ pfu per site). C) Anti-SIV Env serum antibody titers were quantified by bioplex assay. To the right side of the chart, the peak antibody titer elicited in an earlier study with a DNA-SIV Env prime (electroporation) and Ad5-SIV Env boost is indicated with a dotted line for comparison. Assay background is subtracted from the data presented in the graph.

A pilot study was conducted in Indian rhesus macaques with a prototype VSVΔG-SIV chimera (FIG. 5A, VSVΔG-SIV-GagEnv). Macaques were used for this early study because transgenic or 'humanized' small animal models that can support replication of a CD4/CCR5-tropic virus have limitations. The macaque study was conducted for three primary reasons: 1) assess the ability to safely vaccinate mucosally in the nasal and oral cavity with a chimeric virus; 2) detect and quantify serum anti-Env antibodies elicited by mucosal vaccination; and 3) compare vaccines prepared with and without a G pseudotype.

Macaques were vaccinated (FIG. 5B) at weeks 0 and 6 by applying virus solution to the nasal and oral cavities ($1 \times 10^8$ pfus per site). Importantly, animal behavior was normal following vaccination and no lesions were observed in or around the nose or mouth. Quantification of antibody titers by bioplex assay (30) showed that the chimeric virus vaccines were immunogenic and that the pseudotyped vaccine was significantly more potent. Following the first vaccination, samples analyzed at week 6 showed that the pseudotyped VSVΔG-SIV-GagEnv vaccine elicited low but detectable antibody titers, while animals vaccinated with an 'empty' VSV vector or the chimeric virus lacking the G pseudotype had values near baseline. Env antibody titers increased after homologous boost at week 6, and it was clear that the peak titer elicited by the pseudotyped chimera was considerably stronger (>1,000×) compared to the magnitude of the response generated by the vaccine lacking the G pseudotype, and the titers also remained substantial >2.5 months after the week-6 boost. It also is worth highlighting that two mucosal vaccinations with the pseudotyped VSVΔG-SIV-GagEnv vaccine generated antibody titers that were in the same range as peak responses seen with a relatively potent vaccination regimen based on 3×DNA-SIV-Env prime (intramuscular electroporation) and Ad5-SIV Env (intramuscular) boost (31).

Several conclusions were drawn from this pilot study. First, the chimeric virus vaccine was able to safely elicit anti-Env antibodies against a membrane anchored Env spike. Second, antibody titers of this magnitude elicited by mucosal vaccination indicated that the VSVΔG-SIV chimera replicated following vaccination and that the antibody response was not elicited simply by exposure to the virus particles delivered in a buffered solution. This assumption also is consistent with the fact that G in the pseudotyped particles did not elicit an anti-G response significantly above background in an ELISA (data not shown). Finally, it was evident that the chimeric virus vaccine prepared with the G pseudotype was more potent, thus the HIV vaccine based on VSVΔG-Env.BG505 was advanced for testing in macaques as a pseudotyped vaccine.

The preclinical efficacy of the VSVΔG-Env.BG505 vaccine prepared with a G pseudotype is being evaluated in Indian rhesus macaques using the rectal SHIV challenge model. The study was designed with the three main objectives: 1) show that the VSVΔG-Env.BG505 chimera could be administered safely to the nasal and oral cavities; 2) demonstrate that vaccination elicits anti-Env antibodies; and 3) establish that vaccination provides measurable protection from rectal exposure with a heterologous clade B SHIV (SHIV SF162p3).

Figures 6A, 6B, 6C:
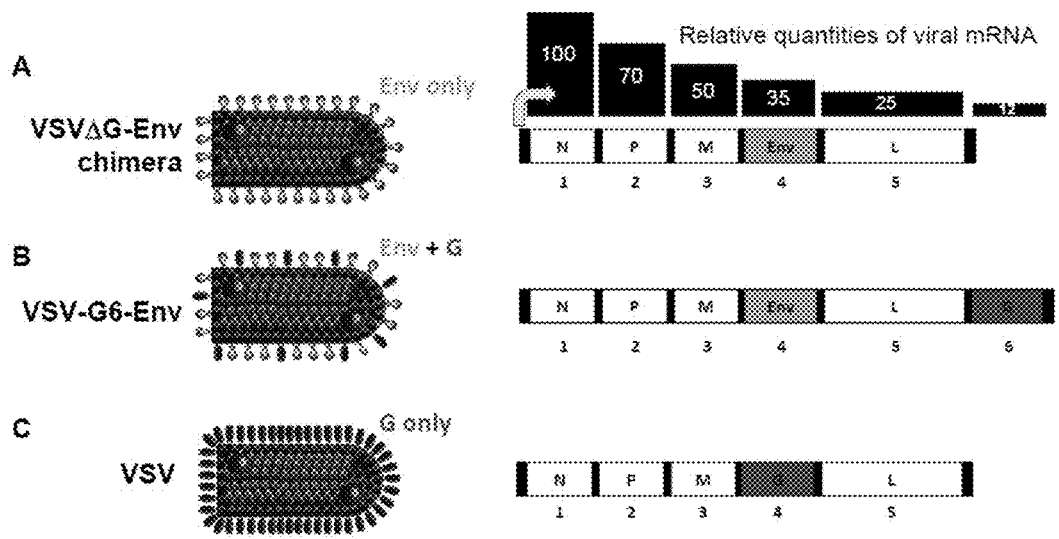
FIGS. 6A-6C. Genome maps comparing VSVΔG-Env.BG505 and an alternative vector design, VSV-G6-Env.BG505. A) The VSVΔG-Env.BG505 chimera genome contains 5 genes with Env.BG505 coding sequence inserted in place of G (position 4, also see FIG. 1). Gene expression declines with increasing distance from the transcriptional promoter located at the left end (yellow arrow, and see FIG. 1). The VSVΔG-Env.BG505 particle is illustrated with only Env incorporated on the surface, which is representative of the progeny virus particles that will be produced as the vector replicates in the vaccinee. B) In the VSV-G6-EnvBG505 vector, the G gene was reintroduced, but placed in position 6, which down-regulates G expression and enables stable coexpression of both glycoproteins. C) VSV schematic for comparison to the two vectors illustrated above.

The study also included a head-to-head comparison with a second VSV vector encoding the same Env.BG505 trimer immunogen. The main purpose of this comparison was to evaluate an alternative Env.BG505 delivery vector (VSV-G6-Env.BG505, FIG. 6) that would have increased replicative capacity in vivo. To achieve greater replicative capacity, the VSV-G6-Env.BG505 vector was designed to contain genes encoding Env.BG505 and G; therefore, the vector coexpresses the glycoproteins in infected cells, and incorporate both trimeric complexes in virus particles. As designed, the VSV-G6-Env.BG505 vector can propagate and spread in a wider range of cells in vivo because the continuous expression of G allows infection and spread into a much broader range of cell types. Thus, both the pseudotyped VSVΔG-Env.BG505 chimera and VSV-G6-Env.BG505 can infect most cell types at the site of vaccine administration using G, but after the initial round of replication, secondary infection initiated by progeny virus particles will be significantly different, with the VSVΔG-Env.BG505 targeted specifically to CD4+/CCR5+ cells and VSV-G6-Env.BG505 being able to spread into multiple cell types.

The preclinical efficacy study was designed with three groups of 10 macaques (negative for Mamu-B*08 and -B*17 MHC alleles associated with immune control) that were vaccinated at weeks 0, 4, and 29 with pseudotyped VSVΔG-Env.BG505, VSV-G6-Env.BG505 or a saline control. It is important to highlight that vaccination was conducted only with the live VSV vectors, and no boost was performed with a heterologous vaccine. Vaccines were administered by application to mucosal surfaces in the nasal and oral cavity of sedated animals ($1 \times 10^8$ pfus per site). No local lesions were observed and all macaques behaved normally after vaccination.

All macaques immunized with a VSV-based Env.BG505 vaccine developed detectable anti-Env serum antibodies after the second vaccination. The third vaccination at week 29 provided a boost, and perhaps more importantly, increased the durability of the antibody titiers, which persisted during the 5-month rest period before challenge in 8 out of 10 macaques vaccinated with VSVΔG-Env.BG505 and all animals vaccinated with VSV-G6-Env.BG505. The TZM-bl assay (33) also was used to analyse serum for virus-neutralizing antibodies (nAbs). The resulted showed that nAb titers were low (titers ≤100) and were detectable in only some vaccinated animals (summarized on the ELISA chart in FIG. 8). In macaques vaccinated with the VSVΔG-Env.BG505 chimera, 4 animals were positive for nAbs active against HIV SF162p3 pseudovirus at week 31, but the titers waned to undetectable by the day of SHIV challenge. Vaccination with VSV-G6-Env.BG505 elicited nAbs against SF162p3 and homologous BG505 pseudovirus that were detectable at week 31 and 48, but not in all animals.

Figure 7:
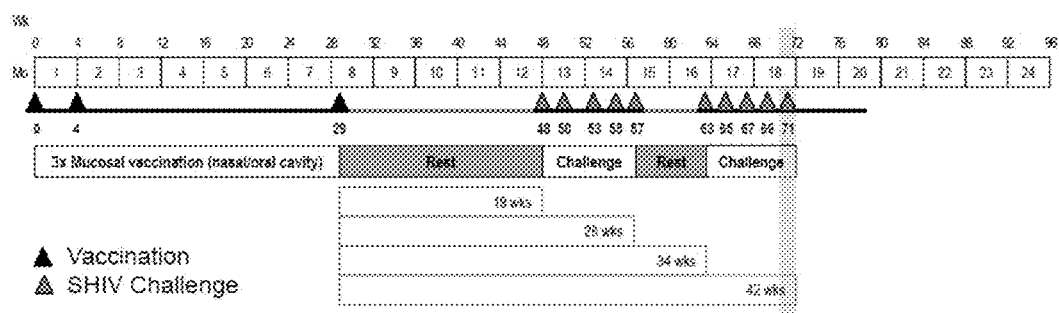
FIG. 7. Preclinical efficacy study design. Three groups of 10 Indian rhesus macaques were vaccinated according to the timeline at the top, which shows months and weeks. The three vaccine groups included: VSVΔG-Env.BG505 chimeria, VSV-G6-Env.BG505, and saline control. Vaccination and repeated rectal challenge time points are illustrated by filled triangles. Challenge was conducted with a heterologous clade B SHIV (SHIV SF162p3).
Figure 9:
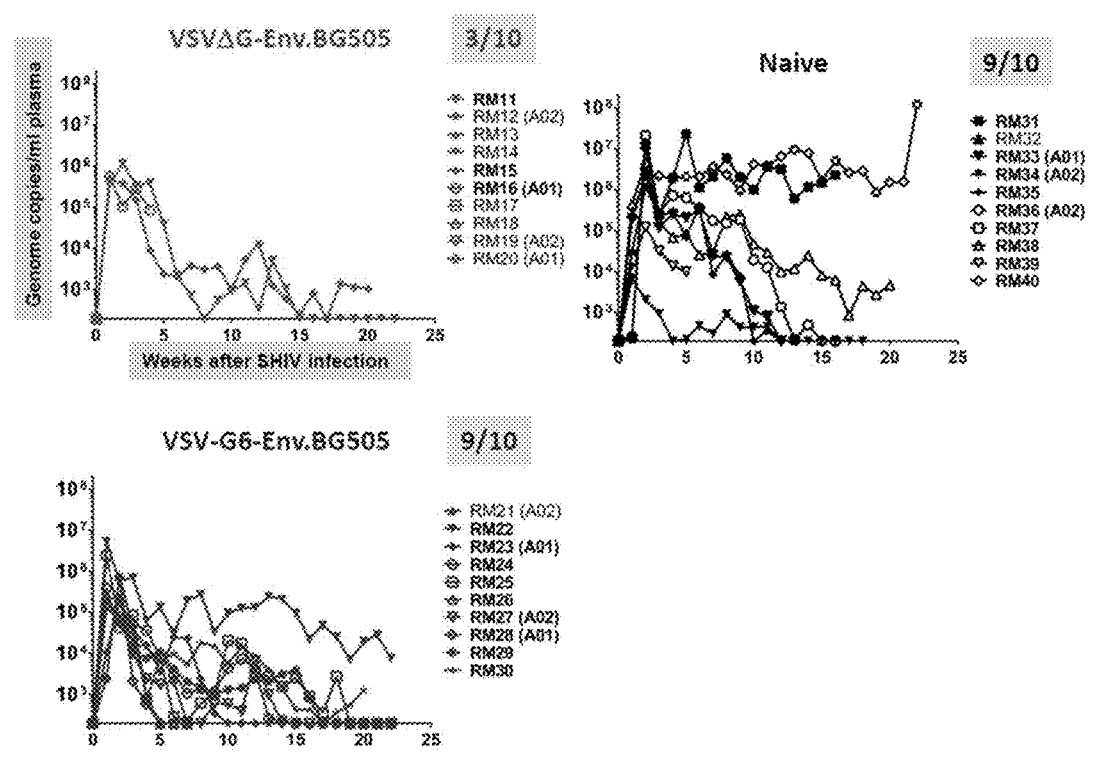

Clade B SHIV SF162p3 challenge commenced at week 48, which was about 5 months after the final vaccination (FIG. 7). The challenge protocol was composed of 3 stages: the first 5 rectal exposures conducted approximately every two weeks, a 6-week rest period, and the final 5 biweekly exposures. Macaques with ≥200 genome SHIV copies per ml of plasma were considered infected after which challenge was stopped. All infected macaques were viremic for weeks following the initial infection (FIG. 9) as determined by detection of SHIV genomes in the blood, and accordingly, the infected animals developed antibodies against Gag expressed by the SHIV (data not shown).

Figure 10:
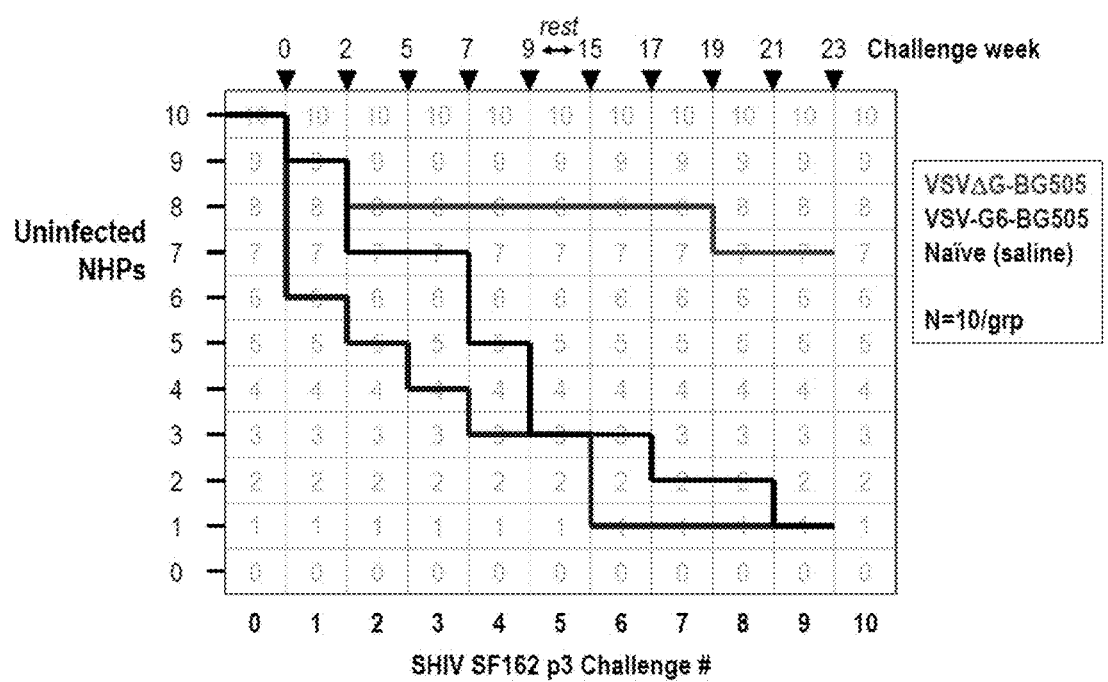
FIG. 10. SHIV infection rate during repetitive rectal challenge. As described in FIG. 7, three groups of 10 animals were vaccinated with VSVΔG-Env.BG505 (red line), VSV-G6-Env.BG505 (blue line), or saline (black line). About 5 months after the third vaccination at week 48, challenge commenced using $2.2\times10^4$ TCID50 per rectal inoculation (TCID50: tissue culture infectious dose required to produce cytopathic effect in 50% of inoculated cell cultures). The graph shows the number of uninfected animals (Y axis) per group prior to commencing the SHIV challenge protocol. SHIV challenge 10 has been completed.

The SHIV infection rate was significantly reduced in macaques vaccinated with the VSVΔG-Env.BG505 chimera compared to animals vaccinated with VSV-G6-Env.BG505 or saline control (FIG. 10). Over the course of 9 challenges, 9 out of 10 macaques in the Control and VSV-G6-Env.BG505 groups became chronically infected with SHIV at a similar frequency. In contrast, in macaques vaccinated with VSVΔG-Env.BG505, just 3 were infected with challenge virus indicating that VSΔG-Env.BG505 immunization significantly increased resistance to mucosal SHIV infection. Thus, vaccine efficacy as measured by prevention of rectal infection with a heterologous clade B SHIV was 67%.

Figure 8:
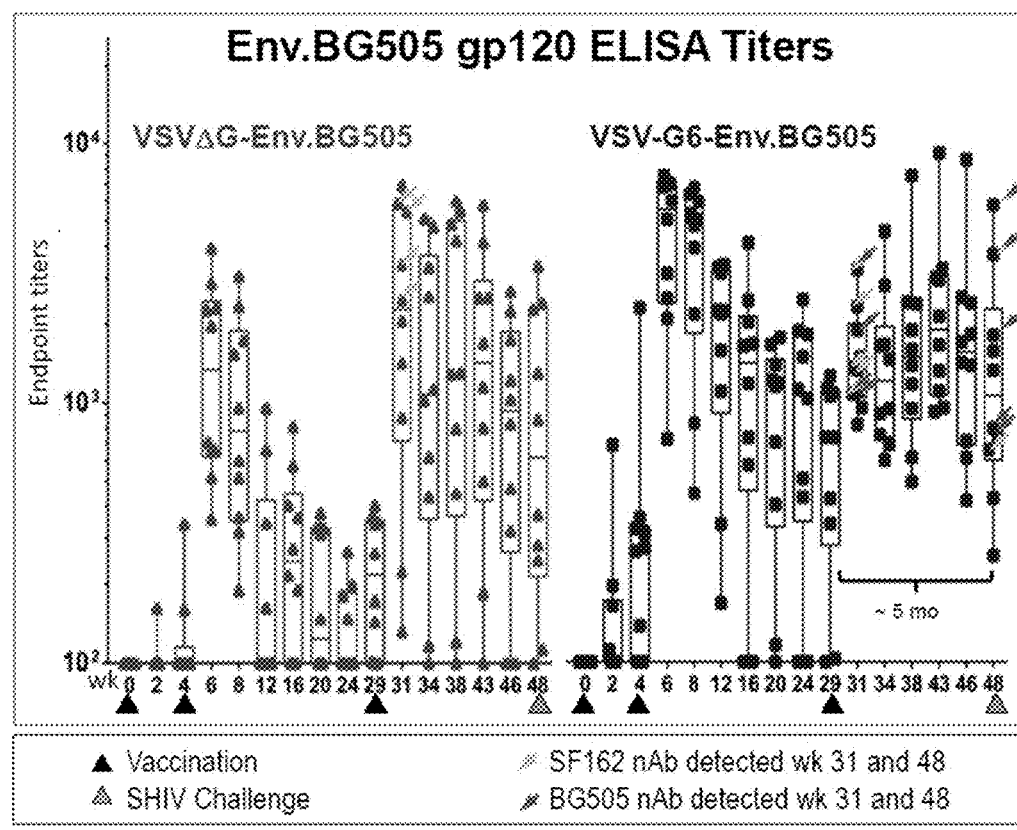
FIG. 8. Serum antibodies elicited by vaccination. Antibody binding to Env.BG505 gp120 was quantified by ELISA over the course of the vaccination phase. HIV pseudovirus neutralization assays also were conducted (data not shown) and samples with detectable neutralization activity against clade B SF162p3 or autologous clade A BG505 pseudovirions are identified with colored arrows.
Figure 11:
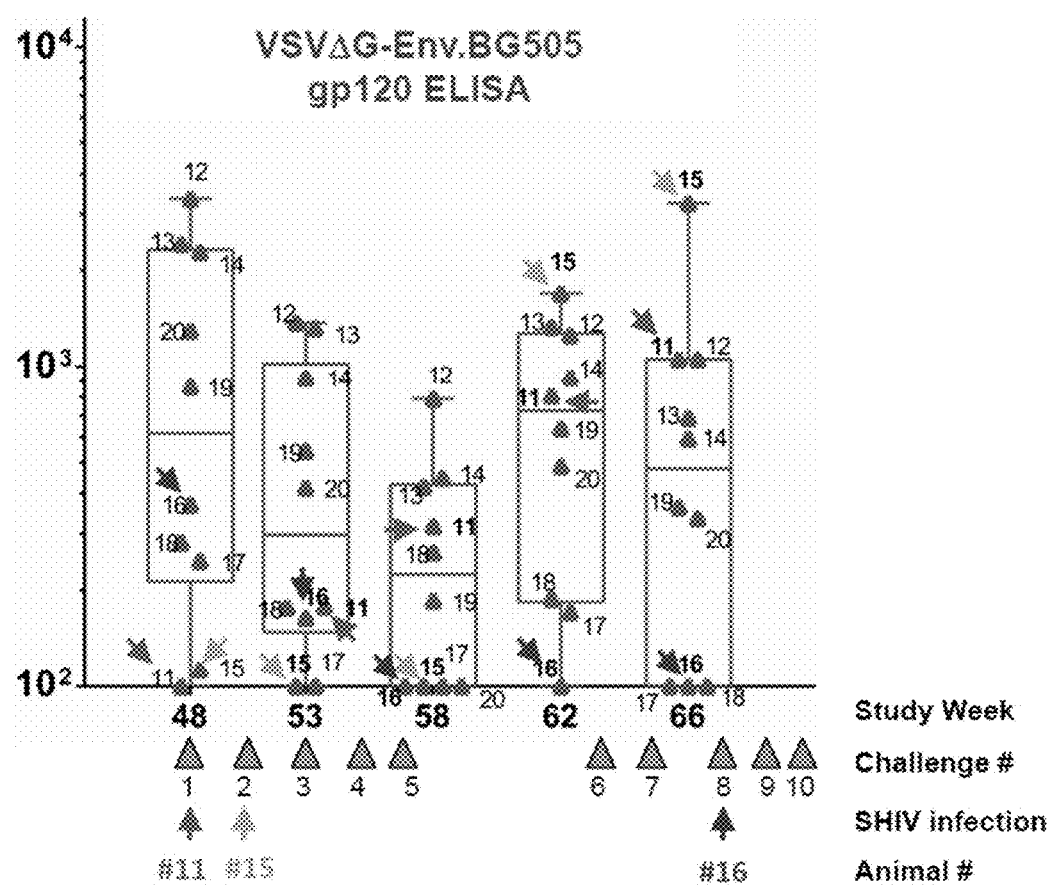
FIG. 11. Env.BG505 binding antibody titers at time of SHIV infection in animals vaccinated with VSVΔG-Env.BG505. ELISA was conducted with Env.BG505 gp120 bound to the plate using samples collected from macaques at the time challenge commenced (week 48) and periodically during the challenge protocol (FIG. 7). Animals 11 and 15 were infected at SHIV challenge 1 and 2, respectively. Animal 16 was infected at challenge 8, which was 19 weeks after the challenge protocol commenced. Colored arrows point to ELISA titers for animals 11, 15, and 16.

Immunologic assessment continues, but current results point to a potential relationship between the reduced frequency of infection seen in the animals vaccinated with the VSVΔG-Env.BG505 vaccine (FIG. 10) and Env-specific serum antibodies. First, both replication-competent VSV vectors elicited serum antibodies that persisted for the 5-month period between the final vaccination and the beginning of the repetitive SHIV challenge protocol (FIG. 8). In the animals vaccinated with VSVΔG-Env.BG505, there were 2 animals in which the antibody titers waned to baseline levels by week 48 when challenge commenced (FIG. 8), and interestingly, these were the same two animals that appeared least resistant in this group and became infected by challenge 2 (FIG. 10). The third animal that became infected in this group resisted 7 challenges conducted over a period of about 4.5 months, but became infected at exposure 8 by which time the serum antibody titers had waned. These results imply that there is a relationship between Env.BG505 gp120 binding antibody titers and SHIV infection resistance. This trend is summarized graphically in FIG. 11.

In contrast to the results seen in animals vaccinated with the VSVΔG-Env.BG505 chimera, that rate of infection in macaques vaccinated with VSV-G6-Env.BG505 was very similar to the control group indicating that vaccination did not have measurable effect on SHIV infection frequency (FIG. 10). This was observed even though all animals had developed Env antibodies in response to vaccination, including some macaques that had nAbs (FIG. 8).

Taken together, the results of vaccination with the different live VSV-based vectors show that both types of vaccine elicit Env antibodies, but that the quality of the antiviral immunity is very different. What is responsible for this difference in protection is not understood at this time, but perhaps it is related to antibody binding site specificity, the diversity of Env epitopes recognized, or IgG effector functions. Alternatively, the two live vectors might elicit different profiles of Env-specific T cells with antiviral activity that is affecting infection resistance. Ongoing and future immunologic assessment will help identify differences in the immune responses elicited by the two vaccines, which will provide guidance for vector and immunogen improvements.

The results produced with two different replicating VSV-based vaccines also illustrates clearly that specific vaccine design details can have a pronounced effect on efficacy. Some of the unique features of the VSVΔG-Env.BG505 vaccine that might contribute to efficacy, include; 1) CD4+/CCR5+ tropism that targets replication to lymphoid cells and tissues; 2) chimeric virus propagation in vivo that is dependent on expression of functional Env and will provide immune system exposure to authentic Env spikes; 3) the only glycoprotein expressed is Env, thus there is no other competing glycoprotein immunogen that might dominate immune responses; and 4) the lack of other vector-encoded glycoproteins eliminates development of potent anti-vector antibodies that might interfere with multiple immunizations.

Preclinical efficacy in the SHIV challenge model was observed following mucosal vaccination with a total dose of $2 \times 10^8$ pfu per ml. The vaccine dose was split between two sites. Mucosal surfaces in the nasal and oral cavities each received 1×10⁸ pfu applied in a buffered solution.

Preclinical efficacy in the SHIV challenge model was observed with a vaccination schedule of 0, 4, and 29 weeks. Other vaccination schedules are also contemplated.

Mucosal vaccination in the nasal and oral cavity was tested primarily because the goal was to stimulate enhanced mucosal immunity. Other considerations supporting this vaccination route included: 1) providing access to submucosal CD4+/CCR5+ lymphocytes that would be targets for VSVΔG-Env.BG505 replication, and 2) VSV naturally infects these mucosal sites.

VSVΔG-Env.BG505 is a recombinant chimeric virus based on the VSV Indiana serotype. The VSV G gene deleted and replaced with sequence encoding functional HIV Env.BG505. The live vaccine is replication competent and propagates specifically in cells that contain the CD4/CCR5 receptors.

The efficacious preclinical vaccine is a G-pseudotyped VSVΔG-Env.BG505 that is applied to nasal and oral cavity mucosal surfaces at 0, 4, and 29 weeks.

The VSVΔG-Env.BG505 vaccine is expected to be safe for use in humans, because 1) no observable adverse reactions occurred in vaccinated macaques, and 2) the chimeric virus design makes propagation dependent on Env, thus virus spread in vivo is restricted to lymphoid cell and tissues that express CD4 and CCR5 and will prevent virus replication in other sites like the central nervous system.

The preferred cell line for vaccine production is VeroCD4/CCR5, which has been used to support preclinical development of the VSVΔG-Env.BG505 chimeric virus vaccine. A similar cell line must be 'rederived' using conditions and materials that are consistent with using the cells for vaccine manufacturing. Manufacturing processes and steps are set forth in FIG. 12. Preparation of VSVΔG-Env.BG505 with G pseudotype is set forth in FIG. 13.

Preclinical material tested in macaques may be purified by 2 round of centrifugation through sucrose cushion and the method is based on tangential flow filtration.

Preclinical vaccine material is stored frozen (−80) in Hank's Balanced Salt Solution (HBSS) supplemented with 15% trehalose.

Raw material and biological starting material suitability, quality, and characterization (e.g., passage history of cell substrate and viral seed material) may include:

Recombinant VSVΔG-Env.BG505 is generated from a plasmid DNA containing a modified VSV genomic clone in which the G gene is replaced with sequence encoding HIV Env.BG505. Rescue of recombinant virus is initiated by electroporating the genomic clone with supporting plasmids that direct expression of VSV N, P, M, G, and L proteins and T7 phage RNA polymerase.

The VSV genomic clone is based on the VSV Indiana serotype.

The VeroCD4/CCR5 cell line used for preclinical development was generated starting with Vero cells from a cell bank qualified cell bank (obtained from Meridian Life Science, Inc). The VeroCD4/CCR5 cell line was generated by microporating cells with a plasmid that contains genes for expression of human CD4 and CCR5 and the Neo resistance marker.

VeroCD4/CCR5 is typically propagated in monolayer cultures. Cell factories are used for virus production. The cells are grown in DMEM supplemented with 10% fetal bovine serum from certified suppliers. Virus amplification can be conducted in monolayers in which the medium is exchanged with serum-free growth medium such as VPSFM.

Preclinical vaccine characterization may include:

Potency: Virus is quantified by plaque assay on VeroCD4/CCR5 cells. To confirm virus particles are pseudotyped with G, standard Vero monolayers are infected and the single-cycle infection in incubated overnight. Monolayers are subsequently immunostained to quantify infected cells.

Additional vaccine virus characterization:

Genome copies (qPCR) per infectious unit

Genomic nucleotide sequence

Env insert integrity by PCR

Env expression by Western blot

Env expression detected on infected cells by flow cytometry and bnAbs

Virus purity by denaturing gel electrophoresis and silver stain

*Mycoplasma* testing by PCR

Endotoxin testing

Assay development required to support lot release or product characterization may include:

Potency—see above, plaque assay and genome-to-pfu ratio

Safety:
  Env insert integrity by PCR
  Lack of VSV G gene by PCR
  Genomic sequence
  Infection of Vero cells with pseudotyped virus and subsequent blind passage to confirm lack of CPE indicating that virus is CD4/CCR5-dependent as expected Preparation of reagents to develop assays may include:

Primers and probes are available to assess genomic sequences, quantify genome copies, and specifically detect the Env gene insert.

Antibodies that can neutralize the pseudotyped VSVΔG-Env.BG505 chimera are required for adventitious agent testing. Antibodies recognizing the G pseudotype block infection in eggs, mice, and most cell lines provided they do not express primate CD4/CCR5.

REFERENCE CITATIONS

1. Lawson N D, Stillman E A, Whitt M A, Rose J K. Recombinant vesicular stomatitis viruses from DNA. Proceedings of the National Academy of Sciences of the United States of America. 1995; 92(10):4477-81. PubMed PMID: 7753828.
2. Clarke D K, Nasar F, Chong S, Johnson J E, Coleman J W, Lee M, Witko S E, Kotash C S, Abdullah R, Megati S, Luckay A, Nowak B, Lackner A, Price R E, Little P, Kalyan N, Randolf V, Javadian A, Zamb T J, Parks C L, Egan M A, Eldridge J, Hendry M, Udem S A. Neurovirulence and immunogenicity of attenuated recombinant vesicular stomatitis viruses in nonhuman primates. J Virol. 2014; 88(12):6690-701. doi: 10.1128/JVI.03441-13. PubMed PMID: 24696472; PubMed Central PMCID: PMC4054374.
3. Jones S M, Feldmann H, Stroher U, Geisbert J B, Fernando L, Grolla A, Klenk H D, Sullivan N J, Volchkov V E, Fritz E A, Daddario K M, Hensley L E, Jahrling P B, Geisbert T W. Live attenuated recombinant vaccine protects nonhuman primates against Ebola and Marburg viruses. Nature medicine. 2005; 11(7):786-90. PubMed PMID: 15937495.

4. Regules J A, Beigel J H, Paolino K M, Voell J, Castellano A R, Munoz P, Moon J E, Ruck R C, Bennett J W, Twomey P S, Gutierrez R L, Remich S A, Hack H R, Wisniewski M L, Josleyn M D, Kwilas S A, Van Deusen N, Mbaya O T, Zhou Y, Stanley D A, Bliss R L, Cebrik D, Smith K S, Shi M, Ledgerwood J E, Graham B S, Sullivan N J, Jagodzinski L L, Peel S A, Alimonti J B, Hooper J W, Silvera P M, Martin B K, Monath T P, Ramsey W J, Link C J, Lane H C, Michael N L, Davey R T, Jr., Thomas S J, r V-Z-GPSG. A Recombinant Vesicular Stomatitis Virus Ebola Vaccine—Preliminary Report. The New England journal of medicine. 2015. doi: 10.1056/NEJMoa1414216. PubMed PMID: 25830322.

5. Henao-Restrepo A M, Longini I M, Egger M, Dean N E, Edmunds W J, Camacho A, Carroll M W, Doumbia M, Draguez B, Duraffour S, Enwere G, Grais R, Gunther S, Hossmann S, Konde M K, Kone S, Kuisma E, Levine M M, Mandal S, Norheim G, Riveros X, Soumah A, Trelle S, Vicari A S, Watson C H, Keita S, Kieny M P, Rottingen J A. Efficacy and effectiveness of an rVSV-vectored vaccine expressing Ebola surface glycoprotein: interim results from the Guinea ring vaccination cluster-randomised trial. Lancet. 2015; 386(9996):857-66. doi: 10.1016/S0140-6736(15)61117-5. PubMed PMID: 26248676.

6. Agnandji S T, Huttner A, Zinser M E, Njuguna P, Dahlke C, Fernandes J F, Yerly S, Dayer J A, Kraehling V, Kasonta R, Adegnika A A, Altfeld M, Auderset F, Bache E B, Biedenkopf N, Borregaard S, Brosnahan J S, Burrow R, Combescure C, Desmeules J, Eickmann M, Fehling S K, Finckh A, Goncalves A R, Grobusch M P, Hooper J, Jambrecina A, Kabwende A L, Kaya G, Kimani D, Lell B, Lemaitre B, Lohse A W, Massinga-Loembe M, Matthey A, Mordmuller B, Nolting A, Ogwang C, Ramharter M, Schmidt-Chanasit J, Schmiedel S, Silvera P, Stahl F R, Staines H M, Strecker T, Stubbe H C, Tsofa B, Zaki S, Fast P, Moorthy V, Kaiser L, Krishna S, Becker S, Kieny M P, Bejon P, Kremsner P G, Addo M M, Siegrist C A. Phase 1 Trials of rVSV Ebola Vaccine in Africa and Europe—Preliminary Report. The New England journal of medicine. 2015. doi: 10.1056/NEJMoa1502924. PubMed PMID: 25830326.

7. Barr J N, Whelan S P, Wertz G W. Transcriptional control of the RNA-dependent RNA polymerase of vesicular stomatitis virus. Biochim Biophys Acta. 2002; 1577(2):337-53. PubMed PMID: 12213662.

8. Wertz G W, Perepelitsa V P, Ball L A. Gene rearrangement attenuates expression and lethality of a nonsegmented negative strand RNA virus. Proceedings of the National Academy of Sciences of the United States of America. 1998; 95(7):3501-6. PubMed PMID: 9520395.

9. Rabinovich S, Powell R L, Lindsay R W, Yuan M, Carpov A, Wilson A, Lopez M, Coleman J W, Wagner D, Sharma P, Kemelman M, Wright K J, Seabrook J P, Arendt H, Martinez J, DeStefano J, Chiuchiolo M J, Parks C L. A novel, live-attenuated vesicular stomatitis virus vector displaying conformationally intact, functional HIV-1 envelope trimers that elicits potent cellular and humoral responses in mice. PLoS ONE. 2014; 9(9):e106597. doi: 10.1371/journal.pone.0106597. PubMed PMID: 25215861; PubMed Central PMCID: PMC4162551.

10. Witko S E, Johnson J E, Kalyan N K, Felber B K, Pavlakis G N, Sidhu M K, Hendry R M, Udem S A, Parks C L. Refined methods for propagating vesicular stomatitis virus vectors that are defective for G protein expression. J Virol Methods. 2010; 164(1-2):43-50. Epub 2009/11/28. doi: 10.1016/j.jviromet.2009.11.023. PubMed PMID: 19941901; PubMed Central PMCID: PMC2837098.

11. Witko S E, Kotash C S, Nowak R M, Johnson J E, Boutilier L A, Melville K J, Heron S G, Clarke D K, Abramovitz A S, Hendry R M, Sidhu M S, Udem S A, Parks C L. An efficient helper-virus-free method for rescue of recombinant paramyxoviruses and rhadoviruses from a cell line suitable for vaccine development. J Virol Methods. 2006; 135(1):91-101. PubMed PMID: 16569439.

12. Cronin J, Zhang X Y, Reiser J. Altering the tropism of lentiviral vectors through pseudotyping. Current gene therapy. 2005; 5(4):387-98. PubMed PMID: 16101513.

13. Levy C, Verhoeyen E, Cosset F L. Surface engineering of lentiviral vectors for gene transfer into gene therapy target cells. Curr Opin Pharmacol. 2015; 24:79-85. doi: 10.1016/j.coph.2015.08.003. PubMed PMID: 26298515.

14. Kahn J S, Roberts A, Weibel C, Buonocore L, Rose J K. Replication-competent or attenuated, nonpropagating vesicular stomatitis viruses expressing respiratory syncytial virus (RSV) antigens protect mice against RSV challenge. J Virol. 2001; 75(22):11079-87. PubMed PMID: 11602747.

15. Kapadia S U, Simon I D, Rose J K. SARS vaccine based on a replication-defective recombinant vesicular stomatitis virus is more potent than one based on a replication-competent vector. Virology. 2008; 376(1):165-72. PubMed PMID: 18396306.

16. Fukazawa Y, Lum R, Okoye A A, Park H, Matsuda K, Bae J Y, Hagen S I, Shoemaker R, Deleage C, Lucero C, Morcock D, Swanson T, Legasse A W, Axthelm M K, Hesselgesser J, Geleziunas R, Hirsch V M, Edlefsen P T, Piatak M, Jr., Estes J D, Lifson J D, Picker L J. B cell follicle sanctuary permits persistent productive simian immunodeficiency virus infection in elite controllers. Nature medicine. 2015; 21(2):132-9. doi: 10.1038/nm.3781. PubMed PMID: 25599132; PubMed Central PMCID: PMC4320022.

17. Fukazawa Y, Park H, Cameron M J, Lefebvre F, Lum R, Coombes N, Mahyari E, Hagen S I, Bae J Y, Reyes M D, 3rd, Swanson T, Legasse A W, Sylwester A, Hansen S G, Smith A T, Stafova P, Shoemaker R, Li Y, Oswald K, Axthelm M K, McDermott A, Ferrari E, Montefiori D C, Edlefsen P T, Piatak M, Jr., Lifson J D, Sekaly R P, Picker L J. Lymph node T cell responses predict the efficacy of live attenuated SIV vaccines. Nature medicine. 2012; 18(11):1673-81. doi: 10.1038/nm.2934. PubMed PMID: 22961108; PubMed Central PMCID: PMC3493820.

18. Sanders R W, van Gils M J, Derking R, Sok D, Ketas T J, Burger J A, Ozorowski G, Cupo A, Simonich C, Goo L, Arendt H, Kim H J, Lee J H, Pugach P, Williams M, Debnath G, Moldt B, van Breemen M J, Isik G, Medina-Ramirez M, Back J W, Koff W C, Julien J P, Rakasz E G, Seaman M S, Guttman M, Lee K K, Klasse P J, LaBranche C, Schief W R, Wilson I A, Overbaugh J, Burton D R, Ward A B, Montefiori D C, Dean H, Moore J P. HIV-1 neutralizing antibodies induced by native-like envelope trimers. Science. 2015. doi: 10.1126/science.aac4223. PubMed PMID: 26089353.

19. Sharma S K, de Val N, Bale S, Guenaga J, Tran K, Feng Y, Dubrovskaya V, Ward A B, Wyatt R T. Cleavage-Independent HIV-1 Env Trimers Engineered as Soluble Native Spike Mimetics for Vaccine Design. Cell Rep. 2015; 11(4):539-50. doi: 10.1016/j.celrep.2015.03.047. PubMed PMID: 25892233.

20. Burton D R, Mascola J R. Antibody responses to envelope glycoproteins in HIV-1 infection. Nature immunology. 2015; 16(6):571-6. doi: 10.1038/ni.3158. PubMed PMID: 25988889.
21. Blattner C, Lee J H, Sliepen K, Derking R, Falkowska E, de la Pena A T, Cupo A, Julien J P, van Gils M, Lee P S, Peng W, Paulson J C, Poignard P, Burton D R, Moore J P, Sanders R W, Wilson I A, Ward A B. Structural Delineation of a Quaternary, Cleavage-Dependent Epitope at the gp41-gp120 Interface on Intact HIV-1 Env Trimers. Immunity. 2014. doi: 10.1016/j.immuni.2014.04.008. PubMed PMID: 24768348.
22. Falkowska E, Le K M, Ramos A, Doores K J, Lee J H, Blattner C, Ramirez A, Derking R, van Gils M J, Liang C H, McBride R, von Bredow B, Shivatare S S, Wu C Y, Chan-Hui P Y, Liu Y, Feizi T, Zwick M B, Koff W C, Seaman M S, Swiderek K, Moore J P, Evans D, Paulson J C, Wong C H, Ward A B, Wilson I A, Sanders R W, Poignard P, Burton D R. Broadly Neutralizing HIV Antibodies Define a Glycan-Dependent Epitope on the Prefusion Conformation of gp41 on Cleaved Envelope Trimers. Immunity. 2014. doi: 10.1016/j.immuni.2014.04.009. PubMed PMID: 24768347.
23. Boritz E, Gerlach J, Johnson J E, Rose J K. Replication-competent rhabdoviruses with human immunodeficiency virus type 1 coats and green fluorescent protein: entry by a pH-independent pathway. J Virol. 1999; 73(8):6937-45. Epub 1999/07/10. PubMed PMID: 10400792; PubMed Central PMCID: PMC112779.
24. Hoffenberg S, Powell R, Carpov A, Wagner D, Wilson A, Kosakovsky Pond S, Lindsay R, Arendt H, Destefano J, Phogat S, Poignard P, Fling S P, Simek M, Labranche C, Montefiori D, Wrin T, Phung P, Burton D, Koff W, King C R, Parks C L, Caulfield M J. Identification of an HIV-1 clade A envelope that exhibits broad antigenicity and neutralization sensitivity and elicits antibodies targeting three distinct epitopes. J Virol. 2013; 87(10):5372-83. doi: 10.1128/JVI.02827-12. PubMed PMID: 23468492; PubMed Central PMCID: PMC3648150.
25. Goo L, Chohan V, Nduati R, Overbaugh J. Early development of broadly neutralizing antibodies in HIV-1-infected infants. Nature medicine. 2014; 20(6):655-8. doi: 10.1038/nm.3565. PubMed PMID: 24859529; PubMed Central PMCID: PMC4060046.
26. Wu X, Parast A B, Richardson B A, Nduati R, John-Stewart G, Mbori-Ngacha D, Rainwater S M, Overbaugh J. Neutralization escape variants of human immunodeficiency virus type 1 are transmitted from mother to infant. J Virol. 2006; 80(2):835-44. doi: 10.1128/JVI.80.2.835-844.2006. PubMed PMID: 16378985; PubMed Central PMCID: PMC1346878.
27. Wyatt L S, Belyakov I M, Earl P L, Berzofsky J A, Moss B. Enhanced cell surface expression, immunogenicity and genetic stability resulting from a spontaneous truncation of HIV Env expressed by a recombinant MVA. Virology. 2008; 372(2):260-72. Epub 2007/12/01. doi: 10.1016/j.virol.2007.10.033. PubMed PMID: 18048074; PubMed Central PMCID: PMC2289778.
28. Johnson J E, Rodgers W, Rose J K. A plasma membrane localization signal in the HIV-1 envelope cytoplasmic domain prevents localization at sites of vesicular stomatitis virus budding and incorporation into VSV virions. Virology. 1998; 251(2):244-52. Epub 1998/12/05. doi: 10.1006/viro.1998.9429. PubMed PMID: 9837788.
29. Tani H, Morikawa S, Matsuura Y. Development and Applications of VSV Vectors Based on Cell Tropism. Front Microbiol. 2011; 2:272. doi: 10.3389/fmicb.2011.00272. PubMed PMID: 22279443; PubMed Central PMCID: PMCPMC3260743.
30. Powell R L, Ouellette I, Lindsay R W, Parks C L, King C R, McDermott A B, Morrow G. A Multiplex Microsphere-Based Immunoassay Increases the Sensitivity of SIV-Specific Antibody Detection in Serum Samples and Mucosal Specimens Collected from Rhesus Macaques Infected with SIVmac239. BioResearch open access. 2013; 2(3):171-8. doi: 10.1089/biores.2013.0009. PubMed PMID: 23741627; PubMed Central PMCID: PMC3666263.
31. Winstone N, Wilson A J, Morrow G, Boggiano C, Chiuchiolo M J, Lopez M, Kemelman M, Ginsberg A A, Mullen K, Coleman J W, Wu C D, Narpala S, Ouellette I, Dean H J, Lin F, Sardesai N Y, Cassamasa H, McBride D, Felber B K, Pavlakis G N, Schultz A, Hudgens M G, King C R, Zamb T J, Parks C L, McDermott A B. Enhanced control of pathogenic Simian immunodeficiency virus SIVmac239 replication in macaques immunized with an interleukin-12 plasmid and a DNA prime-viral vector boost vaccine regimen. J Virol. 2011; 85(18):9578-87. Epub 2011/07/08. doi: 10.1128/JVI.05060-11. PubMed PMID: 21734035; PubMed Central PMCID: PMC3165762.
32. Barouch D H, Alter G, Broge T, Linde C, Ackerman M E, Brown E P, Borducchi E N, Smith K M, Nkolola J P, Liu J, Shields J, Parenteau L, Whitney J B, Abbink P, Ng'ang'a D M, Seaman M S, Lavine C L, Perry J R, Li W, Colantonio A D, Lewis M G, Chen B, Wenschuh H, Reimer U, Piatak M, Lifson J D, Handley S A, Virgin H W, Koutsoukos M, Lorin C, Voss G, Weijtens M, Pau M G, Schuitemaker H. HIV-1 vaccines. Protective efficacy of adenovirus/protein vaccines against SIV challenges in rhesus monkeys. Science. 2015; 349(6245):320-4. doi: 10.1126/science.aab3886. PubMed PMID: 26138104.
33. Sarzotti-Kelsoe M, Bailer R T, Turk E, Lin C L, Bilska M, Greene K M, Gao H, Todd C A, Ozaki D A, Seaman M S, Mascola J R, Montefiori D C. Optimization and validation of the TZM-bl assay for standardized assessments of neutralizing antibodies against HIV-1. J Immunol Methods. 2014; 409:131-46. doi: 10.1016/j.jim.2013.11.022. PubMed PMID: 24291345; PubMed Central PMCID: PMCPMC4040342.

Example 2: Vaccination with a Live Vesicular Stomatitis Virus-HIV Env Chimera Prevents SHIV Infection Seven of 10 Indian rhesus macaques vaccinated with a novel replication-competent vesicular stomatitis virus vector designed with functional HIV Env substituting for the native VSV glycoprotein remained uninfected after repeated rectal challenge with a heterologous clade B SHIV.

HIV is a challenging vaccine target because its functional envelope glycoproteins (Envs) are highly glycosylated, sequence diverse, and assembled into a compact trimeric complex (the Env spike) that restricts epitope access. Moreover, vaccines based on non-native forms of Env are either ineffective or provide limited protection. Therefore, Applicants developed a novel spike delivery vaccine (VSVΔG-Env.BG505) from vesicular stomatitis virus (VSV) by replacing the VSV glycoprotein (G) with functional clade A HIV Env. Rhesus macaques vaccinated with live VSVΔG-Env.BG505 developed Env antibodies, and importantly, 7 of 10 remained uninfected after repeated rectal challenge with heterologous clade B SHIV SF162p3. In contrast, a second more typical VSV vector expressing both Env and G induced Env antibodies but failed to protect, showing that the VSVΔG-Env.BG505 vector design was associated with preclinical efficacy. Applicants' results indicate that the VSVΔG chimeric virus platform is an important developing vaccine technology for HIV Env glycoprotein delivery.

HIV is a challenging vaccine target because its functional envelope glycoproteins (Envs) are highly glycosylated, sequence diverse, and assembled into a compact trimeric complex (the Env spike) that restricts epitope access. Moreover, vaccines based on non-native forms of Env are either ineffective or provide limited protection. Therefore, Applicants developed a novel spike delivery vaccine (VSVΔG-Env.BG505) from vesicular stomatitis virus (VSV) by replacing the VSV glycoprotein (G) with functional clade A HIV Env. Rhesus macaques vaccinated with live VSVΔG-Env.BG505 developed Env antibodies, and importantly, 7 of 10 remained uninfected after repeated rectal challenge with heterologous clade B SHIV SF162p3. In contrast, a second more typical VSV vector expressing both Env and G induced Env antibodies but failed to protect, showing that the VSVΔG-Env.BG505 vector design was associated with preclinical efficacy. Applicants' results indicate that the VSVΔG chimeric virus platform is an important developing vaccine technology for HIV Env glycoprotein delivery.

Replication-Competent VSV-HIV Env Vaccine Vectors.

The VSVΔG-Env.BG505 chimera was developed by replacing the VSV G gene with sequence encoding functional Env.BG505 (FIGS. 25A-B with more detail in the Materials and Methods) In addition to expressing Env and replicating with the cell tropism of HIV, the VSVΔG-Env.BG505 chimera has several other features to highlight. First, its dependence on Env.BG505 for propagation ensures that some functionally-configured Env is expressed during viral replication that will expose the immune system to authentic Env spikes. Second, because the vector lacks the G gene, negative effects caused by G expression are avoided, such as the VSV glycoprotein dominating B cell responses or inducing potent anti-vector immunity. Finally, cells infected with VSVΔG-Env.BG505 produce progeny virus particles containing Env arrayed on their surface, which is expected to substantially enhance immunogen presentation to B lymphocytes (11).

To directly investigate whether the live VSVΔG-Env.BG505 chimera was advantageous for the reasons mentioned above, VSV-G6-Env.BG505 (FIG. 25C) was developed as a comparator for use in the macaque study described below. VSV-G6-Env.BG505 is a more typical VSV vector in which the Env.BG505 gene was added as an extra transcription while retaining G. The vector was generated by reintroducing the G gene at the terminus of the negative-sense RNA genome (FIGS. 25A and C; G in genome position 6), which maintained Env in the same genomic position relative to the promoter (FIG. 25A) as in VSVΔG-Env.BG505 and modestly downregulated G expression (16). VSV-G6-Env.BG505 propagates efficiently using G, which recognizes a ubiquitous cellular receptor that enables infection of a broad range of cell types (17); thus, including VSV-G6-Env.BG505 in the vaccine study allowed us to ask whether this G-dependent vector might deliver the Env spike more effectively, perhaps because constitutive G expression confers increased replicative capacity in vivo, a different cell and tissue tropism, or both.

Figures 25A, 25B, 25C, 25D, 25E:
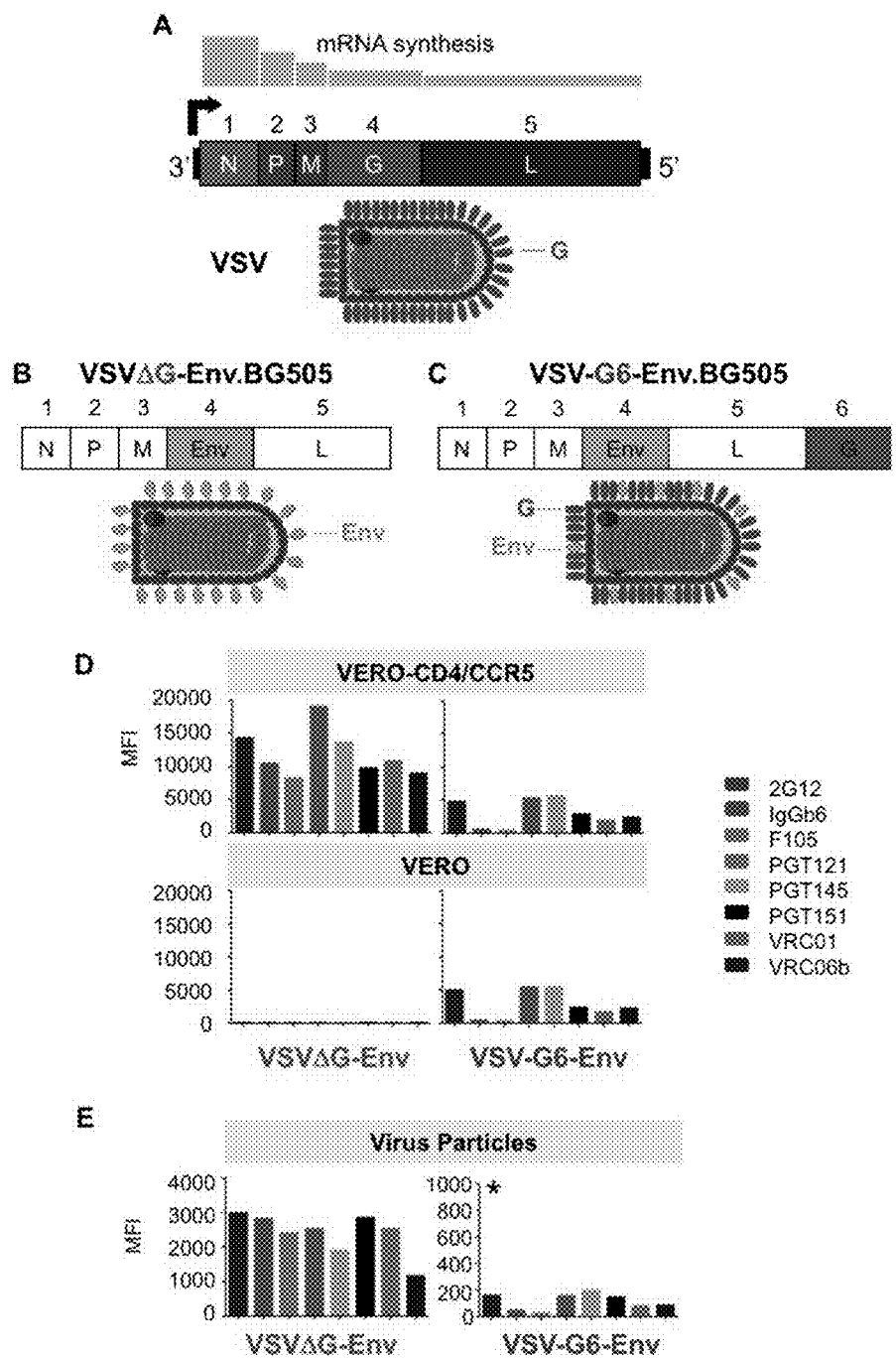
FIGS. 25A-25E. VSV-HIV vectors. (A) The VSV genome map is colored to correspond with proteins in the virus particle illustration. The 11-kb single-stranded, negative-sense, nonsegmented RNA genome encodes 5 proteins: (N) Nucleocapsid; Phosphoprotein (P); Large (L) RNA-dependent RNA polymerase subunit; (M) Matrix protein; (G) Glycoprotein. A single 3' promoter controls mRNA synthesis, with promoter-proximal genes being transcribed more frequently. The G gene was replaced with Env.BG505 sequence in VSVΔG-Env.BG505 (B) and VSV-G6-Env.BG505 (C), with G being reintroduced at the 5' terminus (position 6) of the VSV-G6-Env.BG505 genome. Env.BG505 encoded by both vectors was modified (FIG. 30A) to increase incorporation into the virus particle. (D) The surface of infected VERO or VERO-CD4/CCR5 cells was analyzed by flow cytometry using monoclonal antibodies specific for: high-manose glycans (2G12); a V3 epitope composed of polypeptide and glycan (PGT121); the CD4 binding site in native spikes (VRC01 and VRC06b) or in less compact Env species (F105 and IgGb6); and, native structures formed at the interface of spike subunits (PGT145 and PGT151). (E) Purified virus particles also were analyzed with the same antibodies using alum as a carrier for flow cytometry.

Env.BG505 expression by the two different VSV vectors was compared by infecting cultured cells and conducting flow cytometry using monoclonal antibodies that bind a variety of Env epitopes (4-6). When VERO cells or a stable VERO derivative (VERO-CD4/CCR5) expressing human CD4 and CCR5 were exposed to VSVΔG-Env.BG505, only the CD4+/CCR5+ cells were infected as shown by Env detected on the cell surface (FIG. 25D). The expanded tropism conferred by G allowed VSV-G6-Env.BG505 to infect both cell types although the intensity of Env surface staining was reduced compared to VERO-CD4/CCR5 cells infected with VSVΔG-Env.BG505. The more intense cell surface staining produced by VSVΔG-Env.BG505 infection was due at least in part to increased Env expression, which was detectable by Western blot analysis (data not shown), but it also was possible that G co-expression by cells infected with VSV-G6-Env.BG505 had a negative effect on Env incorporation into the cell plasma membrane. It also is important to note that the panel of monoclonal antibodies used for flow cytometry included some that recognize native Env spikes structures (PGT145, PGT151, and VRC06b) as well as others (IgGb6 and F105) that bind epitopes that are exposed when the Env subunits are not assembled into a compact spike (18-20). Infected cells were bound by all antibodies included in the panel demonstrating that multiple forms of Env were expressed on the cell surface including well-ordered Env spikes, as is typical for an HIV infection (21).

Because Env spikes arrayed on progeny virions produced during replication in vivo were expected to be important immunogens (11), the antigenicity of purified virus particles was analyzed with a modified flow cytometry assay. In this assay, virus particles are adsorbed to aluminum phosphate (alum) to generate alum-virus complexes that can be incubated with monoclonal antibodies and are large enough to be analyzed with a flow cytometer (16). Subsequent analysis with the same monoclonal antibody panel showed that substantially more Env was incorporated in the VSVΔG-Env.BG505 chimera compared to VSV-G6-Env.BG505 (FIG. 25E and note different Y axes), which also was confirmed by Western blotting (data not shown). The flow cytometry data also showed that the antigenicity of VSVΔG-Env.BG505 virions was similar to the infected cell surface (FIG. 25D), including binding by VRC06b, PGT145 and PGT151. In summary, analysis of purified virions showed that both VSVΔG-Env.BG505 and VSV-G6-Env.BG505 contained Env, but the immunogen was considerably more abundant in the VSVΔG chimeric virus particle.

Vaccination and Preclinical Efficacy.

Figures 26A, 26B:
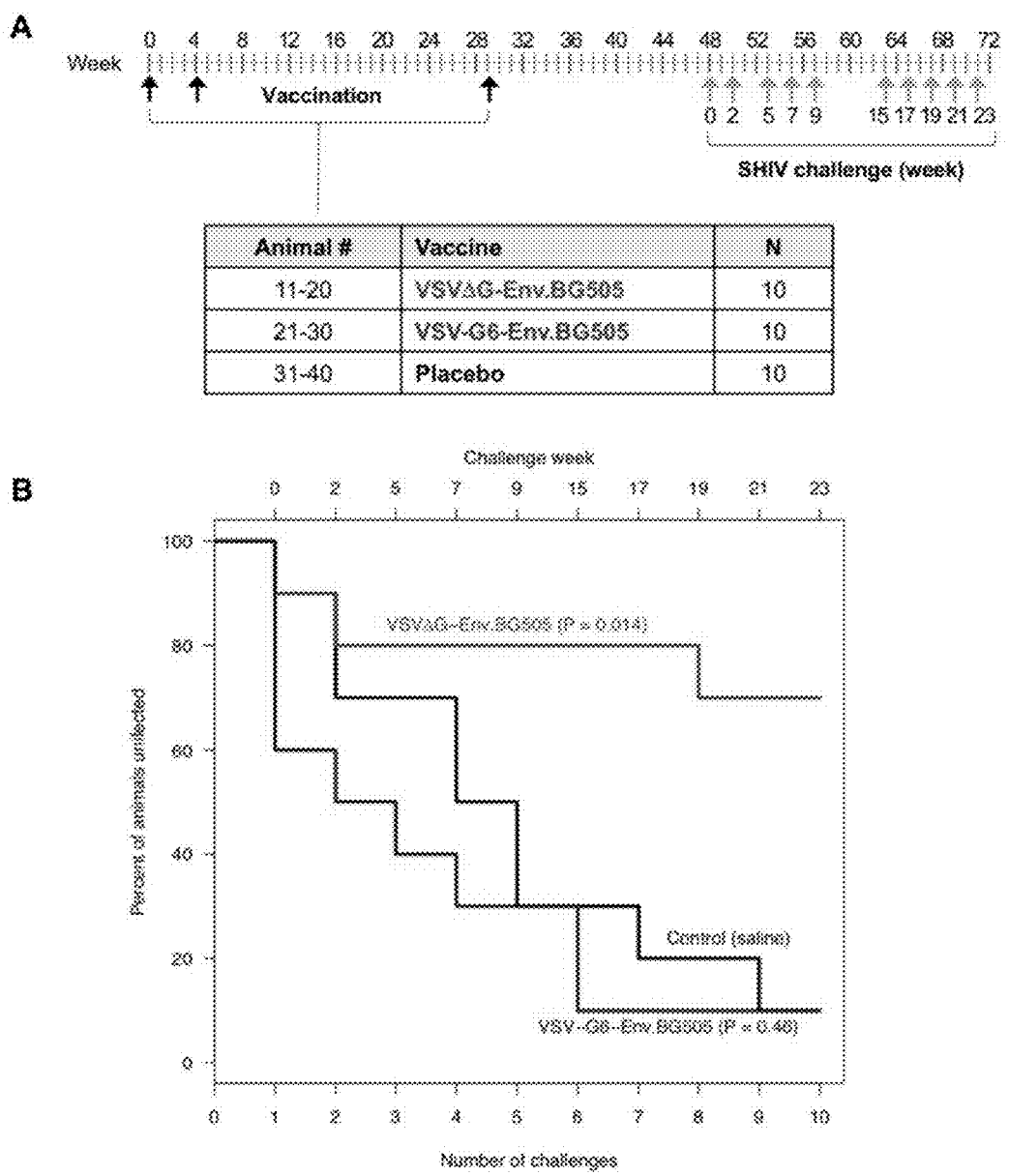
FIGS. 26A-B. Preclinical efficacy study. (A) Macaques were vaccinated three times by applying VSVΔG-EnvG505, VSV-G6-Env.BG505, or buffered solution to both intranasal ($1 \times 10^8$ pfus) and intraoral mucosal surfaces ($1 \times 10^8$ pfus). Intrarectal challenge with SHIV began 5 months after the final vaccination (study week 48). The SHIV SF162p3 challenge stock was prepared in macaque PBMCs and has been used in prior studies. Consensus nucleotide sequencing conducted with the challenge virus verified that the Env gene matched Genbank Accession KF042063. Macaques with SHIV genome copies ≥200 per ml on two successive blood draws were considered positive (FIG. 33) and further challenge was ended. (B) Kaplan-Meier survival curves by treatment assignment. P-values are from an exact log-rank test comparing each active treatment group to the control group.

Three groups of 10 male Indian rhesus macaques were vaccinated by administering live vector or saline control to both intranasal and intraoral surfaces at 0, 4 and 29 weeks (FIG. 26A). The five-month break between the second and third vaccination was included to provide time for germinal center reactions and B cell differentiation (22). All immunizations were conducted with a VSV vector, and no booster vaccinations were administered with a heterologous vector or subunit vaccine.

Figure 32:
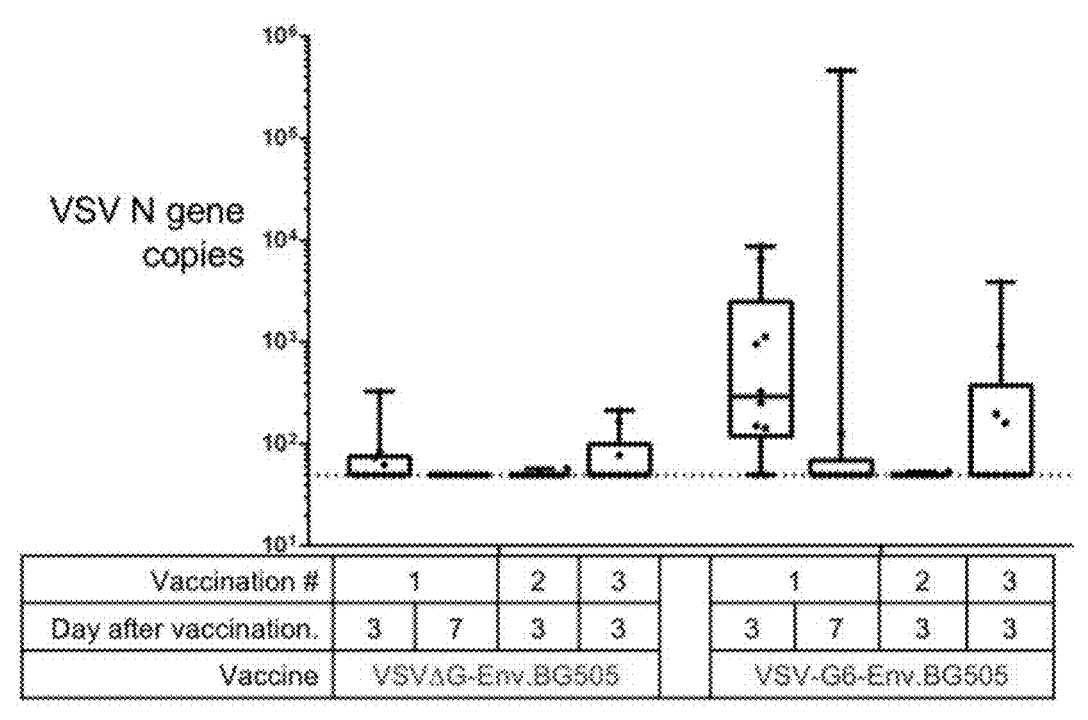

No adverse reactions were observed after vaccination. Virus shedding into the oral cavity was analyzed using qRT-PCR, which showed that viral genomes were low to undetectable for VSVΔG-Env.BG505 but increased for VSV-G6-Env.BG505 particularly following the first vaccination (FIG. 32). This result implied that the replicative capacity of VSV-G6-Env.BG505 was greater, but it might also be due to differences in cell and tissue tropism affecting shedding into the oral cavity. VSV genomes were not detected in the blood (data not shown) in either group, which was consistent with lack of viremia detected in earlier studies (23). Interestingly, VSVΔG-ZEBOV did cause transient viremia in macaques (13) and clinical trial participants (14, 15), which might reflect an effect of cell tropism conferred by the Ebola virus glycoprotein.

Figure 33:
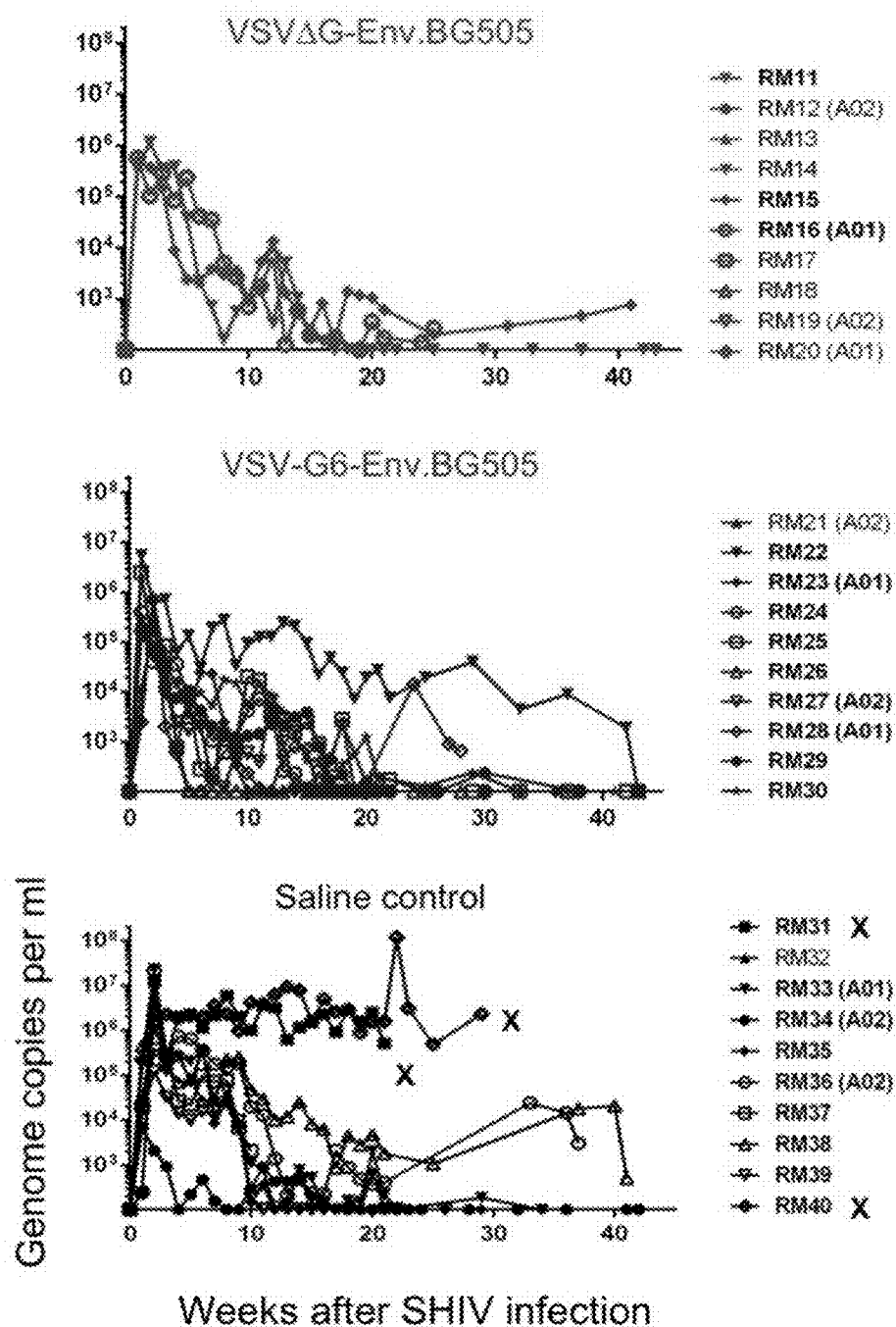
FIG. 33) and uninfected animal 32. Animal 31 was euthanized prior to this time point.
Figures 34A, 34B, 34C:
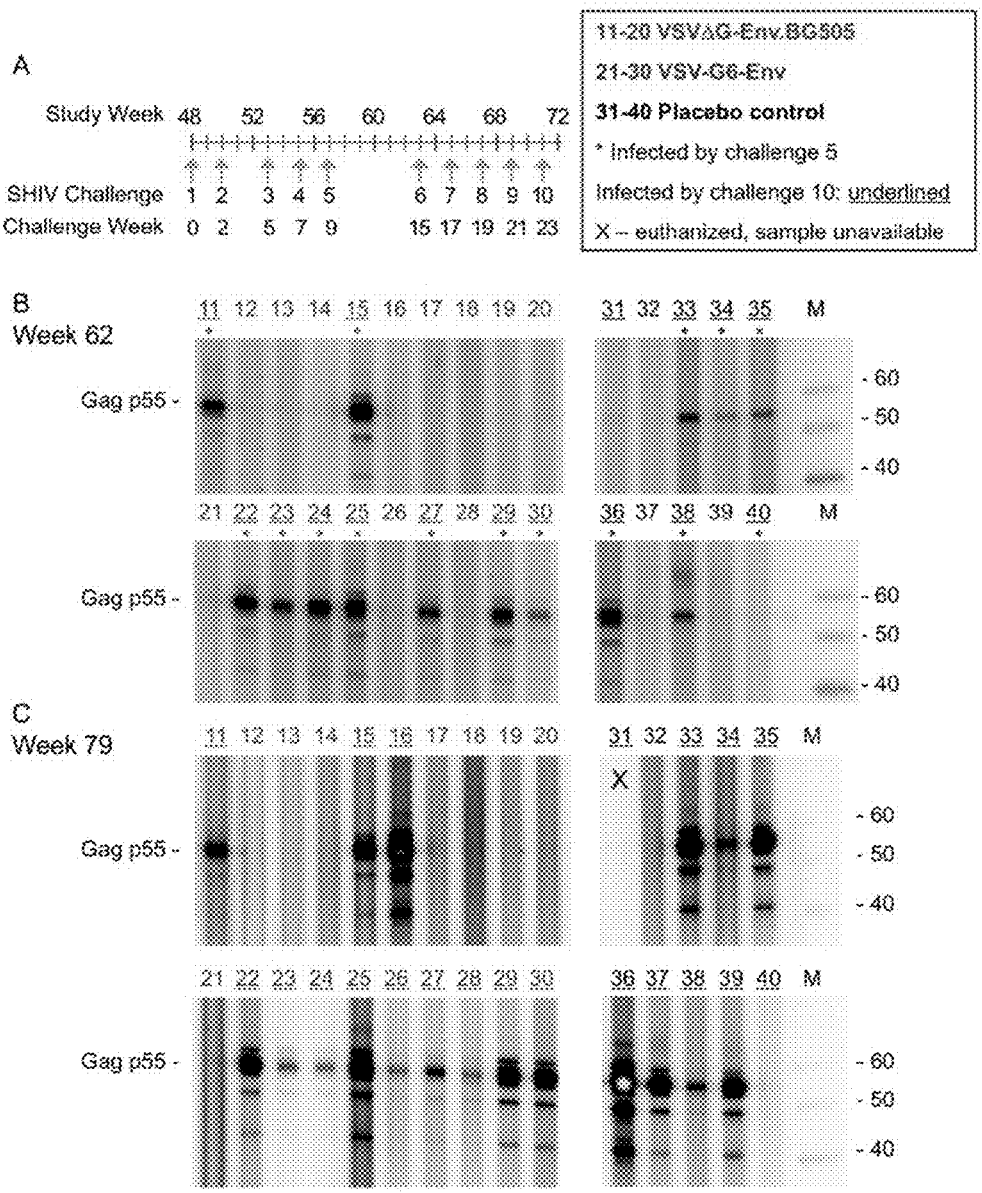
Figures 35A, 35B:
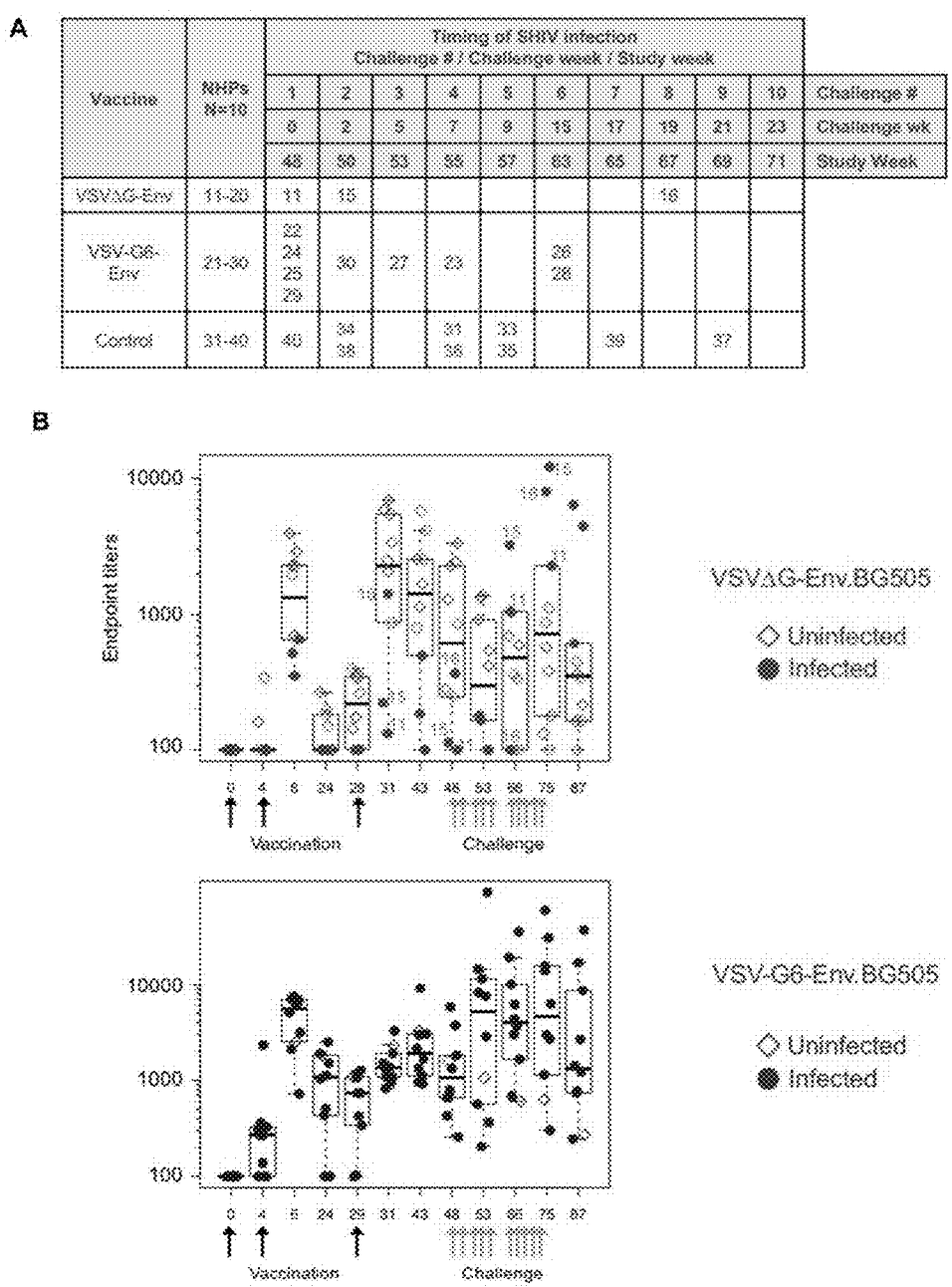

Intrarectal SHIV SF162p3 challenge commenced at week 48, about 4.5 months after the third vaccination (FIG. 26A). This rest period prior to SHIV challenge allowed waning of peak adaptive immune responses as well as decay of innate immunity that might have been triggered by VSV. A maximum of 10 sequential challenges were planned (FIG. 26A), with the first five being conducted approximately every 2 weeks after which a brief rest period was included to allow innate immune responses to decline if any were induced by repeated SHIV exposure (24, 25). Challenged animals that had 200 SHIV genome copies or more on two successive blood draws were considered positive (FIG. 33), at which time challenge was stopped. All vaccinated animals that tested positive for SHIV genomes also developed antibodies against Gag expressed by the SHIV (FIG. 34).

After completing repetitive SHIV challenge, 9 of 10 placebo control animals were infected but just 3 of 10 in the VSVΔG-Env.BG505 group (FIG. 26B). This indicated that the VSVΔG-Env.BG505 group was significantly protected with an overall efficacy of 67% (P=0.014). The per-challenge vaccine efficacy for VSVΔG-Env.BG505 was estimated to be 79.8% based on a Leaky vaccine model (26). In contrast, vaccination with VSV-G6-Env.BG505 had no protective effect (FIG. 26B, and Table 1).

Immune Responses Induced by Vaccination.

Figure 27:
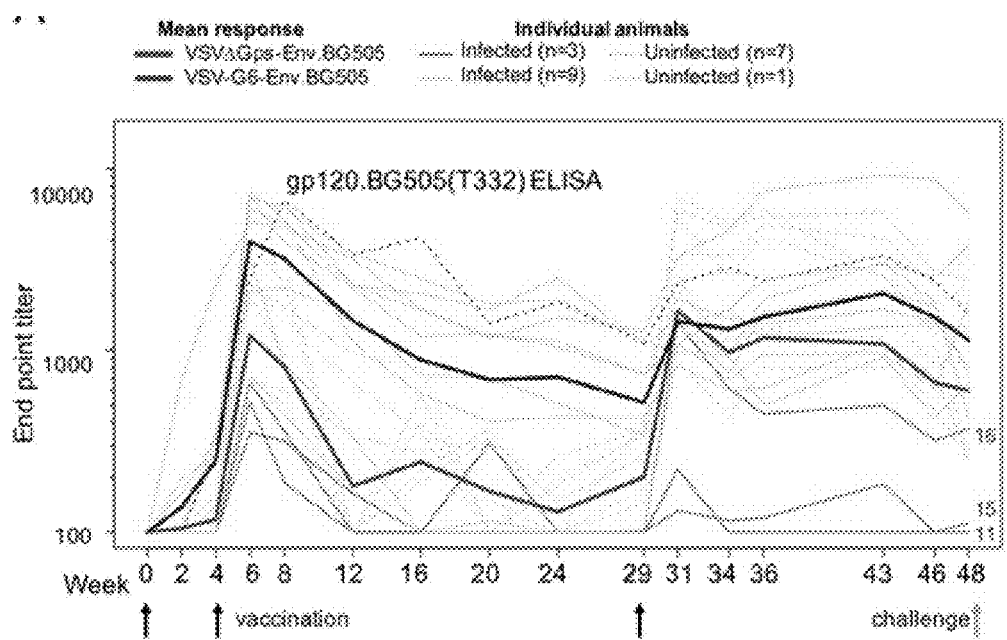
FIG. 27. Env serum antibody analysis. Longitudinal gp120 ELISA endpoint titers showing uninfected (dashed lines) or infected (solid lines) macaques and geometric mean values for the vaccine groups (bold solid lines). Unprotected animals 11, 15 and 16 from the VSVΔG-Env.BG505 group are identified in A and B to highlight their low titers.

Vaccinated macaques in both groups developed serum antibodies detectable with an Env gp120.BG505 ELISA (FIG. 27A). The longitudinal antibody titer profiles (FIG. 27A) showed that the first dose induced low antibody responses in both vaccine groups, which were not statistically different two weeks after immunization (box plots in FIG. 27B, Single Time Points). Titers increased after the second vaccination (FIG. 27A) and were statistically higher in the VSV-G6-Env.BG505 group 2 weeks later (FIG. 27B). Also in the VSV-G6-Env.BG505 group, the antibody titers were more durable after the second vaccination (FIG. 27A), and this difference was significant as shown by the average values of the aggregate titers during the six-month period prior to the third vaccination (FIG. 27B, Aggregate Values). The effect of the third vaccination differed between the groups. VSVΔG-Env.BG505 evoked a stronger response than VSV-G6-Env.BG505 (FIG. 27A) with the net result being that both groups had statistically equivalent mean titers two weeks following the third dose (FIG. 27B). Titer durability also was similar in both groups after the third vaccination up to the beginning of SHIV challenge at week 48, as shown in the longitudinal profile (FIG. 27A) and the average of the aggregate values during this time period (FIG. 27B). Overall, the ELISA data demonstrated that both mucosal vaccines were immunogenic without requiring a boost with a heterologous vaccine, and that the live viruses induced serum antibodies that persisted in most animals following the third vaccination.

Figure 36:
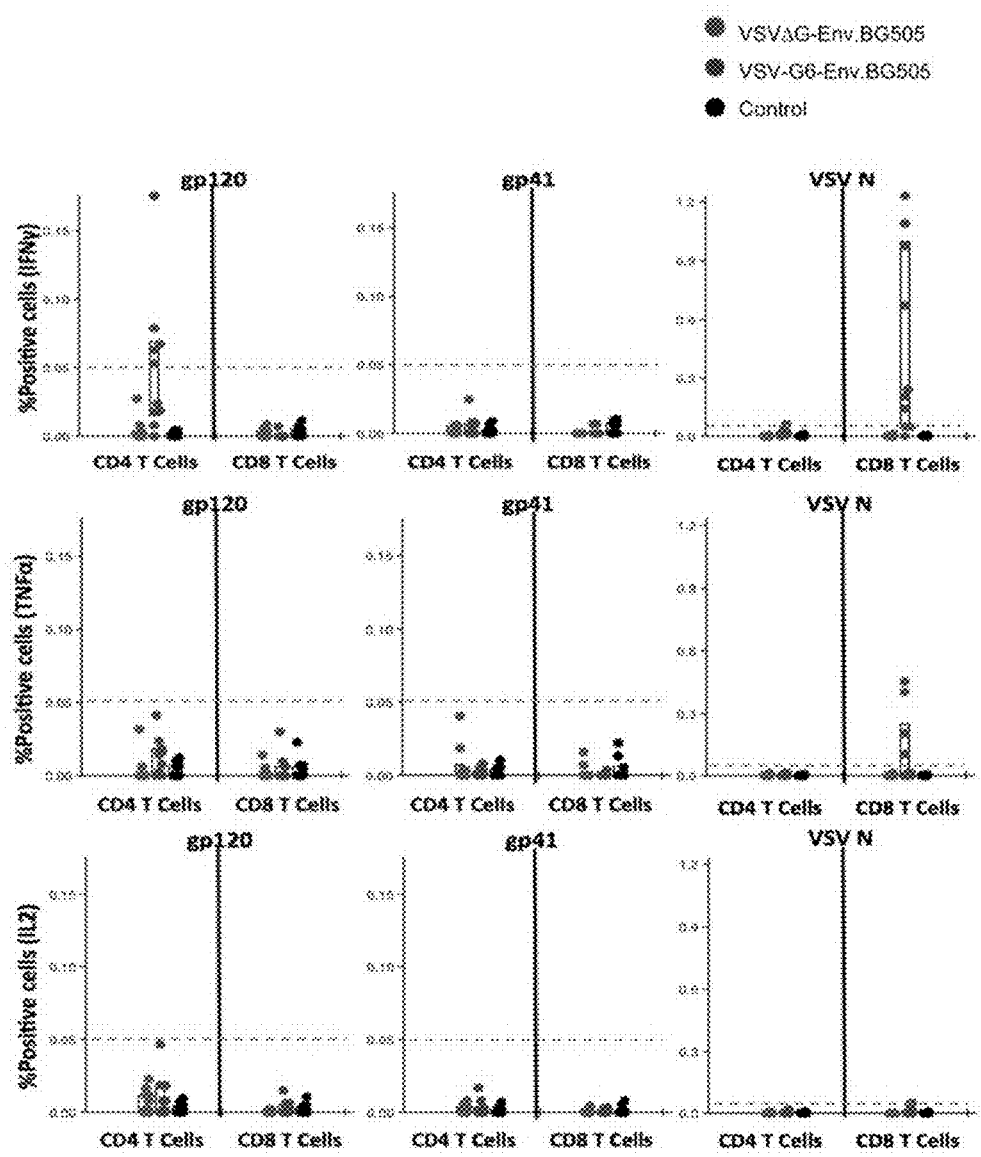

A prominent feature of the ELISA data was the low values corresponding to the three animals in the VSVΔG-Env.BG505 group (11, 15, and 16) that were unable to resist SHIV infection (FIG. 27A, fine solid red lines; FIG. 27B, solid red circles). Antibody titers in animals 11 and 15 were at the lower measurable limit when SHIV challenge was initiated at week 48 (FIGS. 26A and B), and both macaques were infected right away at challenge 1 and 2, respectively (FIG. 26B with more detail in FIG. 36). Animal 16 had somewhat higher ELISA values after the third vaccination (FIGS. 27A and B) that persisted up to initiation of SHIV challenge, suggesting that this enabled the macaque to resist 7 challenges conducted over a period of ~5 months (FIGS. 26B and 36). By challenge 8 (week 67) when infection occurred in animal 16, titers had declined to near baseline (FIG. 36B). Thus, in the three unprotected macaques in the VSVΔG-Env.BG505 group, low binding antibody titers were associated with the timing of SHIV infection.

Since neutralizing antibodies did not appear to be responsible for protection, other characteristics of the immune response were assessed. For example, Env-specific T-cells in peripheral blood were found to be below measurable limits in the VSVΔG-Env.BG505 group when analyzed by intracellular cytokine staining two weeks after the third vaccination (FIG. S7). This indicated that cellular immunity did not play a prominent role in protection although it did not rule out the possibility that T lymphocytes resident in tissues might be important (28). This lack of a substantial T cell response evoked by live VSVΔG-Env.BG505 was similar to what was observed in macaques vaccinated with VSVΔG-ZEBOV previously (13). Sera from just 3 of the 7 protected macaques vaccinated with VSVΔG-Env.BG505 had detectable anti-V1V2 IgG, while it was more frequently detected in the VSV-G6-Env.BG505 group that was not protected (FIG. S8) indicating that antibodies with this specificity were not correlated with SHIV resistance.

Figures 28A, 28B, 28C, 28D:
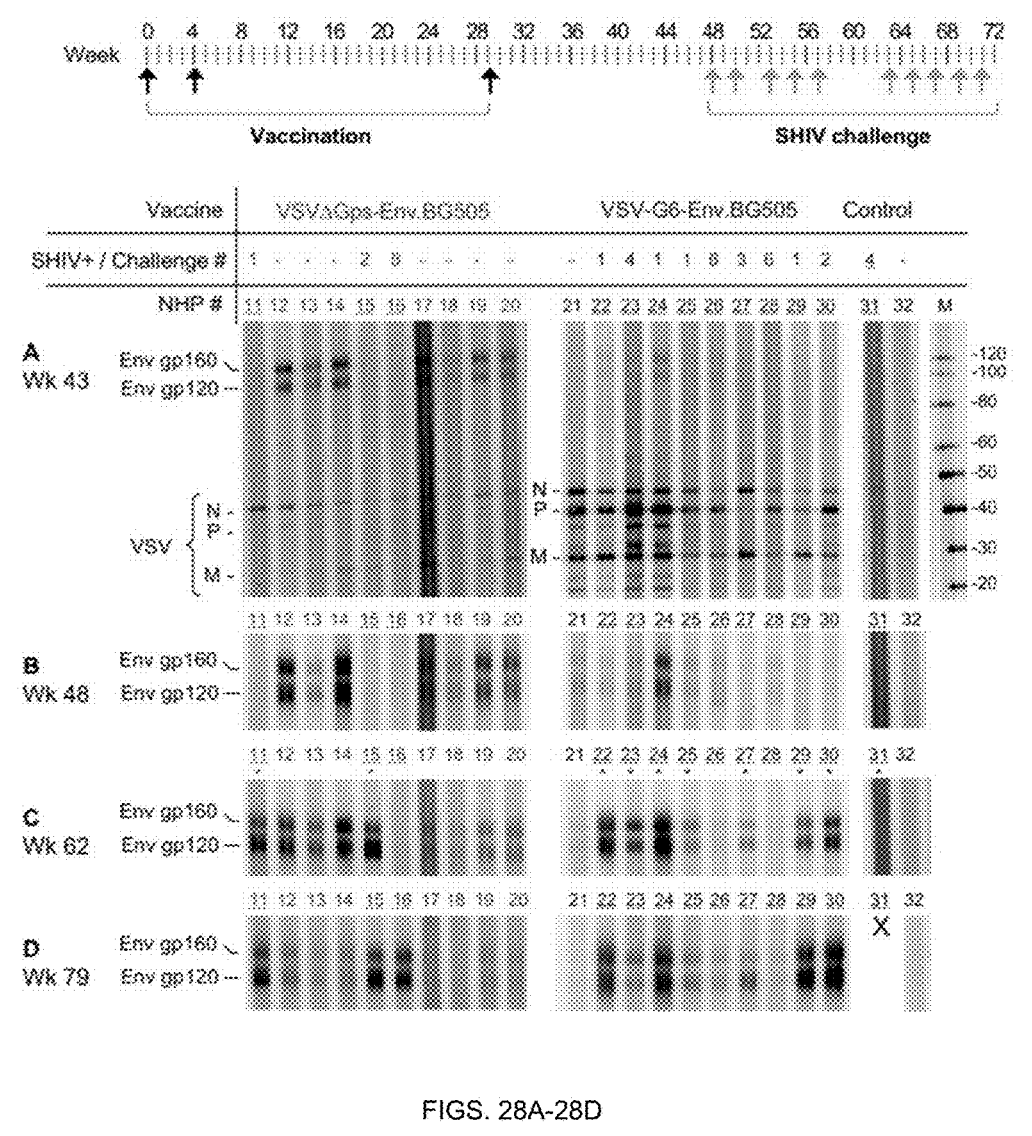

Because neither neutralizing antibodies or IgG specific for gp70-V1V2 correlated with protection, serum antibodies were characterized further with a Western blot assay that could detect binding to Env as well as VSV structural proteins. This was done to investigate whether B cell responses against any of the polypeptides expressed by the replicating vectors might help differentiate between the two vaccine groups. Western blot membranes were prepared using proteins derived from purified VSVΔG-EnvG.BG505 particles, which provided multiple forms of the Env.BG505 (gp160 precursor, gp120, and gp41) as well as the internal VSV structural proteins (N, P, and M; FIG. 25A). Blot membranes were placed in a multichannel device to create lanes that allowed analysis of sera from individual macaques, and when samples were analyzed from after the third vaccination (week 43), two distinctive differences in antibody reactivity were detected between the groups (FIG. 28A). In animals vaccinated with VSVΔG-Env.BG505, the Env signals were more prominent (animals 12-14, 17-20) while signals corresponding to VSV polypeptides were weak. In contrast, sera from animals vaccinated with VSV-G6-Env.BG505 reacted more strongly with VSV structural proteins (N, P, and M), and relatively weakly with gp120 and gp160. The difference in Env signal between the groups was somewhat unexpected, as the group mean gp120 ELISA titers were similar following the third vaccination (FIGS. 27A and B) suggesting that the ELISA and Western blot might be probing different Env antibody qualities. The Western blot results also showed clearly that the polyclonal antibody response induced by the two vaccines was different.

Figures 37A, 37B, 37C:
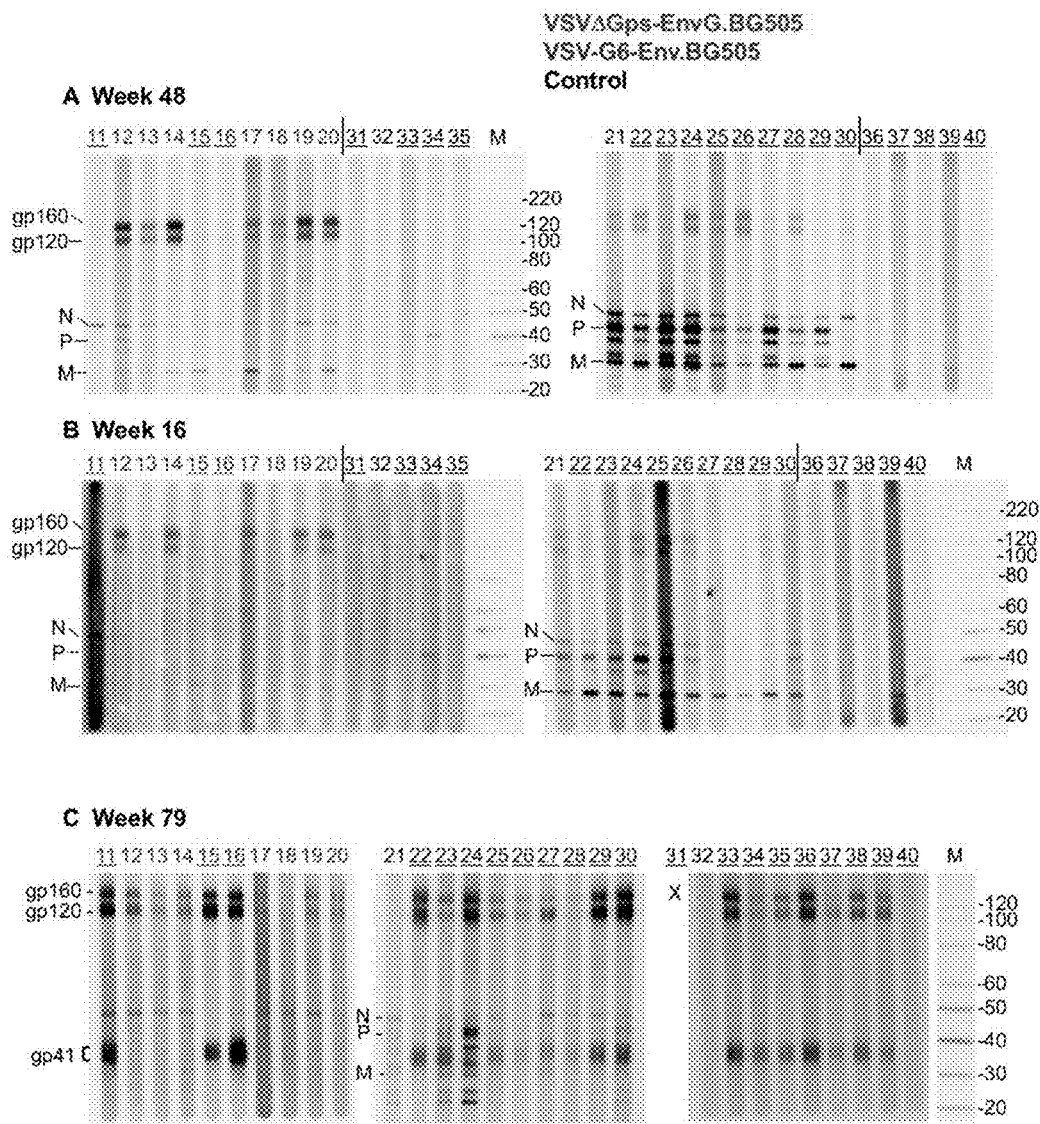
FIGS. 37A-37C. Additional characterization of serum antibodies by Western blot. Assays were performed as in FIG. 28. (A) An independent week-48 Western blot, like the one in FIG. 28B, is shown with all control animals included. The full-length blot also shows reactivity with VSV polypeptides as described in FIG. 28A. Sera from control animals lacked significant VSV and Env signals as expected, except for occasional detection of bands that migrated at positions consistent with VSV M and P. (B) A Western blot performed with sera collected at study week 16, which was 12 weeks after the second vaccination. The result showed that the Env signal was detectable at this earlier time even though the ELISA titers were considerably lower in the VSVΔG-Env.BG505 group after the second vaccination (FIG. 27A). (C) An independent week-79 Western blot similar to the one in FIG. 28D. The full length blot shows that serum from infected macaques was able to detect gp41. Most control macaques also developed antibodies that bound gp41 except for two animals that had had progressive infections (macaques 31 and 40.

The Western blot also differentiated between macaques in the VSVΔG-Env.BG505 group (FIG. 28A) that did or did not resist SHIV infection. Sera from the 7 macaques that were protected produced Env signals of varying intensities (macaques 12-14 and 17-20), while sera from the three animals that were not protected (11, 15, and 16) produced very weak to undetectable signals. At week 43, the ELISA titers in animals 11 and 15 were low (FIG. 27A), consistent with the lack of Western blot signal. ELISA titers were higher in animal 16 at this time, suggesting that titer as well as characteristics of the polyclonal antibodies might contribute to lack of reactivity in the Western blot. Similar Western blot binding profiles also were produced by sera from other time points during the vaccination regimen. For example, the pattern of Env (FIG. 28B) and VSV polypeptide reactivity (FIG. 37A) was reproduced with week-48 sera and also with sera from after the second vaccination (FIG. 37B, week 16) even though the antibody titers were considerably lower in the VSVΔG-Env.BG505 group at this earlier time point (FIG. 27A).

To determine if the Western blot Env signal persisted in serum from protected macaques, sera was analyzed from the SHIV challenge phase. At study week 62, after 5 SHIV challenges, the Env bands remained detectable in the uninfected macaques in the VSVΔG-Env.BG505 group (FIG. 28C, animals 12-14, 17-20). It also was evident that the Env signals increased substantially in macaques that were infected by week 62, such as animals 11 and 15. Later, at week 79 when 10 challenges were complete, and about one year after the last vaccination, sera from 5 of 7 uninfected macaques still produced an Env band that was readily visualized (FIG. 28D, animals 12-14, 19 and 20) and two produced weaker but detectable bands (17 and 18). These results showed that VSVΔG-Env.BG505 elicited Env binding antibodies that persisted in the uninfected animals.

Because Western blotting (FIG. 28) and gp120 ELISA data (FIG. 27) indicated that Env binding antibodies played a role in preventing infection with a heterologous clade B SHIV challenge virus, it was important to confirm that vaccination induced antiserum with substantial cross-clade binding activity. A binding antibody multiplex assay (BAMA, 30) was used to assess binding against two Env panels (gp120 or gp140) composed of substrates from clade A, B, and C as well as several circulating recombinant viruses. Assays also were performed with four Env gp120 substrates used in clinical trials as well as Env gp120 and gp140 from clade B SF162.LS, which is an Env from a progenitor of the SHIV SF162p3 challenge virus.

Figures 29A, 29B:
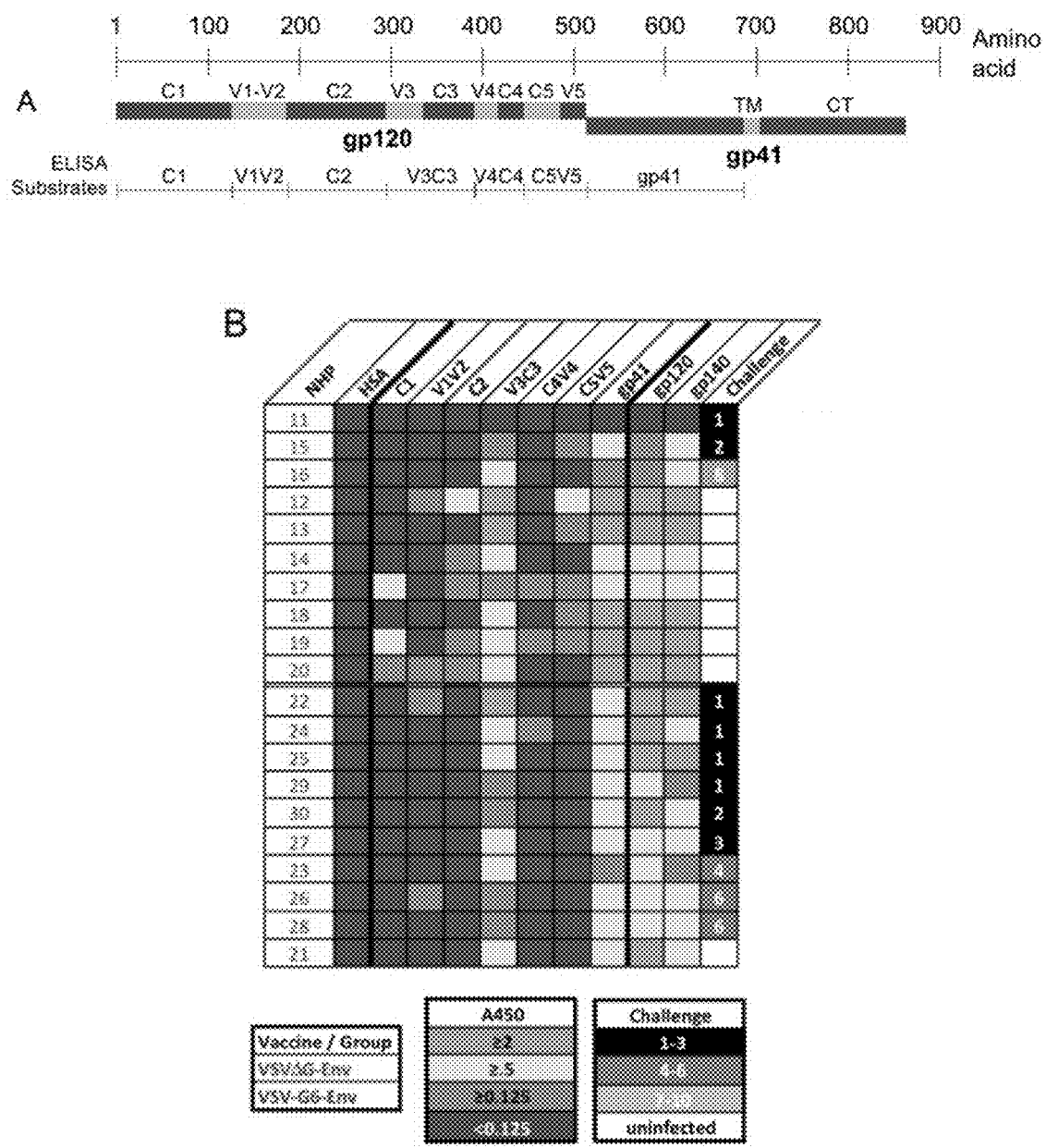
FIGS. 29A-29B. Mapping Env antibody binding regions. (A) Linear map of Env Constant (C1-C5) and Variable (V1-V5) domains. The map breaks at furin cleavage site between gp120 and gp41. The transmembrane (TM) region and cytoplasmic tail (CT) are labeled in gp41. Below the map, boundaries are shown for the Env fragments fused to human serum albumin (HSA) to generate ELISA substrates. (B) Analysis of sera using capture ELISA and the HSA fusion proteins shown in (A). HSA without a fused Env sequence was included as a negative control. Env gp120 and gp140 ELISA substrates were not fused to HSA. The data from an example experiment (absorbance at 450 nm; A450) is presented as a heat map with the scale shown at the bottom adjacent to a scale showing the SHIV challenge when infection occurred.
Figure 39:
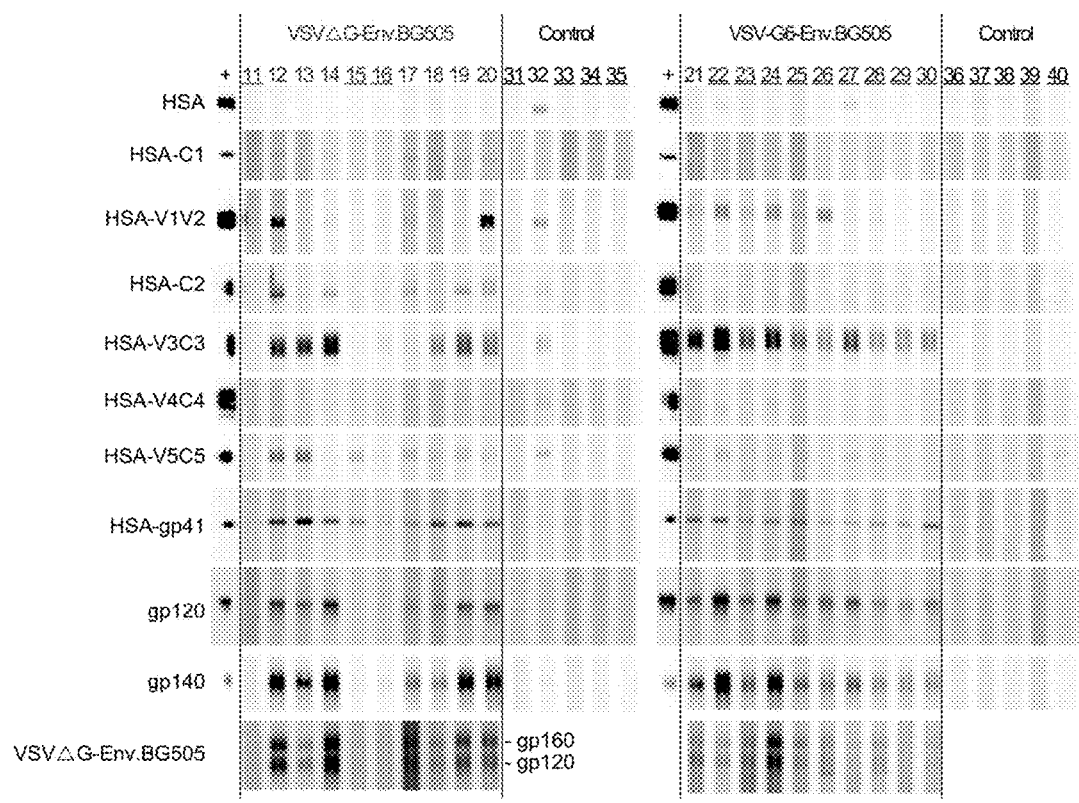
FIG. 39. Analysis of serum antibody binding to different Env regions by Western blotting. Sera from week 48 was analyzed as described in FIG. 28 except that recombinant gp120, gp140, and HSA fusion proteins (FIG. 29A) were used as substrates. The positive control lane (+) included anti-HIS antibody.

Finally, to determine what regions of Env might be targeted in response to VSVΔG-Env.BG505 vaccination, additional mapping of serum antibody binding specificity was performed with several assays. For conducting ELISAs and Western blots, seven different regions of Env.BG505 (FIG. 29A) were expressed as fusion proteins using human serum albumin (HSA) as the N-terminal fusion partner. Fusion to HSA enabled expression of the Env.BG505 fragments as secreted glycoproteins (31). For the ELISA results shown in FIG. 29B, the purified recombinant proteins were captured on microtiter plates (capture ELISA) using their C-terminal His tag after which they were reacted with sera from week 48. Four conclusions can be drawn from the capture ELISA data. First, the predominant positive signal in both vaccine groups was against the HSA-V3C3 and HSA-gp41 (gp41 ectodomain only). These fusion proteins also generated the most frequent and intense signals when used in a Western blot assay (FIG. 39). Second, sera from the three unprotected macaques in the VSVΔG-Env.BG505 group (11, 15, and 16) had lower HSA-V3C3 and HSA-gp41 values consistent with these animals being low responders, as observed earlier with gp120 ELISA (FIGS. 27A-B) and Western blots (FIGS. 28A-B). Finally, the HSA-gp41 substrate allowed unambiguous detection of antibodies specific for gp41 in vaccinated animals (FIGS. 29B and 39), which were not observed in the earlier Western blot assays (FIGS. 28A and 37). Lack of gp41 signals in the prior Western blots likely was due to lower gp41 quantities being present on the blot membrane, but perhaps conformation assumed by the different gp41 substrates played some role. It was also noticeable that the capture ELISA gp41 values were generally higher in protected animals from the VSVΔG-Env.BG505 group.

Seven of 10 macaques vaccinated with the live Env-dependent VSVΔG-Env.BG505 chimera remained uninfected after repeated rectal challenge with heterologous clade B SHIV SF162p3 (FIG. 26). Notably, this level of efficacy was produced with a three-dose regimen of VSVΔG-Env.BG505, which differentiates this vaccine from some others evaluated before where protection was observed after immunization with multiple types of vaccine used either in combination or in a heterologous prime-boost regimen (8, 33, 34).

In the 7 protected macaques vaccinated with VSVΔG-Env.BG505, resistance to SHIV infection was associated with persistent Env-specific serum antibodies, while in the three animals that became infected, poor vaccine take or waning antibody titers were a marker of susceptibility (FIGS. 27-29 and 36). Perhaps the most visual evidence for this was the gp120 ELISA data (FIGS. 27A and B, and 36) and Western blot results (FIG. 28), which clearly showed that the unprotected animals had reduced quantities of Env-specific serum antibodies. Further analysis of the sera from this group identified statistically significant correlations between the magnitude of antibody binding activity and SHIV infection resistance (6D), but it remains to be determined if the more abundant Env antibodies are directly involved in the protective mechanism or whether they primarily are indicators of VSVΔG-Env.BG505 vaccine take. The suggestion that they contribute to the mechanism of protection might gain support from the data showing that gp120 V3 and gp41 (FIG. 29) were prominent targets of the antibody response induced by VSVΔG-Env.BG505. Antibody binding to V3 and gp41 has been linked to protection before, for example, reduced infection risk was correlated with anti-V3 antibodies in the RV144 clinical trial (32) and anti-gp41 antibodies have been associated with protection from progressive SIV infection in the macaque model (35).

Functional activities associated with the protective antibodies remain to be identified. Virus neutralizing activity was not detected in serum (FIG. 27D), although it might have been unmeasurable because the live vectors induced modest antibody titers (FIG. 27A). Even if undetectable quantities of neutralizing serum antibodies were present, their activity likely would not be adequate to mediate protection (36). Maybe mucosal vaccination with VSVΔG-Env.BG505 resulted in neutralizing antibody being tissue associated or in mucosal secretions rather than in circulation, although anti-gp120 antibodies were not detected in oral or rectal swab samples (data not shown). It seems more likely that protection was due to Env-specific immunoglobulins that direct antibody-mediated effector functions, like those induced by other Env vaccine candidates evaluated in recent preclinical studies (33, 34) or the RV144 clinical trial (8). There is growing recognition that antibodies lacking classic in vitro virus neutralizing activity contribute substantially to protection from viral infections, as illustrated by some recent studies on influenza virus (37, 38); thus, further investigation and comparison of effector functions associated with IgG induced by protective VSVΔG-Env.BG505 or nonprotective VSV-G6-Env.BG505 will be informative.

Although the serum antibody titers evoked by mucosal vaccination with VSVΔG-Env.BG505 were modest (FIG. 27A), the Western blot results indicated that binding activity persisted for at least a year in protected animals (FIG. 28D). This might resemble what is observed during vaccination with live attenuated viruses like in the measles vaccine.

Antibody titers established by measles vaccination are considerably lower than those reached during natural infection, but the attenuated virus replicates sufficiently to establish durable protective antibodies (39). There likely is a similar requirement for VSVΔG-Env.BG505 to achieve replication threshold that provides an adequate quantity and duration of Env expression, results in release of immunogenic virus particles containing Env arrayed on their surface (11), and distributes immunogen to lymphoid tissues (40). Possibly, vaccine failure in the three unprotected macaques in the VSVΔG-Env.BG505 group was caused by inadequate replication, thus future studies that investigate VSVΔG-Env.BG505 propagation in vivo will be important.

Replicative capacity might also contribute to a notable difference between the VSVΔG-ZEBOV and VSVΔG-Env.BG505 chimeric virus vaccines. In preclinical and clinical studies (13-15), a single vaccination with VSVΔG-ZEBOV was sufficient for efficacy. Applicants' data suggested that multiple VSVΔG-Env.BG505 vaccinations probably were necessary to establish a more persistent Env antibody titer, with the third vaccination having a substantial effect on durability (FIG. 27A). A single vaccination with VSVΔG-ZEBOV may be sufficient because the virus apparently replicates and disseminates more extensively based on finding virus in the blood of macaques and clinical trial volunteers (13-15). This suggests that further development of the VSVΔG-Env.BG505 vaccine may benefit from investigating how to safely increase virus replication. This might be achieved by launching a more robust initial infection using a different vaccination route or higher dose, or alternatively, maybe a VSVΔG-Env.BG505 vector can be developed that has increased replicative capacity. A follow up study in macaques is being initiated to investigate some of these variables.

The VSVΔG chimeric virus design appears to be emerging as an important vaccine technology for delivery of viral glycoprotein immunogens. The VSVΔG-ZEBOV clinical trials showed that the Ebola virus vaccine was safe and efficacious (13-15). Promising preclinical results also have been produced with other hemorrhagic fever virus glycoproteins (41), and now Applicants' data shows that this strategy can be adapted for use with an HIV Env trimer immunogen, which is well known to be a very difficult vaccine target (5). The effectiveness of the VSVΔG chimera design probably is due to its ability to reproduce features of a natural pathogen infection without pathology that inhibits development of protective adaptive immunity. Vaccine features such as expression of the native transmembrane glycoprotein on the surface of infected cells, infection directed to cells and tissues specified by the tropism of the foreign glycoprotein, and the presentation of immunogen arrayed on virus particles all likely play important roles in shaping the immune response. Moreover, the lack of a G gene in the vector is very important, because it eliminates expression of a dominant off-target B cell immunogen, prevents development of potent anti-G antibodies, and allows the foreign glycoprotein to be repetitively arrayed on the virus particle without interference from G.

To evaluate whether the promising preclinical performance of VSVΔG-Env.BG505 can be extended to humans, as it was for the VSVΔG-ZEBOV vaccine, Applicants are developing a clinical trial candidate. It is relevant to clinical development to mention that the G gene deletion in VSVΔG-ZEBOV resulted in loss of the VSV neurovirulence phenotype that is observed in some preclinical models (42). Advancing VSVΔG-Env.BG505 to clinical trial will be valuable, as it will answer whether the live chimeric virus platform can be used to safely induce Env binding antibodies with properties like those described above in healthy clinical trial volunteers.

Molecular Cloning, Recombinant Proteins, and Cell Line Development.

The VSV genomic clone is based on the VSV Indiana (IND) serotype (16). The plasmid vector containing the VSV genomic clone was similar to one used before (46) except that the T7 RNA polymerase promoter was replaced with a longer version that improves T7 RNA polymerase processivity (T7-g10 (47) and a hammerhead ribozyme sequence was positioned between the T7-g10 promoter and the beginning of the VSV nucleotide sequence (48). The hepatitis delta virus ribozyme and T7 terminator sequences downstream of the 3' end of the VSV antigenome were the same as used before (46). Modified genomic clones with the G IND or G New Jersey (NJ) gene moved to genomic position 6 (VSV-G6, FIG. 25C) were described earlier (16) and a third clone was developed for this study using Maraba (MAR) virus G (Genbank HQ660076.1). Plasmids that express the VSV structural proteins (N, P, M, G, and L) under control of the CMV promoter were used to support VSV rescue (16) instead of those controlled by the T7 promoter used in the earlier procedure (46). A plasmid designed to express T7 RNA polymerase from the CMV promoter was designed similarly to the one described previously (46).

Figures 30A, 30B, 30C, 30D, 30E, 30F:
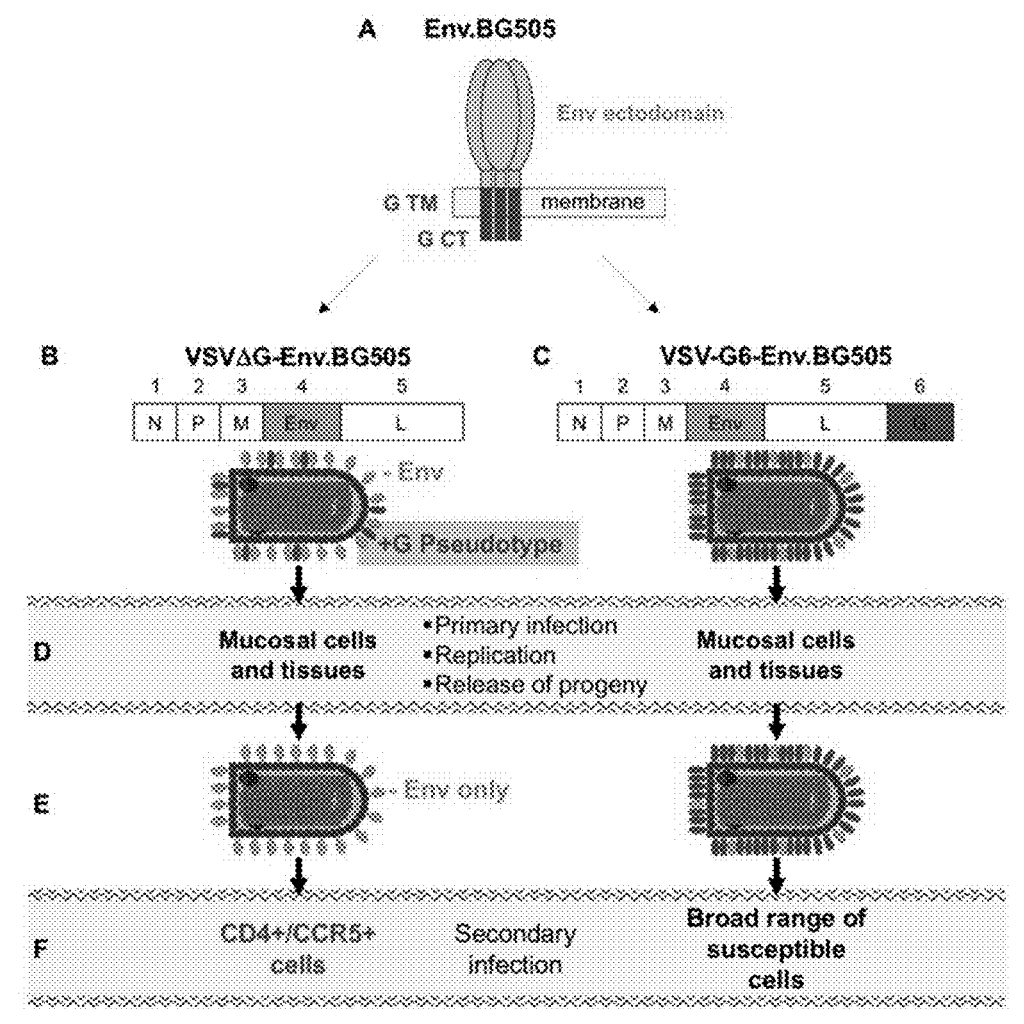

The Env immunogen expressed by VSVΔG-Env.BG505 and VSV-G6-Env.BG505 was based on the wild-type clade A Env.BG505 amino acid sequence (Genbank ABA61516, 49, 50). Env.BG505 was modified by replacing the signal sequence, transmembrane region and cytoplasmic tail with corresponding regions of G from VSV IND (FIG. 30A). The nucleotide sequence encoding the modified Env.BG505 was optimized with a VSV codon bias as described previously (16) after which the gene was inserted in the VSV genomic clone in place of G. Additional VSVΔG-Env chimeras were developed similarly based on Env C.CH505 (week 100; Genbank KC247391.1) and Env B. SF162p3 (Genbank KF042063).

A series of plasmids also were constructed to allow expression of several different domains of Env.BG505 fused to the C-terminus of human serum (HSA, 31). A glycine-serine linker (GGGGS (SEQ ID NO: 6)) was inserted between the C-terminus of HSA and the Env sequence, and a C-terminal histidine tag was added to enable chromatographic purification of HSA-fusion proteins secreted from transfected cells. The HSA fusion proteins were expressed by transfecting 293T cells and purified as described previously (49). His-tagged Env.BG505 gp120 (49) and gp140 containing a flexible linker in place of the furin cleavage site (51) were expressed and purified similarly.

A stable VERO cell line expressing human CD4 and CCR5 (VERO-CD4/CCR5) was developed for propagating the VSVΔG-Env.BG505 vector. The human CD4 and CCR5 coding sequences were joined by a 2A-like element (52) to form a single cistron (CCR5-2A-CD4), which was inserted into a plasmid under the control of a transcription unit developed from the human heat shock protein 60 gene (53). A stable cell line was generated by introducing DNA into cells by microporation (Neon Transfection System, Invitrogen) and selecting clonal isolates resistant to G418.

Cell Culture and Virus.

Recombinant virus recovery from DNA and virus propagation was performed using VERO or VERO-CD4/CCR5 cells. Three media were used for VERO cell propagation and electroporation procedures that were similar to those described before (46). VERO cell medium 1 (VCM1) is Dulbecco's modified Eagle's medium (DMEM) supplemented with 10% heat-inactivated fetal bovine serum, 220 µM 2-mercaptoethanol, 2 mM L-glutamine, 1 mM sodium pyruvate, and 0.1 mM MEM nonessential amino acids. VCM2 is Iscove's modified Dulbecco's medium (IMDM) supplemented with 220 µM 2-mercaptoethanol, 1% DMSO, 2 mM L-glutamine, 1 mM sodium pyruvate, and 0.1 mM MEM nonessential amino acids. VCM3 is the same as VCM1 with addition of 50 µg/mL Gentamicin. The VERO-CD4/CCR5 cell line was propagated in VCM3 containing 1 mg per mL G418. All medium and supplements were obtained from ThermoFisher.

Recombinant VSV was rescued from DNA using a helper-virus-free method adapted from Witko et al. (46) using the modified plasmids described above. Virus rescue was initiated by electroporation of plasmids encoding T7 RNA polymerase, VSV N, P, M, G, and L, and the appropriate VSV genomic clone into VERO (for VSV-G6) or VERO-CD4-CCR5 (for VSVΔG) cells. Conditions for electroporation with a BTX ECM 830 instrument (Harvard Apparatus) and subsequent virus recovery were similar to those used in the earlier method (46).

Figures 31A, 31B, 31C:
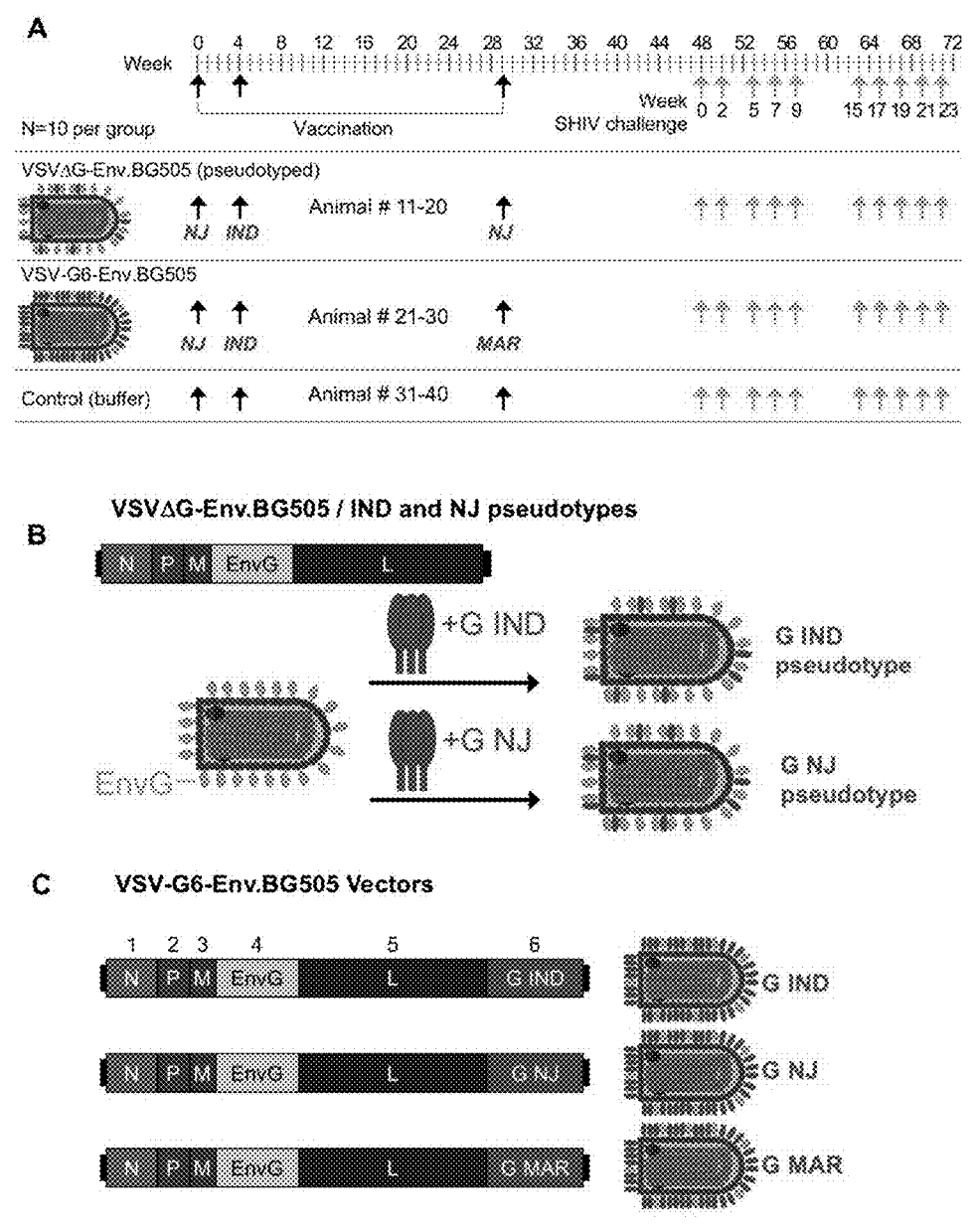

To ensure efficient vaccination with either vaccine, two vector-specific modifications were applied, but the fundamental vaccine designs shown in FIGS. 25A-C were not changed. These modifications enhanced vaccine delivery without altering the Env-dependent propagation of VSVΔG-Env.BG505 or the G-dependent propagation of VSV-G6-Env.BG505. The modifications are illustrated in FIGS. 30 and 31). To enhance mucosal VSVΔG-Env.BG505 uptake, vaccine material was prepared as a pseudotyped virus particle bearing G (G pseudotype; FIGS. 30B and 31A-B). This was done simply by amplifying vaccine material in VERO-CD4/CCR5 cells that transiently expressed VSV G. Pseudotyped VSVΔG-Env.BG505 launches a more robust initial infection, because G recognizes a ubiquitous receptor found on a wide range of cells (17). Importantly, G is not expressed by cells infected with pseudotyped VSVΔG-Env.BG505 and all subsequent rounds of infection in vivo are Env dependent (FIG. 30). For VSV-G6-Env.BG505, it was modified to reduce the negative effects of anti-G antibodies that develop during repeated vaccination with vectors expressing G. Three versions of VSV-G6-Env.BG505 (FIGS. 31A and C) were used in sequence during the three-dose regimen (FIG. 31A). Each version of VSV-G6-Env.BG505 differed only in the G gene (FIG. 31C), which was exchanged with sequences from three different vesiculoviruses including VSV IND, VSV NJ, and Maraba virus (16, 54).

Large batches of VSVΔG-Env.BG505 or VSV-G6-Env.BG505 were amplified using VERO-CD4/CCR5 or VERO cells, respectively. Cell monolayers were grown in Cell Factories (Corning) using VCM3, but once infection was initiated, the medium was changed to Virus Production Serum-Free Medium (VPSFM, supplemented with 4 mM L-Glutamine, 50 U/mL Penicillin and 50 µg/mL Streptomycin; ThermoFisher). Cells were infected with ~0.1 plaque-forming units per cell and then incubated for about 24 h before the medium supernatant was harvested and clarified by centrifugation at 900×g for 30 m at room temperature. Clarified supernatants were overlaid on 20% sucrose cushions prepared in phosphate-buffered saline (PBS), then centrifuged for 2 hrs (18,000 rpm, 42,900 g, 4° C.) using a SW28 rotor (Beckman Coulter). The sucrose solution was aspirated completely from the virus pellet after which virus was suspended in Hank's Balanced Salt Solution (HBSS, ThermoFisher) containing 15% Trehalose (Life Sciences Advanced Technologies) that was adjusted to pH 7.2. Virus suspensions were stored at −80° C. in aliquots.

Pseudotyped VSVΔG-Env.BG505 was produced in VERO-CD4/CCR5 cells that were electroporated with plasmid expressing VSV G IND or NJ. In preparation for electroporation, cells were harvested and treated as described before (46) and were suspended in 0.7 ml of VCM2 (~2×10$^7$ cells). Purified VSVΔG-Env.BG505 (0.1 pfu per cell) and 50 ug of pCMV-G expression plasmid was added to the cell suspension before performing electroporation with the BTX ECM830 instrument. After electroporation, the cells were processed and transferred to one T175 flask per electroporation cuvette, after which they were cultured in VCM1 for 3-4 hours at 37° C. before performing heat shock (43° C.) for 3 hours (46). After heat shock, the cells were returned to 37° C. and allowed to recover for 2 h before the medium was removed and replaced VPSFM supplemented with 4 mM L-Glutamine. Incubation was continued 24-48 hours at 37° C. until cytopathic effect was evident throughout the culture after which virus was harvested and purified as described above.

VSV vector infectious units were quantified by plaque assay (16). For VSVΔG-Env.BG505, GHOST-CD4-CCR5 cell monolayers were used (NIH AIDS Reagent Program, Division of AIDS, NIAID, NIH, catalog number 3944, 55) while VERO cells were used for VSV-G6-Env.BG505. Near-confluent cell monolayers were infected with serially diluted virus before being overlaid with VCM3 containing 0.8% agarose. When plaques were visible, cells were fixed with 7% formaldehyde and stained with a solution of 7% crystal violet in water. Plaques were counted from duplicate wells and infectious titers were expressed as plaque-forming units (pfus) per ml.

Western blotting was used to confirm Env expression by infected cells and also to characterize purified VSV vector particles. For analysis of Env expression, cytoplasmic lysates were prepared from infected monolayers using Cell-Lytic M reagent (Sigma). Lysate proteins were then subjected to denaturing SDS polyacrylamide gel electrophoresis (SDS PAGE) and transferred to nitrocellulose membranes. Proteins were detected with monoclonal antibodies or polyclonal serum specific for Env gp120.BG505 or VSV structural proteins. Secondary antibodies conjugated to horseradish peroxidase and chemiluminescence detection was used to visualize specific bands. Protein composition of VSV vector particles was analyzed by Western blot using similar methods applied to virus purified by centrifugation through sucrose cushions.

VSV vector vaccine material was subjected to several tests to ensure the quality. Endotoxin levels were tested using the Endosafe Portable Test System (Charles River Laboratories, Boston). All vaccine lots had endotoxin levels less than 10 EU/ml. The absence of *Mycoplasma* was confirmed by PCR using the MycoSEQ® *Mycoplasma* Detection System (Life Technologies). Residual VERO cell DNA was less than 10 ng per dose as determined with the resDNASEQ® Vero Residual DNA Quantitation System (Life Technologies). Gene sequences were confirmed by nucleic acid sequencing as described before (16).

Vaccinations, SHIV Challenge, and Animal Care and Use.

Purpose-bred male Indian rhesus macaques were 4-7 years of age when they arrived at The State University of New York (SUNY) Downstate Medical Center, Division of Comparative Medicine. Animal care and use complied with The United States Department of Agriculture and The New York State Department of Health regulations. The SUNY Downstate Medical Center Institutional Animal Care and Use Committee reviewed all experimental procedures. Prior to receipt, all macaques were confirmed to be negative for Herpes B virus (BV), tuberculosis (TB), simian immunodeficiency virus (SIV), simian retrovirus (SRV), and simian T lymphotropic virus (STLV), as well as *Shigella* and *Campylobacter jejuni*.

No Macaques were included in the study if they were positive for MHC alleles Mamu-B*08 and B*17 associated with strong SIV replication control (56). Both groups vaccinated with VSV vectors each had 2 animals that were positive for Mamu-A*01 and two positive A*02, which have been associated with control of disease progression (56). The placebo control group also contained two animals that were positive for A*02 and one for A*01. For vaccination, macaques were sedated and positioned in dorsal recumbency after which vaccine was administered by the intraoral and intranasal routes. Vaccine or buffer control was administered by drops using a 1000 µl micropipette. 500 µl was delivered intranasally by alternating drops between the left and right nares, with time between drops allowed for the droplet to be inhaled. For intraoral, a total of 500 µl was administered by drops applied sublingually on the frenulum (250 µl) and to the anterior buccal surface of the inferior lip (250 µl) followed by 30-60 seconds of gentle massage to help distribute the inoculum. Animals were kept in dorsal recumbency throughout the procedure and were left in this position for an additional 5 minutes before being returned to their cages. Animals were singly housed for 48 h following all vaccinations, after which they were housed together (2-3 animals per cage) within the same vaccination group. Bedding material was analyzed for VSV genomes by qPCR and none was detected (data not shown).

Rectal challenge was performed using SHIV SF162p3 that was prepared in primary cultures of macaque PBMCs (34). The inoculum (total of $2.2 \times 10^4$ TCID50) consisted of virus in 1 ml of saline or RPMI medium. Sedated animals were positioned in sternal recumbency with the posterior elevated by placing an empty plastic container between the lower abdomen and the procedure table. Inoculation was performed by atraumatic insertion of a lightly lubricated 3 mL syringe approximately 5 cm into the rectum. The inoculum was slowly instilled over a one-minute period with the syringe left in place for and additional 4 minutes. After removing the syringe, macaques remained in sternal recumbency for 10 minutes. Challenged animals were caged separately for 48 h before being housed in groups of 2-3 within the same vaccination group.

SHIV infection was monitored by reverse transcription and quantitative PCR (RT-qPCR) using methods similar to those described earlier (57). Briefly, virus from 1.0 ml of plasma was collected by centrifugation at 25,000×g for 90 min (5° C.). The virus pellet was processed using the RNeasy Micro kit (Qiagen) by suspending virus in solution containing 300 µl of lysis buffer, 3 µl of 14.2 M 2-mercaptoethanol (Bio-Rad), and 16 µl of 20 mg/ml proteinase K (Qiagen). Samples were digested at 56° C. for 1 h, then RNA was purified using spin columns following the RNeasy Micro kit protocol. RNA was eluted in 50 µl of RNase-free water supplemented with 1 mM dithiothreitol (Sigma) and 1 U/µl RNAseOUT (Thermo Fisher Scientific) after which duplicate RT reactions were performed using 15 µl of purified RNA per reaction and 10 µl of a cocktail composed of reagents from the Sensiscript Reverse Transcriptase kit (Qiagen, Valencia, Calif., USA) including 1× reverse transcription buffer, 0.5 mM of each dNTP, 10 U/reaction RNase Inhibitor (Invitrogen, Carlsbad, Calif., USA), 10 Units Sensiscript Reverse transcriptase, and Gag-specific reverse primer (400 nM, 5'-CACTAGKTGTCTCTGCACTATPT-GTTT-3'(SEQ ID NO: 3)) that annealed to the positive-sense genomic RNA. Reverse transcription was performed at 50° C. for 45 min and terminated by heat inactivation (95° C. for 2 min). The heat-inactivated 25-µl reaction was adjusted for qPCR by adding 30 µl of a reagent mix composed of 1× QuantiTect Multiplex PCR Master Mix (Qiagen), 400 nM of Gag-specific forward primer (5'-GTCTGCGTCATPTGGT-GCAT-3' SEQ ID NO: 4)) and Gag-specific reverse primer, and 200 nM 6-carboxyfluorescein (FAM)-labeled minor groove binder (MGB) probe (5'-6FAM-CTTCPTCAGTKT-GTTTCA-MGB-3' SEQ ID NO: 5)). A Stratagene Mx3005P Sequence Detection System was used for amplification and detection with the following conditions: 15 min at 95° C. followed by 45 cycles of 60 secs at 94° C. and 90 secs at 60° C. Results from duplicate test samples were averaged and genome copy numbers were interpolated from a curve generated with known RNA standards. Positive samples were defined as 200 genome copies per ml of plasma.

Analysis of Immune Responses.

To prepare plasma and peripheral blood mononuclear cells (PBMCs), blood was collected in tubes coated with sodium heparin. Plasma was prepared by removing cells by centrifugation and storage at −20° C. PBMCs were isolated by density gradient centrifugation on Ficoll Hypaque (GE Healthcare) in Accuspin tubes (Sigma-Aldrich) as described previously (57). Harvested PBMCs were suspended in Recovery Cell Culture Freezing Medium (Thermo Fisher Scientific) and stored in liquid nitrogen. Serum used for ELISA, Western blot procedures, binding antibody multiplex assays, or HIV pseudovirus neutralization assays was prepared from whole blood collected and processed in serum separator tubes (SST). Aliquots were stored at −20° C.

Intracellular cytokine staining was performed as described before (57). T cells were stimulated with Env.BG505 peptide (Genscript) 15-mers overlapping by 11 amino acids. Two different Env.BG505 peptide pools, spanning gp120 or gp41, were used at 4 µg per ml. All flow cytometry data had mock background responses subtracted.

Infected VERO and VERO-CD4/CCR5 cells and VSV vector particles also were analyzed by flow cytometry. For infected cells, VERO or VERO-CD4/CCR5 monolayers were infected with 0.1 to 1.0 pfu per cell and incubated overnight at 37°. The following day, cells were washed with PBS and then treated with Enzyme-free Cell Dissociation Buffer (Life Sciences) to produce a cell suspension. The cells were collected by centrifugation and then suspended in PBS before being incubated with Env-specific monoclonal antibodies. Flow cytometry was performed as described earlier (16).

Env incorporated in VSV particles also was analyzed by flow cytometry (16). Typically, purified virus ($10^8$ pfus) was bound to 100 ug Alum (Adju-Phos, Brenntag, Denmark) and the alum/virus complexes were blocked with PBS containing 3% BSA before being incubated with primary antibodies. After primary antibody incubation, the complexes were collected by centrifugation, washed using PBS containing 3% BSA, and then incubated with labeled secondary antibody. Centrifugation and washing was repeated before analysis with a LSRII flow cytometer (Becton Dickinson). The flow cytometer was set to analyze 30,000 particles with forward scatter (FSC) and side scatter (SSC) set to log 10 scale and threshold set to 4000. Data was analyzed using FlowJo software version 9.4 (Tree Star), where complexes were gated according to positivity compared to an alum only control.

Western blotting also was used for analysis of serum antibodies. Polypeptide substrates used for the analysis were either purified VSVΔG-EnvG.BG505 particles (no G pseudotype, 5×10$^8$ pfus) or purified Env proteins. Purified virus or protein was diluted to 162.5 µL in HBSS containing 15% Trehalose before being mixed with 62.5 µl LDS NuPAGE sample buffer (Novex) and 25 µL of NuPAGE Sample Reducing Agent (Novex). Samples were heat denatured before being electrophoresed in a denaturing preparative gel (NuPAGE 4-12% Bis-Tris 2D, ThermoFisher), and afterwards proteins were transferred to a nitrocellulose membrane. The membrane was rinsed with PBS and then incubated at room temperature for 1 h in blocking buffer composed of StartingBlock T20 buffer (ThermoFisher) supplemented with Clear Milk (Pierce/ThermoFisher) and 1% goat serum (Sigma). The blocked membrane was transferred to a multichannel Mini Protein II MultiScreen (Bio-Rad) device that created multiple channels for analysis of sera from individual macaques. Individual lanes were incubated for 1 h at room temperature with heat-inactivated macaque serum (diluted 1:300 in blocking buffer for a total volume of 550 µL) before the solution was aspirated completely from each lane. The membrane was then removed from the multiscreen device and rinsed 5 times with miliQ water (59) and then washed 3 times for 5 minutes each with PBS containing 0.1% Tween-20. The membrane was incubated with secondary antibody (mouse anti-monkey IgG, SouthernBiotech; diluted 1:10,000 in blocking buffer) for 45 mins at room temperature after which it was washed as described above. The blot was developed with chemiluminescence reagent (SuperSignal West Femto Maximum Sensitivity Substrate, ThermoFisher) and imaged with a Biorad ChemiDoc Touch Imaging System.

REFERENCES AND NOTES

1. UNAIDS, Fact Sheet 2016 UNAIDS.
2. T. M. Harmon et al., Exploring the Potential Health Impact and Cost-Effectiveness of AIDS Vaccine within a Comprehensive HIV/AIDS Response in Low- and Middle-Income Countries. *PLoS ONE* 11, e0146387 (2016).
3. M. A. Checkley, B. G. Luttge, E. O. Freed, HIV-1 envelope glycoprotein biosynthesis, trafficking, and incorporation. *Journal of Molecular Biology* 410, 582-608 (2011).
4. D. R. Burton, J. R. Mascola, Antibody responses to envelope glycoproteins in HIV-1 infection. *Nature immunology* 16, 571-576 (2015).
5. P. D. Kwong, J. R. Mascola, G. J. Nabel, Broadly neutralizing antibodies and the search for an HIV-1 vaccine: the end of the beginning. *Nat Rev Immunol* 13, 693-701 (2013).
6. A. B. Ward, I. A. Wilson, Insights into the trimeric HIV-1 envelope glycoprotein structure. *Trends Biochem Sci* 40, 101-107 (2015).
7. R. J. O'Connell, J. H. Kim, L. Corey, N. L. Michael, Human immunodeficiency virus vaccine trials. *Cold Spring Harb Perspect Med* 2, a007351 (2012).
8. J. H. Kim, J. L. Excler, N. L. Michael, Lessons from the RV144 Thai phase III HIV-1 vaccine trial and the search for correlates of protection. *Annual review of medicine* 66, 423-437 (2015).
9. S. A. Plotkin, Correlates of protection induced by vaccination. *Clin Vaccine Immunol* 17, 1055-1065 (2010).
10. C. L. Parks, L. J. Picker, C. R. King, Development of replication-competent viral vectors for HIV vaccine delivery. *Curr Opin HIV AIDS* 8, 402-411 (2013).
11. M. F. Bachmann, G. T. Jennings, Vaccine delivery: a matter of size, geometry, kinetics and molecular patterns. *Nat Rev Immunol* 10, 787-796 (2010).
12. E. Boritz, J. Gerlach, J. E. Johnson, J. K. Rose, Replication-competent rhabdoviruses with human immunodeficiency virus type 1 coats and green fluorescent protein: entry by a pH-independent pathway. *J Virol* 73, 6937-6945 (1999).
13. S. M. Jones et al., Live attenuated recombinant vaccine protects nonhuman primates against Ebola and Marburg viruses. *Nature medicine* 11, 786-790 (2005).
14. A. M. Henao-Restrepo et al., Efficacy and effectiveness of an rVSV-vectored vaccine expressing Ebola surface glycoprotein: interim results from the Guinea ring vaccination cluster-randomised trial. *Lancet* 386, 857-866 (2015).
15. S. T. Agnandji et al., Phase 1 Trials of rVSV Ebola Vaccine in Africa and Europe. *The New England journal of medicine* 374, 1647-1660 (2016).
16. S. Rabinovich et al., A novel, live-attenuated vesicular stomatitis virus vector displaying conformationally intact, functional HIV-1 envelope trimers that elicits potent cellular and humoral responses in mice. *PLoS ONE* 9, e106597 (2014).
17. E. Hastie, M. Cataldi, I. Marriott, V. Z. Grdzelishvili, Understanding and altering cell tropism of vesicular stomatitis virus. *Virus Res* 176, 16-32 (2013).
18. R. W. Sanders et al., A next-generation cleaved, soluble HIV-1 Env trimer, BG505 SOSIP.664 gp140, expresses multiple epitopes for broadly neutralizing but not non-neutralizing antibodies. *PLoS Pathog* 9, e1003618 (2013).
19. E. Falkowska et al., Broadly Neutralizing HIV Antibodies Define a Glycan-Dependent Epitope on the Prefusion Conformation of gp41 on Cleaved Envelope Trimers. *Immunity*, (2014).
20. Y. Li et al., HIV-1 neutralizing antibodies display dual recognition of the primary and coreceptor binding sites and preferential binding to fully cleaved envelope glycoproteins. *J Virol* 86, 11231-11241 (2012).
21. P. L. Moore et al., Nature of nonfunctional envelope proteins on the surface of human immunodeficiency virus type 1. *J Virol* 80, 2515-2528 (2006).
22. F. Sallusto, A. Lanzavecchia, K. Araki, R. Ahmed, From vaccines to memory and back. *Immunity* 33, 451-463 (2010).
23. J. E. Johnson et al., Neurovirulence properties of recombinant vesicular stomatitis virus vectors in non-human primates. *Virology* 360, 36-49 (2007).
24. C. Selinger et al., Multiple low-dose challenges in a rhesus macaque AIDS vaccine trial result in an evolving host response that affects protective outcome. *Clin Vaccine Immunol* 21, 1650-1660 (2014).
25. R. R. Regoes, The role of exposure history on HIV acquisition: insights from repeated low-dose challenge studies. *PLoS Comput Biol* 8, e1002767 (2012).
26. M. G. Hudgens, P. B. Gilbert, Assessing vaccine effects in repeated low-dose challenge experiments. *Biometrics* 65, 1223-1232 (2009).
27. D. C. Montefiori, in *HIV Protocols: Second Edition, vol.* 485, V. R. Prasad, G. V. Kalpana, Eds. (Humana Press, New York, 2009), chap. 26, pp. 395-405.
28. Y. Fukazawa et al., Lymph node T cell responses predict the efficacy of live attenuated SIV vaccines. *Nature medicine* 18, 1673-1681 (2012).

29. B. F. Haynes et al., Immune-correlates analysis of an HIV-1 vaccine efficacy trial. *The New England journal of medicine* 366, 1275-1286 (2012).
30. G. D. Tomaras et al., Initial B-cell responses to transmitted human immunodeficiency virus type 1: virion-binding immunoglobulin M (IgM) and IgG antibodies followed by plasma anti-gp41 antibodies with ineffective control of initial viremia. *J Virol* 82, 12449-12463 (2008).
31. J. Carter et al., Fusion partners can increase the expression of recombinant interleukins via transient transfection in 2936E cells. *Protein Sci* 19, 357-362 (2010).
32. R. Gottardo et al., Plasma IgG to linear epitopes in the V2 and V3 regions of HIV-1 gp120 correlate with a reduced risk of infection in the RV144 vaccine efficacy trial. *PLoS ONE* 8, e75665 (2013).
33. D. H. Barouch et al., Protective efficacy of adenovirus/protein vaccines against SIV challenges in rhesus monkeys. *Science* 349, 320-324 (2015).
34. D. H. Barouch et al., Protective efficacy of a global HIV-1 mosaic vaccine against heterologous SHIV challenges in rhesus monkeys. *Cell* 155, 531-539 (2013).
35. Q. Li et al., Live simian immunodeficiency virus vaccine correlate of protection: local antibody production and concentration on the path of virus entry. *J Immunol* 193, 3113-3125 (2014).
36. M. Shingai et al., Passive transfer of modest titers of potent and broadly neutralizing anti-HIV monoclonal antibodies block SHIV infection in macaques. *J Exp Med* 211, 2061-2074 (2014).
37. C. J. Henry Dunand et al., Both Neutralizing and Non-Neutralizing Human H7N9 Influenza Vaccine-Induced Monoclonal Antibodies Confer Protection. *Cell host & microbe* 19, 800-813 (2016).
38. H. M. Yassine et al., Hemagglutinin-stem nanoparticles generate heterosubtypic influenza protection. *Nature medicine* 21, 1065-1070 (2015).
39. M. K. Slifka, I. Amanna, How advances in immunology provide insight into improving vaccine efficacy. *Vaccine* 32, 2948-2957 (2014).
40. N. Honke et al., Enforced viral replication activates adaptive immunity and is essential for the control of a cytopathic virus. *Nature immunology* 13, 51-57 (2012).
41. C. E. Mire et al., A Single-Vector, Single-Injection Trivalent Filovirus Vaccine: Proof of Concept Study in Outbred Guinea Pigs. *J Infect Dis* 212 Suppl 2, S384-388 (2015).
42. C. E. Mire et al., Recombinant vesicular stomatitis virus vaccine vectors expressing filovirus glycoproteins lack neurovirulence in nonhuman primates. *PLoS Negl Trop Dis* 6, e1567 (2012).
43. D. S. Lyles, I. Kuzmin, C. E. Rupprecht, in *Fields Virology*, D. M. Knipe, P. M. Howley, Eds. (Lippincott Williams and Wilkins, Philadelphia, 2013), vol. 1, chap. 31, pp. 885-922.
44. J. E. Johnson, M. J. Schnell, L. Buonocore, J. K. Rose, Specific targeting to CD4+ cells of recombinant vesicular stomatitis viruses encoding human immunodeficiency virus envelope proteins. *J Virol* 71, 5060-5068 (1997).
45. A. De Milito, B lymphocyte dysfunctions in HIV infection. *Curr HIV Res* 2, 11-21 (2004).
46. S. E. Witko et al., An efficient helper-virus-free method for rescue of recombinant paramyxoviruses and rhadoviruses from a cell line suitable for vaccine development. *J Virol Methods* 135, 91-101 (2006).
47. P. J. Lopez, J. Guillerez, R. Sousa, M. Dreyfus, The low processivity of T7 RNA polymerase over the initially transcribed sequence can limit productive initiation in vivo. *Journal of molecular biology* 269, 41-51 (1997).
48. K. Inoue et al., An improved method for recovering rabies virus from cloned cDNA. *J Virol Methods* 107, 229-236 (2003).
49. S. Hoffenberg et al., Identification of an HIV-1 clade A envelope that exhibits broad antigenicity and neutralization sensitivity and elicits antibodies targeting three distinct epitopes. *J Virol* 87, 5372-5383 (2013).
50. X. Wu et al., Neutralization escape variants of human immunodeficiency virus type 1 are transmitted from mother to infant. *J Virol* 80, 835-844 (2006).
51. S. K. Sharma et al., Cleavage-Independent HIV-1 Env Trimers Engineered as Soluble Native Spike Mimetics for Vaccine Design. *Cell Rep* 11, 539-550 (2015).
52. P. de Felipe et al., E unum pluribus: multiple proteins from a self-processing polyprotein. *Trends Biotechnol* 24, 68-75 (2006).
53. J. J. Hansen et al., Genomic structure of the human mitochondrial chaperonin genes: HSP60 and HSP10 are localised head to head on chromosome 2 separated by a bidirectional promoter. *Hum Genet* 112, 71-77 (2003).
54. N. F. Rose et al., An effective AIDS vaccine based on live attenuated vesicular stomatitis virus recombinants. *Cell* 106, 539-549 (2001).
55. A. Morner et al., Primary human immunodeficiency virus type 2 (HIV-2) isolates, like HIV-1 isolates, frequently use CCR5 but show promiscuity in coreceptor usage. *J Virol* 73, 2343-2349 (1999).
56. P. J. Goulder, D. I. Watkins, Impact of MHC class I diversity on immune control of immunodeficiency virus replication. *Nat Rev Immunol* 8, 619-630 (2008).
57. N. Winstone et al., Enhanced control of pathogenic Simian immunodeficiency virus SIVmac239 replication in macaques immunized with an interleukin-12 plasmid and a DNA prime-viral vector boost vaccine regimen. *J Virol* 85, 9578-9587 (2011).
58. N. L. Yates et al., Vaccine-induced Env V1-V2 IgG3 correlates with lower HIV-1 infection risk and declines soon after vaccination. *Sci Transl Med* 6, 228ra239 (2014).
59. M. Wu, P. G. Stockley, W. J. Martin, 2nd, An improved western blotting technique effectively reduces background. *Electrophoresis* 23, 2373-2376 (2002).
60. T. L. Nolen, M. G. Hudgens, P. K. Senb, G. G. Koch, Analysis of repeated low-dose challenge studies. *Stat Med* 34, 1981-1992 (2015).
61. J. E. Johnson et al., In vivo biodistribution of a highly attenuated recombinant vesicular stomatitis virus expressing HIV-1 Gag following intramuscular, intranasal, or intravenous inoculation. *Vaccine* 27, 2930-2939 (2009).
62. Y. Huang, P. B. Gilbert, D. C. Montefiori, S. G. Self, Simultaneous Evaluation of the Magnitude and Breadth of a Left and Right Censored Multivariate Response, with Application to HIV Vaccine Development. *Statistics in biopharmaceutical research* 1, 81-91 (2009).
63. H. X. Liao et al., Co-evolution of a broadly neutralizing HIV-1 antibody and founder virus. *Nature* 496, 469-476 (2013).

Example 3: Using VSV Evolution to Fine Tune the Env Immunogen

The EnvG hybrid was developed with the goal of producing an immunogen that was optimal for delivery with a live VSV vector. The Env-G design objectives were to generate a modified immunogen that enabled more abundant expression on the infected cell surface and increased incorporation in VSV particles while maintaining native Env antigenic properties and the ability to direct infection and replication in cells bearing the HIV coreceptors CD4 and CCR5 (CD4+/CCR5+ cells). Systematic evaluation of several Env domain substitutions demonstrated that replacement of the Env signal peptide (SP), transmembrane region (TM), and cytoplasmic tail (CT) with analogous domains from VSV G substantially improved expression of Env on the cell surface (FIG. 1). Moreover, the surface of cells expressing the Env-G hybrid was bound by a panel of anti-Env monoclonal antibodies demonstrating that the antigenic profile was very similar to Env expressed by cells infected with HIV. Importantly, when a chimeric VSVΔG-Env vector was developed in which the G gene was replaced with Env-G, replication-competent recombinant virus was isolated that replicated specifically in CD4+/CCR5+ cells demonstrating that the EnvG retained functions that are essential for cell attachment and virus replication.

The domain swap approach enabled development of a live VSVΔG-Env chimera that readily propagated in CD4+/CCR5+ cells. After conducting multiple rounds of amplification in CD4+/CCR5+ cells, virus emerged that grew to higher titers suggesting that one or more mutations occurred resulting in a virus with increased replicative fitness. Genomic sequence analysis conducted on this virus strain identified three amino acid substitutions in Env, which were (amino acid numbering according to reference strain HXB2): K169T in the second variable domain of Env (V2 domain), I307T in the V3 domain, and W672R in the membrane-proximal external region (MPER). Consistent with these substitutions being the adaptive mutations that improve replicative fitness of the virus, the three amino acid changes have been stable during numerous subsequent rounds of virus propagation. Moreover, there was a substantial difference in virus quantities produced from infected cultures; VSVΔG-Env.BG505 with the three substitutions routinely exceeds 1×10e7 PFU per ml of medium while VSVΔG-Env.BG505 amplified prior to adaptation produced titers closer to 1×10e6.

To provide additional evidence that the three substitutions were the result of adaptive mutations that improved replicative fitness, the mutations were incorporated into the VSVΔG-Env.BG505 genomic DNA clone and a new recombinant virus was recovered containing the Env substitutions. This new recombinant strain grew efficiently, maintained the three amino acid substitutions during many rounds of propagation, and accrued no additional EnvG mutations. These results indicated that the three amino acid substitutions provided a replicative fitness advantage for the VSVΔG-Env.BG505 chimera.

The accrual of the three amino acid substitutions that enhanced replicate fitness indicated that EnvG structure likely required some additional 'fine tuning' to support optimal VSVΔG-Env.BG505 growth. The substitutions probably compensated for some structural changes in the Env complex that resulted from replacement of TM and CT with VSV G sequence. Structural changes in the Env complex are known to occur when mutations are introduced into the Env TM (1) and CT (2); thus, it is reasonable to expect that replacement of the Env TM and CT with VSV G sequence will cause some structural alteration that requires compensatory second-site mutations to achieve optimal EnvG function and virus replicative fitness.

It was noticeable that the three Env substitutions occurred in the Env ectodomain rather than in the G TM or CT. This probably reflects strong selective pressure to maintain the wild-type G TM and CT sequence, as they are optimal for VSV particle structure, and in fact, the G CT makes contact with the underlying VSV matrix protein (3). Thus, selective pressure favored accrual of compensatory amino acid changes in the Env ectodomain rather than in the G TM or CT.

It was also notable that the adaptive mutations occurred in three separate regions of the Env ectodomain including the gp120 (V2 K169T and V3 I307T) and gp41 (MPER W672R) subunits. The mechanism by which this combination of amino acid substitutions improves replicative fitness is unknown. Furthermore, this makes it difficult to predict what substitutions might be useful for optimizing propagation of a chimeric virus like VSVΔG-EnvG.BG505; thus, VSV's ability to rapidly evolve when faced with selective pressure (4) is an important tool in the overall VSVΔG-Env vaccine design process.

TABLE

EnvG amino acid substitutions in VSVΔG-EnvG.BG505 Amino acid substitutions that accrued after multiple rounds of amplification in two independent VSVΔG-Env.BG505 recombinants are shown

|  | Env amino acids | | | |
| --- | --- | --- | --- | --- |
| VSVΔG-Env.BG505 vaccine | 169 | 307 | 672 | |
| DNA clone | K | I | W | |
| Adapted virus | T | T | R | |
| Repeat virus rescue and adaption | 164 | 440 | 434 | 494 |
| DNA clone | E | Q | M | L |
| Adapted virus | G | R | T | F |

To demonstrate the importance of VSV evolution in design of an optimal immunogen and chimeric virus vector, an independent VSVΔG-Env.BG505 recombinant was isolated that lacked adaptive mutations and it was allowed to evolved during serial rounds of propagation. The results showed that the virus did in fact accrue multiple amino acid substitutions as before, but the constellation of adaptive mutations was different. After multiple rounds of amplification, this new strain had 4 substitutions (Table). Interestingly, as before, one of the substitutions was in V2 (E164G). The other three were in constant (C) domains of Env (C4 M434T, C4 Q440R, and C5 L494F).

The VSVΔG-Env.BG505 vaccine containing the K169T, I307T and W672R was found to be efficacious in the Indian Rhesus macaque SHIV challenge model.

CITATIONS

1. Lovelace E, Xu H, Blish C A, Strong R, Overbaugh J. The role of amino acid changes in the human immunodeficiency virus type 1 transmembrane domain in antibody binding and neutralization. Virology. 2011; 421(2):235-44.
2. Chen J, Kovacs J M, Peng H, Rits-Volloch S, Lu J, Park D, et al. HIV-1 ENVELOPE. Effect of the cytoplasmic domain on antigenic characteristics of HIV-1 envelope glycoprotein. Science. 2015; 349(6244):191-5.
3. Ge P, Tsao J, Schein S, Green T J, Luo M, Zhou Z H. Cryo-EM model of the bullet-shaped vesicular stomatitis virus. Science. 2010; 327(5966):689-93.
4. Novella I S. Contributions of vesicular stomatitis virus to the understanding of RNA virus evolution. Curr Opin Microbiol. 2003; 6(4):399-405.

The invention is further described by the following numbered paragraphs:

1. A recombinant vesicular stomatitis virus (VSV) vector wherein the gene encoding the VSV surface glycoprotein G (VSV G) is functionally replaced by functional clade A HIV Env BG505.
2. The vector of paragraph 1 wherein the vector contains and expresses a nucleic acid sequence encoding an amino acid sequence of an Env.BG505 immunogen encoded by the VSVΔG-Env.BG505.
3. The vector of paragraph 1, wherein the amino acid sequence of an Env.BG505 immunogen encoded by the VSVΔG-Env.BG505 is SEQ ID NO: 2.
4. The vector of paragraph 1 wherein the vector comprises the sequence of a VSVΔG-Env.BG505 genomic clone.
5. The vector of paragraph 4, wherein the sequence of a VSVΔG-Env.BG505 genomic clone is SEQ ID NO: 1.
6. The vector of any one of paragraphs 1 to 5 wherein the HIV Env is recognized by antibodies PG9, PG16, 2G12, b12, 2F5, 4E10 or Z13, or other Env-specific antibodies, including broad potent neutralizing trimer-specific antibodies.
7. A vaccine comprising the vector of any one of paragraphs 1 to 6.
8. The vaccine of paragraph 7, wherein the vaccine is a mucosal vaccine.
9. The vaccine of paragraph 7 or 8 wherein the vaccine is a G-pseudotyped VSVΔG-Env.BG505 vaccine.
10. A method of producing an immune response or eliciting an immune response comprising administering to a mammal the vector of any one of claims 1 to 6 or the vaccine of any one of paragraph 7 to 9.
11. The method of claim 10, wherein a dose is about of $2\times10^8$ pfu per ml.
12. The method of paragraph 10 or 11, wherein the vaccine is administered to a nasal and/or oral cavity.
13. The method of paragraph 12, wherein the vaccine is administered to a nasal and oral cavity.
14. The method of paragraph 13, wherein a dose of $1\times10^8$ pfu per ml is administered to each cavity.
15. The method of any one of paragraph 10 to 14 wherein the vaccine is administered over a vaccination schedule from about 0 to 29 weeks.
16. The method of paragraph 15, wherein the vaccination schedule is at 0, 4 and 29 weeks.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A VeroCD4/CCR5 cell line infected with a recombinant vesicular stomatitis virus (VSV) vector wherein the gene encoding the VSV surface glycoprotein G (VSV G) is functionally replaced by functional clade A HIV Env BG505.

2. The cell line of claim 1 wherein the vector contains and expresses a nucleic acid sequence encoding an amino acid sequence of an Env.BG505 immunogen encoded by the VSVΔG-Env.BG505.

3. The cell line of claim 1, wherein the amino acid sequence of an Env.BG505 immunogen encoded by the VSVΔG-Env.BG505 is SEQ ID NO: 2.

4. The cell line of claim 1 wherein the vector comprises the sequence of a VSVΔG-Env.BG505 genomic clone.

5. The cell line of claim 4, wherein the sequence of a VSVΔG-Env.BG505 genomic clone is SEQ ID NO: 1.

6. The cell line of claim 1 wherein the HIV Env is recognized by antibodies PG9, PG16, 2G12, b12, 2F5, 4E10 or Z13, or broad potent neutralizing trimer-specific antibodies.

7. A vaccine comprising the vector isolated from the cell line of claim 1.

8. The vaccine of claim 7, wherein the vaccine is an intramuscular or mucosal vaccine.

9. The vaccine of claim 7, wherein the vaccine is a G-pseudotyped VSVΔG-Env.BG505 vaccine.

10. The cell line of claim 1 wherein the vector contains and expresses a nucleic acid sequence encoding an amino acid sequence of an Env.BG505 immunogen encoded by the VSVΔG-Env.BG505, and replicates progeny virus.

* * * * *